United States Patent [19]

Havelund et al.

[11] Patent Number: 5,750,497
[45] Date of Patent: May 12, 1998

[54] ACYLATED INSULIN

[75] Inventors: Svend Havelund, Bagsværd; John Halstrøm, Hundested; Ib Jonassen, Valby; Asser Sloth Andersen, Frederiksberg C; Jan Markussen, Herlev, all of Denmark

[73] Assignee: Novo Nordisk A/S, Bagsvaerd, Denmark

[21] Appl. No.: 400,256

[22] Filed: Mar. 8, 1995

Related U.S. Application Data

[63] Continuation-in-part of Ser. No. 190,829, filed as PCT/DK94/00347, Sep. 16, 1994, abandoned.

[30] Foreign Application Priority Data

Sep. 17, 1993 [DK] Denmark ................ 1044/93

[51] Int. Cl.$^6$ .................... C07K 14/62; A61K 38/28
[52] U.S. Cl. ................... 514/3; 514/866; 530/304
[58] Field of Search ................ 514/3, 866; 530/303, 530/304

[56] References Cited

U.S. PATENT DOCUMENTS

| | | | |
|---|---|---|---|
| 3,823,125 | 7/1974 | Grant et al. | 260/112.7 |
| 3,868,356 | 2/1975 | Smyth | 260/112.7 |
| 3,950,517 | 4/1976 | Lindsay et al. | 424/178 |
| 4,645,740 | 2/1987 | Breddam et al. | 435/71 |
| 5,008,241 | 4/1991 | Markussen et al. | 514/3 |

FOREIGN PATENT DOCUMENTS

| | | |
|---|---|---|
| 0 127 535 A2 | 5/1984 | European Pat. Off. |
| 0 511 600 A2 | 11/1992 | European Pat. Off. |
| 22 09 835 | 4/1976 | Germany |
| 1-254699 | 10/1989 | Japan |

| | | |
|---|---|---|
| WO 92/01476 | 2/1992 | WIPO |

OTHER PUBLICATIONS

Brange J., Galenics of Insulin, pp.18–100 (1987).
Blundell T. et al., The Structure in the Crystal and its Reflection in Chemistry and Biology, vol. 26, pp.279–402 (1972).
Hashimoto, et al., Pharmaceutical Research, vol. 6, No. 2, pp. 171–176 (1989).
Muranishi et al., Journal of Controlled Release, vol. 19, pp. 179–188 (1992).
Brunfeldt, ACTA Endocrinol. 61: 561–576, 1969.
Markussen, Prot. Eng. 2:157–166, 1988.
Markussen, Prot. Eng. 1:205–213, 1987.
GammeHoft, Phys. Rev 64: 1321–1378, 1984.

*Primary Examiner*—John Ulm
*Assistant Examiner*—Christine Saoud
*Attorney, Agent, or Firm*—Steve T. Zelson; Elias J. Lambiris

[57] ABSTRACT

The present invention relates to human insulin derivatives having a protracted profile of action in which the A21 and B3 amino acid residues are, independently, any amino acid residue which can be coded for by the genetic code except Lys, Arg and Cys; Phe$^{B1}$ may be deleted; the B30 amino acid residue is (a) a non-codable, lipophilic amino acid having from 10 to 24 carbon atoms in which case an acyl group of a carboxylic acid with up to 5 carbon atoms is bound to the ε-amino group of Lys$^{B29}$; (b) any amino acid residue which can be coded by the genetic code except Lys, Arg and Cys, in which case a lipophilic substituent is bound to the ε-amino group of Lys$^{B29}$; or (c) deleted, in which case a lipophilic substituent is bound to the ε-amino group of Lys$^{B29}$; and any Zn$^{2+}$ complexes thereof; provided that when the B30 amino acid residue is Thr or Ala, the A21 and B3 amino acid residues are both Asn and Phe$^{B1}$ is present, then the insulin derivative is a Zn$^{2+}$ complex.

95 Claims, 3 Drawing Sheets

ACYLATED INSULIN

This application is a continuation-in-part of application Ser. No. 08/190,829 filed Feb. 2, 1994, now abandoned, and of international application Ser. No. PCT/DK94/00347 filed Sep. 16, 1994.

FIELD OF THE INVENTION

The present invention relates to novel human insulin derivatives which are soluble and have a protracted profile of action, to a method of providing such derivatives, to pharmaceutical compositions containing them, and to the use of such insulin derivatives in the treatment of diabetes.

BACKGROUND OF THE INVENTION

Many diabetic patients are treated with multiple daily insulin injections in a regimen comprising one or two daily injections of a protracted insulin to cover the basal requirement supplemented by bolus injections of a rapid acting insulin to cover the requirement related to meals.

Protracted insulin compositions are well known in the art. Thus, one main type of protracted insulin compositions comprises injectable aqueous suspensions of insulin crystals or amorphous insulin. In these compositions, the insulin compounds utilized typically are protamine insulin, zinc insulin or protamiine zinc insulin.

Certain drawbacks are associated with the use of insulin suspensions. Thus, in order to secure an accurate dosing, the insulin particles must be suspended homogeneously by gentle shaking before a defmed volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies (Samuel et al., Studies on the immunogenecity of protamines in humans and experimental animals by means of a micro-complement fixation test, Clin. Exp. Immunol. 33, pp. 252–260 (1978)).

Also, evidence has been found that the protamine-insulin complex is itself immunogenic (Kurtz et al., Circulating IgG antibody to protamine in patients treated with protamine-insulins, Diabetologica 25, pp. 322–324 (1983)). Therefore, with some patients the use of protracted insulin compositions containing protamines must be avoided.

Another type of protracted insulin compositions are solutions having a pH value below physiological pH from which the insulin will precipitate because of the rise in the pH value when the solution is injected. A drawback with these solutions is that the particle size distribution of the precipitate formed in the tissue on injection, and thus the timing of the medication, depends on the blood flow at the injection site and other parameters in a somewhat unpredictable manner. A further drawback is that the solid particles of the insulin may act as a local irritant causing inflammation of the tissue at the site of injection.

WO 91/12817 (Novo Nordisk A/S) discloses protracted, soluble insulin compositions comprising insulin complexes of cobalt(III). The protraction of these complexes is only intermediate and the bioavailability is reduced.

Human insulin has three primary amino groups: the N-terminal group of the A-chain and of the B-chain and the ε-amino group of $Lys^{B29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group. No specifically $N^{\epsilon B29}$-substituted insulins are disclosed.

According to GB Patent No. 1,492,997 (Nat. Res. Dev. Corp.), it has been found that insulin with a carbamyl substitution at $N^{\epsilon B29}$ has an improved profile of hypoglycaemic effect.

JP laid-open patent application No. 1-254699 (Kodama Co., Ltd.) discloses insulin wherein a fattty acid is bound to the amino group of $Phe^{B1}$ or to the ε-amino group of $Lys^{B29}$ or to both of these. The stated purpose of the derivatisation is to obtain a pharmacologically acceptable, stable insulin preparation.

Insulins, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or swine insulin antibodies.

By "insulin derivative" as used herein is meant a compound having a molecular structure similar to that of human insulin including the disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$, and which have insulin activity.

However, there still is a need for protracted injectable insulin compositions which are solutions and contain insulins which stay in solution after injection and possess minimal inflammatory and immunogenic properties.

One object of the present invention is to provide human insulin derivatives, with a protracted profile of action, which are soluble at physiological pH values.

Another object of the present invention is to provide a pharmaceutical composition comprising the human insulin derivatives according to the invention.

It is a further object of the invention to provide a method of making the human insulin derivatives of the invention.

SUMMARY OF THE INVENTION

Surprisingly, it has turned out that certain human insulin derivatives, wherein the ε-amino group of $Lys^{B29}$ has a lipophilic substituent, have a protracted profile of action and are soluble at physiological pH values.

Accordingly, in its broadest aspect, the present invention relates to an insulin derivative having the following sequence:

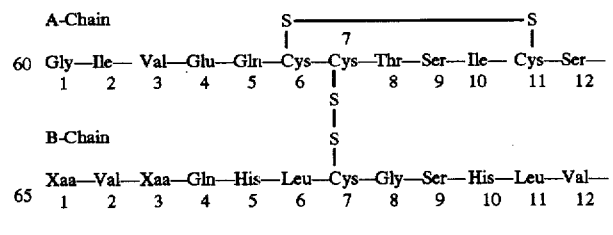

-continued

A-Chain (contd.)

Leu—Tyr—Gln—Leu—Glu—Asn—Tyr—Cys—Xaa  (SEQ ID NO:1)
 13    14   15    16   17   18   19   20   21
                                          |
                                          S
B-Chain (contd.)                          |
                                          S
                                          |
Glu—Ala—Leu—Tyr—Leu—Val—Cys—Gly—Glu—Arg—Gly—Phe—
 13   14   15   16   17   18   19   20   21   22   23   24

B-Chain (contd.)

Phe—Tyr—Thr—Pro—Lys—Xaa  (SEQ ID NO:2)
 25   26   27   28   29   30 wherein

Xaa at positions A21 and B3 are, independently, any amino acid residue which can be coded for by the genetic code except Lys, Arg and Cys;

Xaa at position B1 is Phe or is deleted;

Xaa at position B30 is (a) a non-codable, lipophilic amino acid having from 10 to 24 carbon atoms, in which case an acyl group of a carboxylic acid with up to 5 carbon atoms is bound to the ε-amino group of $Lys^{B29}$, (b) any amino acid residue which can be coded for by the genetic code except Lys, Arg and Cys, in which case the ε-amino group of $Lys^{B29}$ has a lipophilic substituent or (c) deleted, in which case the ε-amino group of $Lys^{B29}$ has a lipophilic substituent; and any $Zn^{2+}$ complexes thereof, provided that when Xaa at position B30 is Thr or Ala, Xaa at positions A21 and B3 are both Asn, and Xaa at position B1 is Phe, then the insulin derivative is a $Zn^{2+}$ complex.

In one preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the ε-amino group of $Lys^{B29}$ has a lipophilic substituent which comprises at least 6 carbon atoms; and 2–4 $Zn^{2+}$ ions may be bound to each insulin hexamer with the proviso that when B30 is Thr or Ala and A21 and B3 are both Asn, and $Phe^{B1}$ is not deleted, then 2–4 $Zn^{2+}$ ions are bound to each hexamer of the insulin derivative.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys, with the proviso that if the B30 amino acid residue is Ala or Thr, then at least one of the residues A21 and B3 is different from Asn; $Phe^{B1}$ may be deleted; and the ε-amino group of $Lys^{B29}$ has a lipophilic substituent which comprises at least 6 carbon atoms.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the ε-amino group of $Lys^{B29}$ has a lipophilic substituent which comprises at least 6 carbon atoms; and 2–4 $Zn^{2+}$ ions are bound to each insulin hexamer.

In another preferred embodiment, the invention relates to a human insulin derivative in which the B30 amino acid residue is deleted.

In another preferred embodiment, the invention relates to a human insulin derivative in which the B30 amino acid residue is Asp.

In another preferred embodiment, the invention relates to a human insulin derivative in which the B30 amino acid residue is Glu.

In another preferred embodiment, the invention relates to a human insulin derivative in which the B30 amino acid residue is Thr.

In another preferred embodiment, the invention relates to a human insulin derivative in which the B30 amino acid is a lipophilic amino acid having at least 10 carbon atoms.

In another preferred embodiment, the invention relates to a human insulin derivative in which the B30 amino acid is a lipophilic α-amino acid having from 10 to 24 carbon atoms.

In another preferred embodiment, the invention relates to a human insulin derivative in which the B30 amino acid is a straight chain, saturated, aliphatic α-amino acid having from 10 to 24 carbon atoms.

In another preferred embodiment, the invention relates to a human insulin derivative in which the B30 amino acid is D- or L-$N^{ε}$-dodecanoyllysine.

In another preferred embodiment, the invention relates to a human insulin derivative in which the B30 amino acid is α-amino decanoic acid.

In another preferred embodiment, the invention relates to a human insulin derivative in which the B30 amino acid is α-amino undecanoic acid.

In another preferred embodiment, the invention relates to a human insulin derivative in which the B30 amino acid is α-amino dodecanoic acid.

In another preferred embodiment, the invention relates to a human insulin derivative in which the B30 amino acid is α-amino tridecanoic acid.

In another preferred embodiment, the invention relates to a human insulin derivative in which the B30 amino acid is α-amino tetradecanoic acid.

In another preferred embodiment, the invention relates to a human insulin derivative in which the B30 amino acid is α-amino pentadecanoic acid.

In another preferred embodiment, the invention relates to a human insulin derivative in which the B30 amino acid is α-amino hexadecanoic acid.

In another preferred embodiment, the invention relates to a human insulin derivative in which the B30 amino acid is an α-amino acid.

In another preferred embodiment, the invention relates to a human insulin derivative in which the A21 amino acid residue is Ala.

In another preferred embodiment, the invention relates to a human insulin derivative in which the A21 amino acid residue is Gln.

In another preferred embodiment, the invention relates to a human insulin derivative in which the A21 amino acid residue is Gly.

In another preferred embodiment, the invention relates to a human insulin derivative in which the A21 amino acid residue is Ser.

In another preferred embodiment, the invention relates to a human insulin derivative in which the B3 amino acid residue is Asp.

In another preferred embodiment, the invention relates to a human insulin derivative in which the B3 amino acid residue is Gln.

In another preferred embodiment, the invention relates to a human insulin derivative in which the B3 amino acid residue is Thr.

In another preferred embodiment, the invention relates to a human insulin derivative in which the ε-amino group of Lys$^{B29}$ has a lipophilic substituent which is an acyl group corresponding to a carboxylic acid having at least 6 carbon atoms.

In another preferred embodiment, the invention relates to a human insulin derivative in which the ε-amino group of Lys$^{B29}$ has a lipophilic substituent which is an acyl group, branched or unbranched, which corresponds to a carboxylic acid having a chain of carbon atoms 8 to 24 atoms long.

In another preferred embodiment, the invention relates to a human insulin derivative in which the ε-amino group of Lys$^{B29}$ has a lipophilic substituent which is an acyl group corresponding to a fatty acid having at least 6 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 6 to 24 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 8 to 12 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 10 to 16 carbon atoms.

In another preferred embodiment, the invention relates to a human insulin derivative in which the ε-amino group of Lys$^{B29}$ has a lipophilic substituent which is an oligo oxyethylene group comprising up to 10, preferably up to 5, oxyethylene units.

In another preferred embodiment, the invention relates to a human insulin derivative in which the ε-amino group of Lys$^{B29}$ has a lipophilic substituent which is an oligo oxypropylene group comprising up to 10, preferably up to 5, oxypropylene units.

In another preferred embodiment, the invention relates to a human insulin derivative in which each insulin hexamer binds 2 Zn$^{2+}$ ions.

In another preferred embodiment, the invention relates to a human insulin derivative in which each insulin hexamer binds 3 Zn$^{2+}$ ions.

In another preferred embodiment, the invention relates to a human insulin derivative in which each insulin hexamer binds 4 Zn$^{2+}$ ions.

In another preferred embodiment, the invention relates to the use of a human insulin derivative according to the invention for the preparation of a medicament for treating diabetes.

In another preferred embodiment, the invention relates to a pharmaceutical composition for the treatment of diabetes in a patient in need of such a treatment comprising a therapeutically effective amount of a human insulin derivative according to the invention together with a pharmaceutically acceptable carrier.

In another preferred embodiment, the invention relates to a pharmaceutical composition for the treatment of diabetes in a patient in need of such a treatment comprising a therapeutically effective amount of a human insulin derivative according to the invention, in mixture with an insulin or an insulin analogue which has a rapid onset of action, together with a pharmaceutically acceptable carrier.

In another preferred embodiment, the invention relates to a pharmaceutical composition comprising a human insulin derivative according to the invention which is soluble at physiological pH values.

In another preferred embodiment, the invention relates to a pharmaceutical composition comprising a human insulin derivative according to the invention which is soluble at pH values in the interval from about 6.5 to about 8.5.

In another preferred embodiment, the invention relates to a protracted pharmaceutical composition comprising a human insulin derivative according to the invention.

In another preferred embodiment, the invention relates to a pharmaceutical composition which is a solution containing from about 120 nmol/ml to about 1200 nmol/ml, preferably about 600 nmol/ml of a human insulin derivative according to the invention.

In another preferred embodiment, the invention relates to a method of treating diabetes in a patient in need of such a treatment comprising administering to the patient a therapeutically effective amount of an insulin derivative according to this invention together with a pharmaceutically acceptable carrier.

In another preferred embodiment, the invention relates to a method of treating diabetes in a patient in need of such a treatment comprising administering to the patient a therapeutically effective amount of an insulin derivative according to this invention, in mixture with an insulin or an insulin analogue which has a rapid onset of action, together with a pharmaceutically acceptable carrier.

Examples of preferred human insulin derivatives according to the present invention in which no Zn$^{2+}$ ions are bound are the following:

N$^{εB29}$-tridecanoyl des(B30) human insulin,
N$^{εB29}$-tetradecanoyl des(B30) human insulin,
N$^{εB29}$-decanoyl des(B30) human insulin,
N$^{εB29}$-dodecanoyl des(B30) human insulin,
N$^{εB29}$-tridecanoyl Gly$^{A21}$ des(B30) human insulin,
N$^{εB29}$-tetradecanoyl Gly$^{A21}$ des(B30) human insulin,
N$^{εB29}$-decanoyl Gly$^{A21}$ des(B30) human insulin,
N$^{εB29}$-dodecanoyl Gly$^{A21}$ des(B30) human insulin,
N$^{εB29}$-tridecanoyl Gly$^{A21}$ Gln$^{B3}$ des(B30) human insulin,
N$^{εB29}$-tetradecanoyl Gly$^{A21}$ Gln$^{B3}$ des(B30) human insulin,
N$^{εB29}$-decanoyl Gly$^{A21}$ Gln$^{B3}$ des(B30) human insulin,
N$^{εB29}$-dodecanoyl Gly$^{A21}$ Gln$^{B3}$ des(B30) human insulin,
N$^{εB29}$-tridecanoyl Ala$^{A21}$ des(B30) human insulin,
N$^{εB29}$-tetradecanoyl Ala$^{A21}$ des(B30) human insulin,
N$^{εB29}$-decanoyl Ala$^{A21}$ des(B30) human insulin,
N$^{εB29}$-dodecanoyl Ala$^{A21}$ des(B30) human insulin,
N$^{εB29}$-tridecanoyl Ala$^{A21}$ Gln$^{B3}$ des(B30) human insulin,
N$^{εB29}$-tetradecanoyl Ala$^{A21}$ Gln$^{B3}$ des(B30) human insulin,
N$^{εB29}$-decanoyl Ala$^{A21}$ Gln$^{B3}$ des(B30) human insulin,
N$^{εB29}$-tridecanoyl Gln$^{B3}$ des(B30) human insulin,
N$^{εB29}$-dodecanoyl Ala$^{A21}$ Gln$^{B3}$ des(B30) human insulin,
εB29-decanoyl Gln$^{B3}$ des(B30) human insulin;
N$^{εB29}$-tetradecanoyl Gln$^{B3}$ des(B30) human insulin,
N$^{εB29}$-dodecanoyl Gln$^{B3}$ des(B30) human insulin,
N$^{εB29}$-tridecanoyl Gly$^{A21}$ human insulin,
N$^{εB29}$-tetradecanoyl Gly$^{A21}$ human insulin,
N$^{εB29}$-decanoyl Gly$^{A21}$ human insulin,
N$^{εB29}$-dodecanoyl Gly$^{A21}$ human insulin,
N$^{εB29}$-tridecanoyl Gly$^{A21}$ Gln$^{B3}$ human insulin,
N$^{εB29}$-tetradecanoyl Gly$^{A21}$ Gln$^{B3}$ human insulin,
N$^{εB29}$-decanoyl Gly$^{A21}$ Gln$^{B3}$ human insulin,
N$^{εB29}$-dodecanoyl Gly$^{A21}$ Gln$^{B3}$ human insulin,
N$^{εB29}$-tridecanoyl Ala$^{A21}$ human insulin,
N$^{εB29}$-tridecanoyl Ala$^{A21}$ human insulin,
N$^{εB29}$-decanoyl Ala$^{A21}$ human insulin,
N$^{εB29}$-dodecanoyl Ala$^{A21}$ human insulin,
N$^{εB29}$-tridecanoyl Ala$^{A21}$ Gln$^{B3}$ human insulin, $N^{\epsilon B29}$-tetradecanoyl Ala$^{A21}$ Gln$^{B3}$ human insulin,
$N^{\epsilon B29}$-decanoyl Ala$^{A21}$ Gln$^{B3}$ human insulin,
$N^{\epsilon B29}$-dodecanoyl Ala$^{A21}$ Gln$^{B3}$ human insulin,
$N^{\epsilon B29}$-tridecanoyl Gln$^{B3}$ human insulin,
$N^{\epsilon B29}$-tetradecanoyl Gln$^{B3}$ human insulin,
$N^{\epsilon B29}$-decanoyl Gln$^{B3}$ human insulin,
$N^{\epsilon B29}$-dodecanoyl Gln$^{B3}$ human insulin,
$N^{\epsilon B29}$-tridecanoyl Gln$^{B30}$ human insulin,
$N^{\epsilon B29}$-tetradecanoyl Gln$^{B30}$ human insulin,
$N^{\epsilon B29}$-decanoyl Gln$^{B30}$ human insulin,
$N^{\epsilon B29}$-dodecanoyl Gln$^{B30}$ human insulin,
$N^{\epsilon B29}$-tridecanoyl Gly$^{A21}$ Glu$^{B30}$ human insulin,
$N^{\epsilon B29}$-tetradecanoyl Gly$^{A21}$ Glu$^{B30}$ human insulin,
$N^{\epsilon B29}$-decanoyl Gly$^{A21}$ Glu$^{B30}$ human insulin,
$N^{\epsilon B29}$-dodecanoyl Gly$^{A21}$ Glu$^{B30}$ human insulin,
$N^{\epsilon B29}$-tridecanoyl Gly$^{A21}$ Gln$^{B3}$ Glu$^{B30}$ human insulin,
$N^{\epsilon B29}$-tetradecanoyl Gly$^{A21}$ Gln$^{B3}$ Glu$^{B30}$ human insulin,
$N^{\epsilon B29}$-decanoyl Gly$^{A21}$ Gln$^{B3}$ Glu$^{B30}$ human insulin,
$N^{\epsilon B29}$-dodecanoyl Gly$^{A21}$ Gln$^{B3}$ Glu$^{B30}$ human insulin,
$N^{\epsilon B29}$-tridecanoyl Ala$^{A21}$ Glu$^{B30}$ human insulin,
$N^{\epsilon B29}$-tetradecanoyl Ala$^{A21}$ Glu$^{B30}$ human insulin,
$N^{\epsilon B29}$-decanoyl Ala$^{A21}$ Glu$^{B30}$ human insulin,
$N^{\epsilon B29}$-dodecanoyl Ala$^{A21}$ Glu$^{B30}$ human insulin,
$N^{\epsilon B29}$-tridecanoyl Ala$^{A21}$ Gln$^{B3}$ Glu$^{B30}$ human insulin,
$N^{\epsilon B29}$-tetradecanoyl Ala$^{A21}$ Gln$^{B3}$ Glu$^{B30}$ human insulin,
$N^{\epsilon B29}$-decanoyl Ala$^{A21}$ Gln$^{B3}$ Glu$^{B30}$ human insulin,
$N^{\epsilon B29}$-dodecanoyl Ala$^{A21}$ Gln$^{B3}$ Glu$^{B30}$ human insulin,
$N^{\epsilon B29}$-tridecanoyl Gln$^{B3}$ Glu$^{B30}$ human insulin,
$N^{\epsilon B29}$-tetradecanoyl Gln$^{B3}$ Glu$^{B30}$ human insulin,
$N^{\epsilon B29}$-decanoyl Gln$^{B3}$ Glu$^{B30}$ human insulin,
$N^{\epsilon B29}$-dodecanoyl Gln$^{B3}$ Glu$^{B30}$ human insulin.

Examples of preferred human insulin derivatives according to the present invention in which Zn$^{2+}$ ions are bound per insulin hexamer are the following:

($N^{\epsilon B29}$-tridecanoyl des(B30) human insulin)$_6$, 2Zn$^{2+}$,
($N^{\epsilon B29}$-tetradecanoyl des(B30) human insulin)$_6$, 2Zn$^{2+}$,
($N^{\epsilon B29}$-decanoyl des(B30) human insulin)$_6$, 2Zn$^{2+}$,
($N^{\epsilon B29}$-dodecanoyl des(B30) human insulin)$_6$, 2Zn$^{2+}$,
($N^{\epsilon B29}$-tridecanoyl Gly$^{A21}$ des(B30) human insulin)$_6$, 2Zn$^{2+}$,
($N^{\epsilon B29}$-tetradecanoyl Gly$^{A21}$ des(B30) human insulin)$_6$, 2Zn$^{2+}$,
($N^{\epsilon B29}$-decanoyl Gly$^{A21}$ des(B30) human insulin)$_6$, 2Zn$^{2+}$,
($N^{\epsilon B29}$-dodecanoyl Gly$^{A21}$ des(B30) human insulin)$_6$, 2Zn$^{2+}$,
($N^{\epsilon B29}$-tridecanoyl Gly$^{A21}$ Gln$^{B3}$ des(B30) human insulin)$_6$, 2Zn$^{2+}$,
($N^{\epsilon B29}$-tetradecanoyl Gly$^{A21}$ Gln$^{B3}$ des(B30) human insulin)$_6$, 2Zn$^{2+}$,
($N^{\epsilon B29}$-decanoyl Gly$^{A21}$ Gln$^{B3}$ des(B30) human insulin)$_6$, 2Zn$^{2+}$,
($N^{\epsilon B29}$-dodecanoyl Gly$^{A21}$ Gln$^{B3}$ des(B30) human insulin)$_6$, 2Zn$^{2+}$,
($N^{\epsilon B29}$-tridecanoyl Ala$^{A21}$ des(B30) human insulin)$_6$, 2Zn$^{2+}$,
($N^{\epsilon B29}$-tetradecanoyl Ala$^{A21}$ des(B30) human insulin)$_6$, 2Zn$^{2+}$,
($N^{\epsilon B29}$-decanoyl Ala$^{A21}$ des(B30) human insulin)$_6$, 2Zn$^{2+}$,
($N^{\epsilon B29}$-dodecanoyl Ala$^{A21}$ des(B30) human insulin)$_6$, 2Zn$^{2+}$,
($N^{\epsilon B29}$-tridecanoyl Ala$^{A21}$ Gln$^{B3}$ des(B30) human insulin)$_6$, 2Zn$^{2+}$,
($N^{\epsilon B29}$-tetradecanoyl Ala$^{A21}$ Gln$^{B3}$ des(B30) human insulin)$_6$, 2Zn$^{2+}$,
($N^{\epsilon B29}$-decanoyl Ala$^{A21}$ Gln$^{B3}$ des(B30) human insulin)$_6$, 2Zn$^{2+}$,
($N^{\epsilon B29}$-dodecanoyl Ala$^{A21}$ Gln$^{B3}$ des(B30) human insulin)$_6$, 2Zn$^{2+}$,
($N^{\epsilon B29}$-tridecanoyl Gln$^{B3}$ des(B30) human insulin)$_6$, 2Zn$^{2+}$,
($N^{\epsilon B29}$-tetradecanoyl Gln$^{B3}$ des(B30) human insulin)$_6$, 2Zn$^{2+}$,
($N^{\epsilon B29}$-decanoyl Gln$^{B3}$ des(B30) human insulin)$_6$, 2Zn$^{2+}$,
($N^{\epsilon B29}$-dodecanoyl Gln$^{B3}$ des(B30) human insulin)$_6$, 2Zn$^{2+}$,
($N^{\epsilon B29}$-tridecanoyl human insulin)$_6$, 2Zn$^{2+}$,
($N^{\epsilon B29}$-tetradecanoyl human insulin)$_6$, 2Zn$^{2+}$,
($N^{\epsilon B29}$-decanoyl human insulin)$_6$, 2Zn$^{2+}$,
($N^{\epsilon B29}$-dodecanoyl human insulin)$_6$, 2Zn$^{2+}$,
($N^{\epsilon B29}$-tridecanoyl Gly$^{A21}$ human insulin)$_6$, 2Zn$^{2+}$,
($N^{\epsilon B29}$-tetradecanoyl Gly$^{A21}$ human insulin)$_6$, 2Zn$^{2+}$,
($N^{\epsilon B29}$-decanoyl Gly$^{A21}$ human insulin)$_6$, 2Zn$^{2+}$,
($N^{\epsilon B29}$-dodecanoyl Gly$^{A21}$ human insulin)$_6$, 2Zn$^{2+}$,
($N^{\epsilon B29}$-tridecanoyl Gly$^{A21}$ Gln$^{B3}$ human insulin)$_6$, 2Zn$^{2+}$,
($N^{\epsilon B29}$-tetradecanoyl Gly$^{A21}$ Gln$^{B3}$ human insulin)$_6$, 2Zn$^{2+}$,
($N^{\epsilon B29}$-decanoyl Gly$^{A21}$ Gln$^{B3}$ human insulin)$_6$, 2Zn$^{2+}$,
($N^{\epsilon B29}$-dodecanoyl Gly$^{A21}$ Gln$^{B3}$ human insulin)$_6$, 2Zn$^{2+}$,
($N^{\epsilon B29}$-tridecanoyl Ala$^{A21}$ human insulin)$_6$, 2Zn$^{2+}$,
($N^{\epsilon B29}$-tetradecanoyl Ala$^{A21}$ human insulin)$_6$, 2Zn$^{2+}$,
($N^{\epsilon B29}$-decanoyl Ala$^{A21}$ human insulin)$_6$, 2Zn$^{2+}$,
($N^{\epsilon B29}$-dodecanoyl Ala$^{A21}$ human insulin)$_6$, 2Zn$^{2+}$,
($N^{\epsilon B29}$-tridecanoyl Ala$^{A21}$ Gln$^{B3}$ human insulin)$_6$, 2Zn$^{2+}$,
($N^{\epsilon B29}$-tetradecanoyl Ala$^{A21}$ Gln$^{B3}$ human insulin)$_6$, 2Zn$^{2+}$,
($N^{\epsilon B29}$-decanoyl Ala$^{A21}$ Gln$^{B3}$ human insulin)$_6$, 2Zn$^{2+}$,
($N^{\epsilon B29}$-dodecanoyl Ala$^{A21}$ Gln$^{B3}$ human insulin)$_6$, 2Zn$^{2+}$,
($N^{\epsilon B29}$-tridecanoyl Gln$^{B3}$ human insulin)$_6$, 2Zn$^{2+}$,
($N^{\epsilon B29}$-tetradecanoyl Gln$^{B3}$ human insulin)$_6$, 2Zn$^{2+}$,
($N^{\epsilon B29}$-decanoyl Gln$^{B3}$ human insulin)$_6$, 2Zn$^{2+}$,
($N^{\epsilon B29}$-dodecanoyl Gln$^{B3}$ human insulin)$_6$, 2Zn$^{2+}$,
($N^{\epsilon B29}$-tridecanoyl Gln$^{B30}$ human insulin)$_6$, 2Zn$^{2+}$,
($N^{\epsilon B29}$-tetradecanoyl Glu$^{B30}$ human insulin)$_6$, 2Zn$^{2+}$,
($N^{\epsilon B29}$-decanoyl Glu$^{B30}$ human insulin)$_6$, 2Zn$^{2+}$,
($N^{\epsilon B29}$-dodecanoyl Glu$^{B30}$ human insulin)$_6$, 2Zn$^{2+}$,
($N^{\epsilon B29}$-tridecanoyl Gly$^{A21}$ Glu$^{B30}$ human insulin)$_6$, 2Zn$^{2+}$,
($N^{\epsilon B29}$-tetradecanoyl Gly$^{A21}$ Glu$^{B30}$ human insulin)$_6$, 2Zn$^{2+}$,
($N^{\epsilon B29}$-decanoyl Gly$^{A21}$ Glu$^{B30}$ human insulin)$_6$, 2Zn$^{2+}$,
($N^{\epsilon B29}$-dodecanoyl Gly$^{A21}$ Glu$^{B30}$ human insulin)$_6$, 2Zn$^{2+}$,
($N^{\epsilon B29}$-tridecanoyl Gly$^{A21}$ Gln$^{B3}$ Glu$^{B30}$ human insulin)$_6$, 2Zn$^{2+}$,
($N^{\epsilon B29}$-tetradecanoyl Gly$^{A21}$ Gln$^{B3}$ Glu$^{B30}$ human insulin)$_6$, 2Zn$^{2+}$,
($N^{\epsilon B29}$-decanoyl Gly$^{A21}$ Gln$^{B3}$ Glu$^{B30}$ human insulin)$_6$, 2Zn$^{2+}$,
($N^{\epsilon B29}$-dodecanoyl Gly$^{A21}$ Gln$^{B3}$ Glu$^{B30}$ human insulin)$_6$, 2Zn$^{2+}$,
($N^{\epsilon B29}$-tridecanoyl Ala$^{A21}$ Glu$^{B30}$ human insulin)$_6$, 2Zn$^{2+}$,
($N^{\epsilon B29}$-tetradecanoyl Ala$^{A21}$ Glu$^{B30}$ human insulin)$_6$, 2Zn$^{2+}$,
($N^{\epsilon B29}$-decanoyl Ala$^{A21}$ Glu$^{B30}$ human insulin)$_6$, 2Zn$^{2+}$,
($N^{\epsilon B29}$-dodecanoyl Ala$^{A21}$ Glu$^{B30}$ human insulin)$_6$, 2Zn$^{2+}$,
($N^{\epsilon B29}$-tridecanoyl Ala$^{A21}$ Gln$^{B3}$ Glu$^{B30}$ human insulin)$_6$, 2Zn$^{2+}$,
($N^{\epsilon B29}$-tetradecanoyl Ala$^{A21}$ Gln$^{B3}$ Glu$^{B30}$ human insulin)$_6$, 2Zn$^{2+}$,
($N^{\epsilon B29}$-decanoyl Ala$^{A21}$ Gln$^{B3}$ Glu$^{B30}$ human insulin)$_6$, 2Zn$^{2+}$,
($N^{\epsilon B29}$-dodecanoyl Ala$^{A21}$ Gln$^{B3}$ Glu$^{B30}$ human insulin)$_6$, 2Zn$^{2+}$,
($N^{\epsilon B29}$-tridecanoyl Gln$^{B3}$ Glu$^{B30}$ human insulin)$_6$, 2Zn$^{2+}$,
($N^{\epsilon B29}$-tetradecanoyl Gln$^{B3}$ Glu$^{B30}$ human insulin)$_6$, 2Zn$^{2+}$,
($N^{\epsilon B29}$-decanoyl Gln$^{B3}$ Glu$^{B30}$ human insulin)$_6$, 2Zn$^{2+}$,
($N^{\epsilon B29}$-dodecanoyl Gln$^{B3}$ Glu$^{B30}$ human insulin)$_6$, 2Zn$^{2+}$, Examples of preferred human insulin derivatives according to the present invention in which three Zn$^{2+}$ ions are bound per insulin hexamer are the following:
($N^{\epsilon B29}$-tridecanoyl des(B30) human insulin)$_6$, 3Zn$^{2+}$,
($N^{\epsilon B29}$-tetradecanoyl des(B30) human insulin)$_6$, 3Zn$^{2+}$,
($N^{\epsilon B29}$-decanoyl des(B30) human insulin)$_6$, 3Zn$^{2+}$,
($N^{\epsilon B29}$-dodecanoyl des(B30) human insulin)$_6$, 3Zn$^{2+}$,
($N^{\epsilon B29}$-tridecanoyl Gly$^{A21}$ des(B30) human insulin)$_6$, 3Zn$^{2+}$,
($N^{\epsilon B29}$-tetradecanoyl Gly$^{A21}$ des(B30) human insulin)$_6$, 3Zn$^{2+}$, ($N^{\epsilon B29}$-decanoyl Gly$^{A21}$ des(B30) human insulin)$_6$, 3Zn$^{2+}$,
($N^{\epsilon B29}$-dodecanoyl Gly$^{A21}$ des(B30) human insulin)$_6$, 3Zn$^{2+}$,
($N^{\epsilon B29}$-tridecanoyl Gly$^{A21}$ Gln$^{B3}$ des(B30) human insulin)$_6$, 3Zn$^{2+}$,
($N^{\epsilon B29}$-tetradecanoyl Gly$^{A21}$ Gln$^{B3}$ des(B30) human insulin)$_6$, 3Zn$^{2+}$,
($N^{\epsilon B29}$-decanoyl Gly$^{A21}$ Gln$^{B3}$ des(B30) human insulin)$_6$, 3Zn$^{2+}$,
($N^{\epsilon B29}$-dodecanoyl Gly$^{A21}$ Gln$^{B3}$ des(B30) human insulin)$_6$, 3Zn$^{2+}$,
($N^{\epsilon B29}$-tridecanoyl Ala$^{A21}$ des(B30) human insulin)$_6$, 3Zn$^{2+}$,
($N^{\epsilon B29}$-tetradecanoyl Ala$^{A21}$ des(B30) human insulin)$_6$, 3Zn$^{2+}$,
($N^{\epsilon B29}$-decanoyl Ala$^{A21}$ des(B30) human insulin)$_6$, 3Zn$^{2+}$,
($N^{\epsilon B29}$-dodecanoyl Ala$^{A21}$ des(B30) human insulin)$_6$, 3Zn$^{2+}$,
($N^{\epsilon B29}$-tridecanoyl Ala$^{A21}$ Gln$^{B3}$ des(B30) human insulin)$_6$, 3Zn$^{2+}$,
($N^{\epsilon B29}$-tetradecanoyl Ala$^{A21}$ Gln$^{B3}$ des(B30) human insulin)$_6$, 3Zn$^{2+}$,
($N^{\epsilon B29}$-decanoyl Ala$^{A21}$ Gln$^{B3}$ des(B30) human insulin)$_6$, 3Zn$^{2+}$,
($N^{\epsilon B29}$-dodecanoyl Ala$^{A21}$ Gln$^{B3}$ des(B30) human insulin)$_6$, 3Zn$^{2+}$,
($N^{\epsilon B29}$-tridecanoyl Gln$^{B3}$ des(B30) human insulin)$_6$, 3Zn$^{2+}$,
($N^{\epsilon B29}$-tetradecanoyl Gln$^{B3}$ des(B30) human insulin)$_6$, 3Zn$^{2+}$,
($N^{\epsilon B29}$-decanoyl Gln$^{B3}$ des(B30) human insulin)$_6$, 3Zn$^{2+}$,
($N^{\epsilon B29}$-dodecanoyl Gln$^{B3}$ des(B30) human insulin)$_6$, 3Zn$^{2+}$,
($N^{\epsilon B29}$-tridecanoyl human insulin)$_6$, 3Zn$^{2+}$,
($N^{\epsilon B29}$-tetradecanoyl human insulin)$_6$, 3Zn$^{2+}$,
($N^{\epsilon B29}$-decanoyl human insulin)$_6$, 3Zn$^{2+}$,
($N^{\epsilon B29}$-dodecanoyl human insulin)$_6$, 3Zn$^{2+}$,
($N^{\epsilon B29}$-tridecanoyl Gly$^{A21}$ human insulin)$_6$, 3Zn$^{2+}$,
($N^{\epsilon B29}$-tetradecanoyl Gly$^{A21}$ human insulin)$_6$, 3Zn$^{2+}$,
($N^{\epsilon B29}$-decanoyl Gly$^{A21}$ human insulin)$_6$, 3Zn$^{2+}$,
($N^{\epsilon B29}$-dodecanoyl Gly$^{A21}$ human insulin)$_6$, 3Zn$^{2+}$,
($N^{\epsilon B29}$-tridecanoyl Gly$^{A21}$ Gln$^{B3}$ human insulin)$_6$, 3Zn$^{2+}$,
($N^{\epsilon B29}$-tetradecanoyl Gly$^{A21}$ Gln$^{B3}$ human insulin)$_6$, 3Zn$^{2+}$,
($N^{\epsilon B29}$-decanoyl Gly$^{A21}$ Gln$^{B3}$ human insulin)$_6$, 3Zn$^{2+}$,
($N^{\epsilon B29}$-dodecanoyl Gly$^{A21}$ Gln$^{B3}$ human insulin)$_6$, 3Zn$^{2+}$,
($N^{\epsilon B29}$-tridecanoyl Ala$^{A21}$ human insulin)$_6$, 3Zn$^{2+}$,
($N^{\epsilon B29}$-tetradecanoyl Ala$^{A21}$ human insulin)$_6$, 3Zn$^{2+}$,
($N^{\epsilon B29}$-decanoyl Ala$^{A21}$ human insulin)$_6$, 3Zn$^{2+}$,
($N^{\epsilon B29}$-dodecanoyl Ala$^{A21}$ human insulin)$_6$, 3Zn$^{2+}$,
($N^{\epsilon B29}$-tridecanoyl Ala$^{A21}$ Gln$^{B3}$ human insulin)$_6$, 3Zn$^{2+}$,
($N^{\epsilon B29}$-tetradecanoyl Ala$^{A21}$ Gln$^{B3}$ human insulin)$_6$, 3Zn$^{2+}$,
($N^{\epsilon B29}$-decanoyl Ala$^{A21}$ Gln$^{B3}$ human insulin)$_6$, 3Zn$^{2+}$,
($N^{\epsilon B29}$-dodecanoyl Ala$^{A21}$ Gln$^{B3}$ human insulin)$_6$, 3Zn$^{2+}$,
($N^{\epsilon B29}$-tridecanoyl Gln$^{B3}$ human insulin)$_6$, 3Zn$^{2+}$,
($N^{\epsilon B29}$-tetradecanoyl Gln$^{B3}$ human insulin)$_6$, 3Zn$^{2+}$,
($N^{\epsilon B29}$-decanoyl Gln$^{B3}$ human insulin)$_6$, 3Zn$^{2+}$,
($N^{\epsilon B29}$-dodecanoyl Gln$^{B3}$ human insulin)$_6$, 3Zn$^{2+}$,
($N^{\epsilon B29}$-tridecanoyl Glu$^{B30}$ human insulin)$_6$, 3Zn$^{2+}$,
($N^{\epsilon B29}$-tetradecanoyl Glu$^{B30}$ human insulin)$_6$, 3Zn$^{2+}$,
($N^{\epsilon B29}$-decanoyl Glu$^{B30}$ human insulin)$_6$, 3Zn$^{2+}$,
($N^{\epsilon B29}$-dodecanoyl Glu$^{B30}$ human insulin)$_6$, 3Zn$^{2+}$,
($N^{\epsilon B29}$-tridecanoyl Gly$^{A21}$ Glu$^{B30}$ human insulin)$_6$, 3Zn$^{2+}$,
($N^{\epsilon B29}$-tetradecanoyl Gly$^{A21}$ Glu$^{B30}$ human insulin)$_6$, 3Zn$^{2+}$,
($N^{\epsilon B29}$-decanoyl Gly$^{A21}$ Glu$^{B30}$ human insulin)$_6$, 3Zn$^{2+}$,
($N^{\epsilon B29}$-dodecanoyl Gly$^{A21}$ Glu$^{B30}$ human insulin)$_6$, 3Zn$^{2+}$,
($N^{\epsilon B29}$-tridecanoyl Gly$^{A21}$ Gln$^{B3}$ Glu$^{B30}$ human insulin)$_6$, 3Zn$^{2+}$,
($N^{\epsilon B29}$-tetradecanoyl Gly$^{A21}$ Gln$^{B3}$ Glu$^{B30}$ human insulin)$_6$, 3Zn$^{2+}$,
($N^{\epsilon B29}$-decanoyl Gly$^{A21}$ Gln$^{B3}$ Glu$^{B30}$ human insulin)$_6$, 3Zn$^{2+}$,
($N^{\epsilon B29}$-dodecanoyl Gly$^{A21}$ Gln$^{B3}$ Glu$^{B30}$ human insulin)$_6$, 3Zn$^{2+}$,
($N^{\epsilon B29}$-tridecanoyl Ala$^{A21}$ Glu$^{B30}$ human insulin)$_6$, 3Zn$^{2+}$,
($N^{\epsilon B29}$-tetradecanoyl Ala$^{A21}$ Glu$^{B30}$ human insulin)$_6$, 3Zn$^{2+}$,
($N^{\epsilon B29}$-decanoyl Ala$^{A21}$ Glu$^{B30}$ human insulin)$_6$, 3Zn$^{2+}$,
($N^{\epsilon B29}$-dodecanoyl Ala$^{A21}$ Glu$^{B30}$ human insulin)$_6$, 3Zn$^{2+}$,
($N^{\epsilon B29}$-tridecanoyl Ala$^{A21}$ Gln$^{B3}$ Glu$^{B30}$ human insulin)$_6$, 3Zn$^{2+}$,
($N^{\epsilon B29}$-tetradecanoyl Ala$^{A21}$ Gln$^{B3}$ Glu$^{B30}$ human insulin)$_6$, 3Zn$^{2+}$,
($N^{\epsilon B29}$-decanoyl Ala$^{A21}$ Gln$^{B3}$ Glu$^{B30}$ human insulin)$_6$, 3Zn$^{2+}$,
($N^{\epsilon B29}$-dodecanoyl Ala$^{A21}$ Gln$^{B3}$ Glu$^{B30}$ human insulin)$_6$, 3Zn$^{2+}$,
($N^{\epsilon B29}$-tridecanoyl Gln$^{B3}$ Glu$^{B30}$ human insulin)$_6$, 3Zn$^{2+}$,
($N^{\epsilon B29}$-tetradecanoyl Gln$^{B3}$ Glu$^{B30}$ human insulin)$_6$, 3Zn$^{2+}$,
($N^{\epsilon B29}$-decanoyl Gln$^{B3}$ Glu$^{B30}$ human insulin)$_6$, 3Zn$^{2+}$,
($N^{\epsilon B29}$-dodecanoyl Gln$^{B3}$ Glu$^{B30}$ human insulin)$_6$, 3Zn$^{2+}$, Examples of preferred human insulin derivatives according to the present invention in which four Zn$^{2+}$ ions are bound per insulin hexamer are the following:
($N^{\epsilon B29}$-tridecanoyl des(B30) human insulin)$_6$, 4Zn$^{2+}$,
($N^{\epsilon B29}$-tetradecanoyl des(B30) human insulin)$_6$, 4Zn$^{2+}$,
($N^{\epsilon B29}$-decanoyl des(B30) human insulin)$_6$, 4Zn$^{2+}$,
($N^{\epsilon B29}$-dodecanoyl des(B30) human insulin)$_6$, 4Zn$^{2+}$,
($N^{\epsilon B29}$-tridecanoyl Gly$^{A21}$ des(B30) human insulin)$_6$, 4Zn$^{2+}$,
($N^{\epsilon B29}$-tetradecanoyl Gly$^{A21}$ des(B30) human insulin)$_6$, 4Zn$^{2+}$,
($N^{\epsilon B29}$-decanoyl Gly$^{A21}$ des(B30) human insulin)$_6$, 4Zn$^{2+}$,
($N^{\epsilon B29}$-dodecanoyl Gly$^{A21}$ des(B30) human insulin)$_6$, 4Zn$^{2+}$,
($N^{\epsilon B29}$-tridecanoyl Gly$^{A21}$ Gln$^{B3}$ des(B30) human insulin)$_6$, 4Zn$^{2+}$,
($N^{\epsilon B29}$-tetradecanoyl Gly$^{A21}$ Gln$^{B3}$ des(B30) human insulin)$_6$, 4Zn$^{2+}$,
($N^{\epsilon B29}$-decanoyl Gly$^{A21}$ Gln$^{B3}$ des(B30) human insulin)$_6$, 4Zn$^{2+}$,
($N^{\epsilon B29}$-dodecanoyl Gly$^{A21}$ Gln$^{B3}$ des(B30) human insulin)$_6$, 4Zn$^{2+}$,
($N^{\epsilon B29}$-tridecanoyl Ala$^{A21}$ des(B30) human insulin)$_6$, 4Zn$^{2+}$,
($N^{\epsilon B29}$-tetradecanoyl Ala$^{A21}$ des(B30) human insulin)$_6$, 4Zn$^{2+}$,
($N^{\epsilon B29}$-decanoyl Ala$^{A21}$ des(B30) human insulin)$_6$, 4Zn$^{2+}$,
($N^{\epsilon B29}$-dodecanoyl Ala$^{A21}$ des(B30) human insulin)$_6$, 4Zn$^{2+}$,
($N^{\epsilon B29}$-tridecanoyl Ala$^{A21}$ Gln$^{B3}$ des(B30) human insulin)$_6$, 4Zn$^{2+}$,
($N^{\epsilon B29}$-tetradecanoyl Ala$^{A21}$ Gln$^{B3}$ des(B30) human insulin)$_6$, 4Zn$^{2+}$,
($N^{\epsilon B29}$-decanoyl Ala$^{A21}$ Gln$^{B3}$ des(B30) human insulin)$_6$, 4Zn$^{2+}$,
($N^{\epsilon B29}$-dodecanoyl Ala$^{A21}$ Gln$^{B3}$ des(B30) human insulin)$_6$, 4Zn$^{2+}$,
($N^{\epsilon B29}$-tridecanoyl Gln$^{B3}$ des(B30) human insulin)$_6$, 4Zn$^{2+}$,
($N^{\epsilon B29}$-tetradecanoyl Gln$^{B3}$ des(B30) human insulin)$_6$, 4Zn$^{2+}$,
($N^{\epsilon B29}$-decanoyl Gln$^{B3}$ des(B30) human insulin)$_6$, 4Zn$^{2+}$,
($N^{\epsilon B29}$-dodecanoyl Gln$^{B3}$ des(B30) human insulin)$_6$, 4Zn$^{2+}$,
($N^{\epsilon B29}$-tridecanoyl human insulin)$_6$, 4Zn$^{2+}$,
($N^{\epsilon B29}$-tetradecanoyl human insulin)$_6$, 4Zn$^{2+}$,
($N^{\epsilon B29}$-decanoyl human insulin)$_6$, 4Zn$^{2+}$,
($N^{\epsilon B29}$-dodecanoyl human insulin)$_6$, 4Zn$^{2+}$,
($N^{\epsilon B29}$-tridecanoyl Gly$^{A21}$ human insulin)$_6$, 4Zn$^{2+}$,
($N^{\epsilon B29}$-tetradecanoyl Gly$^{A21}$ human insulin)$_6$, 4Zn$^{2+}$,
($N^{\epsilon B29}$-decanoyl Gly$^{A21}$ human insulin)$_6$, 4Zn$^{2+}$,
($N^{\epsilon B29}$-dodecanoyl Gly$^{A21}$ human insulin)$_6$, 4Zn$^{2+}$,
($N^{\epsilon B29}$-tridecanoyl Gly$^{A21}$ Gln$^{B3}$ human insulin)$_6$, 4Zn$^{2+}$,
($N^{\epsilon B29}$-tetradecanoyl Gly$^{A21}$ Gln$^{B3}$ human insulin)$_6$, 4Zn$^{2+}$, ($N^{εB29}$-decanoyl Gly$^{A21}$ Gln$^{B3}$ human insulin)$_6$, 4Zn$^{2+}$,
($N^{εB29}$-dodecanoyl Gly$^{A21}$ Gln$^{B3}$ human insulin)$_6$, 4Zn$^{2+}$,
($N^{εB29}$-tridecanoyl Ala$^{A21}$ human insulin)$_6$, 4Zn$^{2+}$,
($N^{εB29}$-tetradecanoyl Ala$^{A21}$ human insulin)$_6$, 4Zn$^{2+}$,
($N^{εB29}$-decanoyl Ala$^{A21}$ human insulin)$_6$, 4Zn$^{2+}$,
($N^{εB29}$-dodecanoyl Ala$^{A21}$ human insulin)$_6$, 4Zn$^{2+}$,
($N^{εB29}$-tridecanoyl Ala$^{A21}$ Gln$^{B3}$ human insulin)$_6$, 4Zn$^{2+}$,
($N^{εB29}$-tetradecanoyl Ala$^{A21}$ Gln$^{B3}$ human insulin)$_6$, 4Zn$^{2+}$,
($N^{εB29}$-decanoyl Ala$^{A21}$ Gln$^{B3}$ human insulin)$_6$, 4Zn$^{2+}$,
($N^{εB29}$-dodecanoyl Ala$^{A21}$ Gln$^{B3}$ human insulin)$_6$, 4Zn$^{2+}$,
($N^{εB29}$-tridecanoyl Gln$^{B3}$ human insulin)$_6$, 4Zn$^{2+}$,
($N^{εB29}$-tetradecanoyl Gln$^{B3}$ human insulin)$_6$, 4Zn$^{2+}$,
($N^{εB29}$-decanoyl Gln$^{B3}$ human insulin)$_6$, 4Zn$^{2+}$,
($N^{εB29}$-dodecanoyl Gln$^{B3}$ human insulin)$_6$, 4Zn$^{2+}$,
($N^{εB29}$-tridecanoyl Glu$^{B30}$ human insulin)$_6$, 4Zn$^{2+}$,
($N^{εB29}$-tetradecanoyl Glu$^{B30}$ human insulin)$_6$, 4Zn$^{2+}$,
($N^{εB29}$-decanoyl Glu$^{B30}$ human insulin)$_6$, 4Zn$^{2+}$,
($N^{εB29}$-dodecanoyl Glu$^{B30}$ human insulin)$_6$, 4Zn$^{2+}$,
($N^{εB29}$-tridecanoyl Gly$^{A21}$ Glu$^{B30}$ human insulin)$_6$, 4Zn$^{2+}$,
($N^{εB29}$-tetradecanoyl Gly$^{A21}$ Glu$^{B30}$ human insulin)$_6$, 4Zn$^{2+}$,
($N^{εB29}$-decanoyl Gly$^{A21}$ Glu$^{B30}$ human insulin)$_6$, 4Zn$^{2+}$,
($N^{εB29}$-dodecanoyl Gly$^{A21}$ Glu$^{B30}$ human insulin)$_6$, 4Zn$^{2+}$,
($N^{εB29}$-tridecanoyl Gly$^{A21}$ Gln$^{B3}$ Glu$^{B30}$ human insulin)$_6$, 4Zn$^{2+}$,
($N^{εB29}$-tetradecanoyl Gly$^{A21}$ Gln$^{B3}$ Glu$^{B30}$ human insulin)$_6$, 4Zn$^{2+}$,
($N^{εB29}$-decanoyl Gly$^{A21}$ Gln$^{B3}$ Glu$^{B30}$ human insulin)$_6$, 4Zn$^{2+}$,
($N^{εB29}$-dodecanoyl Gly$^{A21}$ Gln$^{B3}$ Glu$^{B30}$ human insulin)$_6$, 4Zn$^{2+}$,
($N^{εB29}$-tridecanoyl Ala$^{A21}$ Glu$^{B30}$ human insulin)$_6$, 4Zn$^{2+}$,
($N^{εB29}$-tetradecanoyl Ala$^{A21}$ Glu$^{B30}$ human insulin)$_6$, 4Zn$^{2+}$,
($N^{εB29}$-decanoyl Ala$^{A21}$ Glu$^{B30}$ human insulin)$_6$, 4Zn$^{2+}$,
($N^{εB29}$-dodecanoyl Ala$^{A21}$ Glu$^{B30}$ human insulin)$_6$, 4Zn$^{2+}$,
($N^{εB29}$-tridecanoyl Ala$^{A21}$ Gln$^{B3}$ Glu$^{B30}$ human insulin)$_6$, 4Zn$^{2+}$,
($N^{εB29}$-tetradecanoyl Ala$^{A21}$ Gln$^{B3}$ Glu$^{B30}$ human insulin)$_6$, 4Zn$^{2+}$,
($N^{εB29}$-decanoyl Ala$^{A21}$ Gln$^{B3}$ Glu$^{B30}$ human insulin)$_6$, 4Zn$^{2+}$,
($N^{εB29}$-dodecanoyl Ala$^{A21}$ Gln$^{B3}$ Glu$^{B30}$ human insulin)$_6$, 4Zn$^{2+}$,
($N^{εB29}$-tridecanoyl Gln$^{B3}$ Glu$^{B30}$ human insulin)$_6$, 4Zn$^{2+}$,
($N^{εB29}$-tetradecanoyl Gln$^{B3}$ Glu$^{B30}$ human insulin)$_6$, 4Zn$^{2+}$,
($N^{εB29}$-decanoyl Gln$^{B3}$ Glu$^{B30}$ human insulin)$_6$, 4Zn$^{2+}$,
($N^{εB29}$-dodecanoyl Gln$^{B3}$ Glu$^{B30}$ human insulin)$_6$, 4Zn$^{2+}$,

BRIEF DESCRIPTION OF THE DRAWINGS

The present invention is further illustrated with reference to the appended drawings wherein.

DETAILED DESCRIPTION OF THE INVENTION

Terminology

Figure 1:
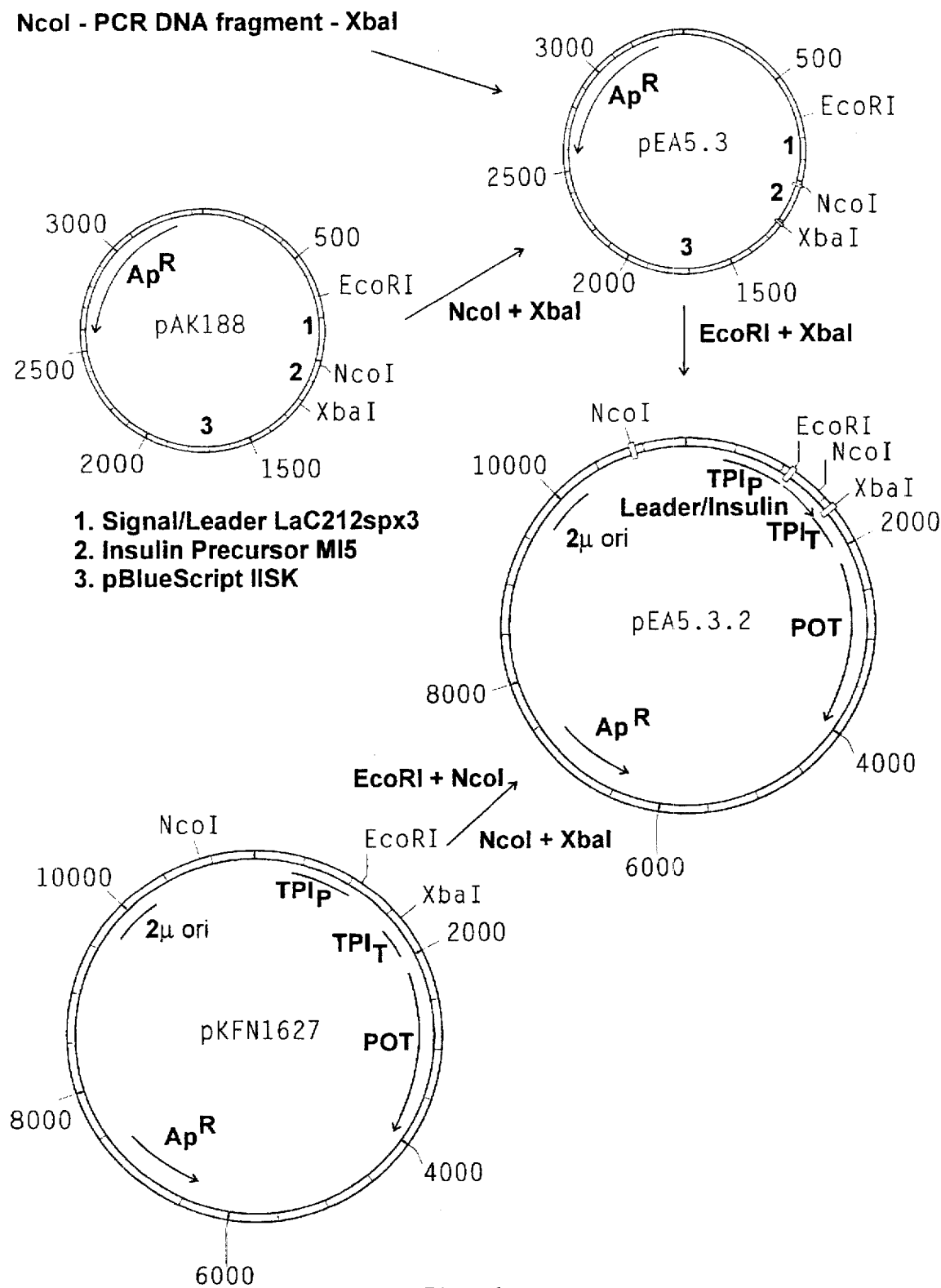
FIG. 1 shows the construction of the plasmid pEA5.3.2.

The three letter codes and one letter codes for the amino acid residues used herein are those stated in J. Biol. Chem. 243, p. 3558 (1968).

In the DNA sequences, A is adenine, C is cytosine, G is guanine, and T is thymine.

The following acronyms are used:
DMSO for dimethyl sulphoxide, DMF for dimethylformamide, Boc for tert-butoxycarbonyl,
RP-BPLC for reversed phase high performance liquid chromatography, X-OSu is an N-hydroxysuccinimid ester, X is an acyl group, and TFA for trifluoroacetic acid.

Preparation of lipophilic insulin derivatives

The insulin derivatives according to the present invention can be prepared i.a. as described in the following:

1. Insulin derivatives featuring in position B30 an amino acid residue which can be coded for by the genetic code e.g. threonine (human insulin) or alanine (porcine insulin).

1.1 Starting from human insulin.

Human insulin is treated with a Boc-reagent (e.g. di-tert-butyl dicarbonate) to form (A1,B1)-diBoc human insulin, i.e., human insulin in which the N-terminal end of both are protected by a Boc-group. After an optional purification, e.g. by HPLC, an acyl group is introduced in the ε-amino group of Lys$^{B29}$ by allowing the product to react with a N-hydroxysuccinimide ester of the formula X-OSu wherein X is the acyl group to be introduced. In the final step, TFA is used to remove the Boc-groups and the product, $N^{εB29}$-X human insulin, is isolated.

1.2 Starting from a single chain insulin precursor.

A single chain insulin precursor, extended in position B1 with an extension (Ext) which is connected to BI via an arginine residue and in which the bridge from B30 to A1 is an arginine residue, i.e. a compound of the general formula Ext-Arg-B(1–30)-Arg-A(1–21), can be used as starting material. Acylation of this starting material with a N-hydroxysuccinimide ester of the general formula X-OSu wherein X is an acyl group, introduces the acyl group X in the ε-amino group of Ly$_{B29}$ and in the N-terminal amino group of the precursor. On treating this acylated precursor of the formula ($N^{εB29}$-X),X-ExtArg-B(1–30)-Arg-A(1–21) with trypsin in a mixture of water and a suitable water-miscible organic solvent, e.g. DMF, DMSO or a lower alcohol, an intermediate of the formula ($N^{εB29}$-X).Arg$^{B33}$ insulin is obtained. Treating this intermediate with carboxypeptidase B yields the desired product, ($N^{εB29}$-X) insulin.

2. Insulin derivatives with no amino acid residue in position B30, i.e. des(B30) insulins.

2.1 Starting from human insulin or porcine insulin.

On treatment with carboxypeptidase A in ammonium buffer, human insulin and porcine insulin both yield des (B30) insulin. After an optional purification, the des(B30) insulin is treated with a Boc-reagent (e.g. di-tert-butyl dicarbonate) to form (A1,B1)-diBoc des(B30) insulin, i.e., des(B30) insulin in which the N-terminal end of both chains are protected by a Boc-group. After an optional purification, e.g. by HPLC, an acyl group is introduced in the ε-amino group of Lys$^{B29}$ by allowing the product to react with a N-hydroxysuccinimide ester of the formula X-OSu wherein X is the acyl group to be introduced. In the final step, TFA is used to remove the Boc-groups and the product, ($N^{εB29}$-X) des(B30) insulin, is isolated.

2.2 Starting from a single chain human insulin precursor.

A single chain human insulin precursor, which is extended in position B1 with an extension (Ext) which is connected to B1 via an arginine residue and which has a bridge from B30 to A1 can be a useful starting material. Preferably, the bridge is a peptide of the formula Y$_n$-Arg, where Y is a codable amino acid except lysine and arginine, and n is zero or an integer between 1 and 35. When n>1, the Y's may designate different amino acids. Preferred examples of the bridge from B30 to A1 are: AlaAlaArg, SerArg, SerAspAspAlaArg and Arg (European Patent No. 163529). Treatment of such a precursor of the general formula Ext-Arg-B(1–30)-Y$_n$-Arg-A(1–21) with a lysyl endopeptidase, e.g. *Achromobacter*

*lyticus* protease, yields Ext-Arg-B(1–29) Thr-$Y_n$-Arg-A (1–21) des(B30) insulin. Acylation of this intermediate with a N-hydroxysuccinimide ester of the general formula X-OSu wherein X is an acyl group, introduces the acyl group X in the ε-amino group of $Lys^{B29}$, and in the N-terminal amino group of the A-chain and the B-chain to give ($N^{\epsilon B29}$-X) X-Ext-Arg-B(1–29) X-Thr-$Y_n$-Arg-A(1–21) des(B30) insulin. This intermediate on treatment with trypsin in mixture of water and a suitable organic solvent, e.g. DMF, DMSO or a lower alcohol, gives the desired derivative, ($N^{\epsilon B29}$-X) des (B30) human insulin.

Data on $N^{\epsilon B29}$ modified insulins.

Certain experimental data on $N^{\epsilon B29}$ modified insulins are given in Table 1.

The lipophilicity of an insulin derivative relative to human insulin, k'$_{rel}$, was measured on a LiChrosorb RP18 (5 μm, 250×4 mm) HPLC column by isocratic elution at 40° C. using mixtures of A) 0.1M sodium phosphate buffer, pH 7.3, containing 10% acetonitrile, and B) 50% acetonitrile in water as eluents. The elution was monitored by following the UV absorption of the eluate at 214 nm. Void time, $t_o$, was found by injecting 0.1 mM sodium nitrate. Retention time for human insulin, $t_{human}$, was adjusted to at least $2t_o$ by varying the ratio between the A and B solutions. k'$_{rel}$= ($t_{derivative}$-$t_o$)/($t_{human}$-$t_o$).

The degree of prolongation of the blood glucose lowering effect was studied in rabbits. Each insulin derivative was tested by subcutaneous injection of 12 nmol thereof in each of six rabbits in the single day retardation test. Blood sampling for glucose analysis was performed before injection and at 1, 2, 4 and 6 hours after injection. The glucose values found are expressed as percent of initial values. The Index of Protraction, which was calculated from the blood glucose values, is the scaled Index of Protraction (prolongation), see p. 211 in Markussen et al., Protein Engineering 1 (1987) 205–213. The formula has been scaled to render a value of 100 with bovine ultralente insulin and a value of 0 with Actrapid® insulin (Novo Nordisk A/S, 2880 Bagsvaerd, Denmark).

The insulin derivatives listed in Table 1 were administered in solutions containing 3 $Zn^{2+}$ per insulin hexamer, except those specifically indicated to be Zn-free.

For the very protracted analogues the rabbit model is inadequate because the decrease in blood glucose from initial is too small to estimate the index of protraction. The prolongation of such analogues is better characterized by the disappearance rate in pigs. $T_{50\%}$ is the time when 50% of the A14 Tyr($^{125}$I) analogue has disappeared from the site of injection as measured with an external γ-counter (Ribel, U et al., The Pig as a Model for Subcutaneous Absorption in Man. In: M. serrano-Rios and P.J. Lefebre (Eds): Diabetes 1985; Proceedings of the 12th Congress of the International Diabetes Federation, Madrid, Spain, 1985 (Excerpta Medica, Amsterdam, (1986) 891–96).

In Table 2 are given the $T_{50\%}$ values of a series of very protracted insulin analogues. The analogues were administered in solutions containing 3 $Zn^{2+}$ per insulin hexamer.

TABLE 1

| Insulin Derivative *) | Relative Lipophilicity | Blood glucose, % of initial | | | | Index of protraction |
|---|---|---|---|---|---|---|
| | | 1 h | 2 h | 4 h | 6 h | |
| $N^{\epsilon B29}$-benzoyl insulin | 1.14 | | | | | |
| $N^{\epsilon B29}$-phenylacetyl insulin (Zn-free) | 1.28 | 55.4 | 58.9 | 88.8 | 90.1 | 10 |
| $N^{\epsilon B29}$-cyclohexylacetyl insulin | 1.90 | 53.1 | 49.6 | 66.9 | 81.1 | 28 |
| $N^{\epsilon B29}$-cyclohexylpropionyl insulin | 3.29 | 55.5 | 47.6 | 61.5 | 73.0 | 39 |
| $N^{\epsilon B29}$-cyclohexylvaleroyl insulin | 9.87 | 65.0 | 58.3 | 65.7 | 71.0 | 49 |
| $N^{\epsilon B29}$-octanoyl insulin | 3.97 | 57.1 | 54.8 | 69.0 | 78.9 | 33 |
| $N^{\epsilon B29}$-decanoyl, des (B30) insulin | 11.0 | 74.3 | 65.0 | 60.9 | 64.1 | 65 |
| $N^{\epsilon B29}$-decanoyl insulin | 12.3 | 73.3 | 59.4 | 64.9 | 68.0 | 60 |
| $N^{\epsilon B29}$-undecanoyl, des (B30) insulin | 19.7 | 88.1 | 80.0 | 72.1 | 72.1 | 80 |
| $N^{\epsilon B29}$-lauroyl, des (B30) insulin | 37.0 | 91.4 | 90.0 | 84.2 | 83.9 | 78 |
| $N^{\epsilon B29}$-myristoyl insulin | 113 | 98.5 | 92.0 | 83.9 | 84.5 | 97 |
| $N^{\epsilon B29}$-choloyl insulin | 7.64 | 58.2 | 53.2 | 69.0 | 88.5 | 20 |
| $N^{\epsilon B29}$-7-deoxycholoyl insulin (Zn-free) | 24.4 | 76.5 | 65.2 | 77.4 | 87.4 | 35 |
| $N^{\epsilon B29}$-lithocholoyl insulin (Zn-free) | 51.6 | 98.3 | 92.3 | 100.5 | 93.4 | 115 |
| $N^{\epsilon B29}$-4-benzoyl-phenylalanyl insulin | 2.51 | 53.9 | 58.7 | 74.4 | 89.0 | 14 |
| $N^{\epsilon B29}$-3,5-diiodotyrosyl insulin | 1.07 | 53.9 | 48.3 | 60.8 | 82.1 | 27 |
| $N^{\epsilon B29}$-L-thyroxyl insulin | 8.00 | | | | | |

TABLE 2

| Derivative of Human Insulin | Relative hydrophobicity | Subcutaneous disappearance in pigs |
|---|---|---|
| 600 μM, 3 $Zn^{2+}$/hexamer, phenol 0.3%, glycerol 1.6%, pH 7.5 | k'$_{rel}$ | $T_{50\%}$, hours |
| $N^{\epsilon B29}$-decanoyl des (B30) insulin | 11.0 | 5.6 |
| $N^{\epsilon B29}$-undecanoyl des (B30) insulin | 19.7 | 6.9 |
| $N^{\epsilon B29}$-lauroyl des (B30) insulin | 37 | 10.1 |
| $N^{\epsilon B29}$-tridecanoyl des (B30) insulin | 65 | 12.9 |
| $N^{\epsilon B29}$-myristoyl des (B30) insulin | 113 | 13.8 |
| $N^{\epsilon B29}$-palmitoyl des (B30) insulin | 346 | 12.4 |
| $N^{\epsilon B29}$-2-succinyl-amido myristic acid insulin | 10.5 | 13.6 |
| $N^{\epsilon B29}$-myristoyl insulin | 113 | 11.9 |
| $N^{\epsilon B29}$-2-succinyl-amido palmitic acid insulin | 420 | 20.1 |
| $N^{\epsilon B29}$-myristoyl-α-glutamyl des (B30) insulin | 23.7 | 8.8 |

TABLE 2-continued

| Derivative of Human Insulin | Relative hydrophobicity | Subcutaneous disappearance in pigs |
|---|---|---|
| $N^{\epsilon B29}$-myristoyl-α-glutamyl-glycyl des (B30) insulin | 20.0 | 11.9 |
| $N^{\epsilon B29}$-lithocholoyl-α-glutamyl des (B30) insulin | 12.5 | 14.3 |
| Human NPH | | 10 |

Solubility

The solubility of all the $N^{\epsilon B29}$ modified insulins mentioned in Table 1, which contain 3 $Zn^{2+}$ ions per insulin hexamer, exceeds 600 nmol/ml in a neutral (pH 7.5), aqueous, pharmaceutical formulation which further comprises 0.3% phenol as preservative, and 1.6% glycerol to achieve isotonicity. 600 nmol/ml is the concentration of human insulin found in the 100 IU/ml compositions usually employed in the clinic.

The ε-B29 amino group can be a component of an amide bond, a sulphonamide bond, a carbamide, a thiocarbamide, or a carbamate. The lipophilic substituent carried by the ε-B29 amino group can also be an alkyl group.

Pharmaceutical compositions containing a human insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the human insulin derivative in the form of a nasal spray.

The injectable human insulin compositions of the invention can be prepared using the conventional techniques of the pharmaceutical industry which involves dissolving and mixing the ingredients as appropriate to give the desired end product.

Thus, according to one procedure, the human insulin derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

A composition for nasal administration of an insulin derivative according to the present invention may, for example, be prepared as described in European Patent No. 272097 (to Novo Nordisk A/S).

The insulin compositions of this invention can be used in the treatment of diabetes. The optimal dose level for any patient will depend on a variety of factors including the efficacy of the specific human insulin derivative employed, the age, body weight, physical activity, and diet of the patient, on a possible combination with other drugs, and on the severity of the case of diabetes. It is recommended that the daily dosage of the human insulin derivative of this invention be determined for each individual patient by those skilled in the art in a similar way as for known insulin compositions.

Where expedient, the human insulin derivatives of this invention may be used in mixture with other types of insulin, e.g. human insulin or porcine insulin or insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Plasmids and DNA material

All expression plasmids are of the cPOT type. Such plasmids are described in EP patent application No. 171 142 and are characterized in containing the *Schizosaccharomyces pombe* triose phosphate isomerase gene (POT) for the purpose of plasmid selection and stabilization. A plasmid containing the POT-gene is available from a deposited *E. coli* strain (ATCC 39685). The plasmids furthermore contain the *S. cerevisiae* triose phosphate isomerase promoter and terminator ($P_{TPI}$ and $T_{TPI}$). They are identical to pMT742 (Egel-Mitani, M. et al., Gene 73 (1988) 113–120) (see FIG. 1) except for the region defined by the ECoRI-XbaI restriction sites encompassing the coding region for signal/leader/product.

Synthetic DNA fragments were synthesized on an automatic DNA synthesizer (Applied Biosystems model 380A) using phosphoramidite chemistry and commercially available reagents (Beaucage, S. L. and Caruthers, M. H., *Tetrahedron Letters* 22 (1981) 1859–1869).

All other methods and materials used are common state of the art knowledge (see, e.g. Sambrook, J., Fritsch, E. F. and Maniatis, T., *Molecular Cloning: A Laboratory Manual*, Cold Spring Harbor Laboratory Press, New York, 1989).

Analytical

Molecular masses of the insulins prepared were obtained by MS (mass spectroscopy), either by PDMS (plasma desorption mass spectrometry) using a Bio-Ion 20 instrument (Bio-Ion Nordic AB, Uppsala, Sweden) or by ESMS (electrospray mass spectrometry) using an API III Biomolecular Mass Analyzer (Perkin-Elmer Sciex Instruments, Thornhill, Canada).

EXAMPLE 1

Synthesis of $Ala^{A21}$ $Asp^{B3}$ human insulin precursor from Yeast strain yEA002 using the LaC212spx3 signal/leader. The following oligonucleotides were synthesized:

98  5' - TGGCTAAGAGATTCGTTGACCAACACTTGTGCGGTTCTCA
     CTTGGTTGAAGCTTTGTACTTGGTTTGTGGTGAA
     AGAGGTTTCTTCTACACTCCAAAGTCTGACGACGCT - 3'  (Asp$^{B3}$)
     (SEQ ID NO:3)

128 5' - CTGCGGGCTGCGTCTAAGCACAGTAGTTTTCCAATTGGTACAA
     AGAACAGATAGAAGTACAACATTGTTCAACGATACCCTTAGCGTC
     GTCAGACTTTGG - 3'  (Ala$^{A21}$)  (SEQ ID NO:4)

126 5' - GTCGCCATGGCTAAGAGATTCGTTG - 3'          (Asp$^{B3}$)
     (SEQ ID NO:5)

16  5' - CTGCTCTAGAGCCTGCGGGCTGCGTCT - 3'  (SEQ ID NO:6)

The following Polymerase Chain Reaction (PCR) was performed using the Gene Amp PCR reagent kit (Perkin Elmer, 761 Main Avewalk, CT 06859, USA) according to the manufacturer's instructions. In all cases, the PCR mixture was overlayed with 100 µl of mineral oil (Sigma Chemical Co., St. Louis, Mo., USA).

2.5 µl of oligonucleotide #98 (2.5 pmol)
2.5 µl of oligonucleotide #128 (2.5 pmol)
10 µl of 10X PCR buffer
16 µl of dNTP mix
0.5 µl of Taq enzyme
58.5 µl of water One cycle was performed: 94° C. for 45 sec., 49° C. for 1 min, 72° C. for 2 min.

Subsequently, 5 µl of oligonucleotides #16 and #126 was added and 15 cycles were performed: 94° C. for 45 sec., 45° C. for 1 min, 72° C. for 1.5 min. The PCR mixture was loaded onto a 2.5% agarose gel and subjected to electrophoresis using standard techniques (Sambrook et al., Molecular cloning, Cold Spring Harbour Laboratory Press, 1989). The resulting DNA fragment was cut out of the agarose gel and isolated using the Gene Clean Kit (Bio 101 Inc., PO BOX 2284, La Jolla, Calif. 92038, USA) according to the manufacturer's instructions. The purified PCR DNA fragment was dissolved in 10 µl of water and restriction endonuclease buffer and cut with the restriction endonucleases NcoI and Xba I according to standard techniques, run on a 2.5% agarose gel and purified using the Gene Clean Kit as described.

The plasmid pAK188 consists of a DNA sequence of 412 bp composed of a EcoRI/NcoI fragment encoding the synthetic yeast signal/leader gene LaC212spx3 (described in Example 3 of WO 89/02463) followed by a synthetic NcoI/XbaI fragment encoding the insulin precursor MI5, which has a SerAspAspAlaLys bridge connecting the B29 and the A1 amino acid residues (see SEQ ID NOS. 14, 15 and 16), inserted into the EcoRI/XbaI fragment of the vector (phagemid) pBLUESCRIPT IIsk(+/−) (Stratagene, USA). The plasmid pAK188 is shown in FIG. 1.

The plasmid pAK188 was also cut with the restriction endonucleases NcoI and XbaI and the vector fragment of 3139 bp isolated. The two DNA fragments were ligated together using T4 DNA ligase and standard conditions (Sambrook et al., Molecular Cloning, Cold Spring Harbour Laboratory Press, 1989). The ligation mixture was transformed into a competent E. coli strain (R−, M+) followed by selection for ampicillin resistance. Plasmids were isolated from the resulting E. coli colonies using standard DNA miliprep technique (Sambrook et al., Molecular Cloning, Cold Spring Harbour Laboratory Press, 1989), checked with appropriate restrictions endonucleases i.e. EcoRI, Xba I, NcoI and HpaI. The selected plasmid was shown by DNA sequencing analyses (Sequenase, U.S. Biochemical Corp.) to contain the correct sequence for the Ala$^{A21}$, Asp$^{B3}$ human insulin precursor and named pEA5.3.

The plasmid pKFN1627 is an E. coli—S. cerevisiae shuttle vector, identical to plasmid pKFN1003 described in EP patent No. 375718, except for a short DNA sequence upstream from the unique XbaI site. In pKFN1003, this sequence is a 178 bp fragment encoding a synthetic aprotinin gene fused in-frame to the yeast mating factor alpha 1 signal-leader sequence. In pKFN1627, the corresponding 184 bp sequence encodes the insulin precursor MI5 (Glu$^{B1}$, Glu$^{B28}$) (i.e. B(1−29, Glu$^{B1}$,Glu$^{B28}$)-SerAspAspAlaLys-A (1−21) fused in-frame to the mating factor alpha 1 sequence (see SEQ ID NOS. 17, 18 and 19). The vector pKFN1627 is shown in FIG. 1.

pEA5.3 was cut with the restriction endonucleases EcoRI and XbaI and the resulting DNA fragment of 412 bp was isolated. The yeast expression vector pKFN1627 was cut with the restriction endonucleases NcoI and XbaI and with NcoI and EcoRI and the DNA fragment of 9273 bp was isolated from the first digestion and the DNA fragment of 1644 bp was isolated from the second. The 412 bp EcoR-WXbaI fragment was then ligated to the two other fragments, that is the 9273 bp NcoI I/XbaI fragment and the 1644 bp NcoI/EcoRI fragment using standard techniques.

The ligation mixture was transformed into E. coli as described above. Plasmid from the resulting E. coli was isolated using standard techniques, and checked with appropriate restriction endonucleases i.e. EcoRI, XbaI, NcoI, Hpa I. The selected plasmid was shown by DNA sequence analysis (using the Sequenase kit as described by the manufacturer, U.S. Biochemical) to contain the correct sequence for the Ala$^{A21}$ Asp$^{B3}$ human insulin precursor DNA and to be inserted after the DNA encoding the LaC212spx3 signalleader DNA. The plasmid was named pEA5.3.2 and is shown in FIG. 1. The DNA sequence encoding the LaC212spx3 signal/leader/Ala$^{A21}$ Asp$^{B3}$ human insulin precursor complex and the amino acid sequence thereof are SEQ D NOS. 20, 21 and 22. The plasmid pEA5.3.2 was transformed into S. cerevisiae strain MT663 as described in European patent application having the publication No. 214826 and the resulting strain was named yEA002.

EXAMPLE 2

Synthesis of Ala$^{A21}$ Thr$^{B3}$ human insulin precursor from Yeast strain yEA005 using the LaC212spx3 signal/leader.

101 5'-TGGCTAAGAGATTCGTTACTCAACACTTGTGCGGTTCTCACTT
GGTTGAAGCTTTGTACTTGGTTTGTGGTGAAAGAGGTTTCTTCTACA
CTCCAAAGTCTGACGACGCT-3'  (Thr$^{B3}$)  (SEQ ID NO:7)

128 5'-CTGCGGGCTGCGTCTAAGCACAGTAGTTTTCCAATTGGTACAAA
TCAGACTTTGG-3'  (Ala$^{A21}$)  (SEQ ID NO:4)

15  5'-GTCGCCATGGCTAAGAGATTCGTTA-3'  (Thr$^{B3}$)  (SEQ ID NO:8)

16  5'-CTGCTCTAGAGCCTGCGGGCTGCGTCT-3'  (SEQ ID NO:6)

The DNA encoding Ala$^{A21}$ Thr$^{B3}$ human insulin precursor was constructed in the same manner as described for the DNA encoding Ala$^{A21}$ Asp$^{B3}$ human insulin precursor in Example 1. The DNA sequence encoding the LaC212spx3 signal/leader/Ala$^{A21}$ Thr$^{B3}$ human insulin precursor complex and the amino acid sequence thereof are SEQ ID NOS. 23, 24 and 25. The plasmid pEA8.1.1 was shown to contain the desired sequence, transformed into *S. cerevisiae* strain MT663 as described in Example 1 and the resulting strain was named yEA005.

EXAMPLE 3

Synthesis of Gly$^{A21}$ Asp$^{B3}$ human insulin precursor from Yeast strain yEA007 using the LaC212spx3 signal/leader.

The following oligonucleotides were synthesized:

98  5'-TGGCTAAGAGATTCGTTGACCAACACTTGTGCGGTTCTCACTTG
GTTGAAGCTTTGTACTTGGTTTGTGGTGAAAGAGGTTTCTTCT
ACACTCCAAAGTCTGACGACGCT-3'  (Asp$^{B3}$)  (SEQ ID NO:3)

127 5'-CTGCGGGCTGCGTCTAACCACAGTAGTTTTCCAATTGGTACAA
AGAACAGATAGAAGTACAACATTGTTCAACGATACCCT
TAGCGTCGTCAGACTTTGG-3'  (Gly$^{A21}$)  (SEQ ID NO:9)

126 5'-GTCGCCATGGCTAAGAGATTCGTTG-3'  (Asp$^{B3}$)  (SEQ ID NO:5)

16  5'-CTGCTCTAGAGCCTGCGGGCTGCGTCT-3'  (SEQ ID NO:6)

The DNA encoding Gly$^{A21}$ Asp$^{B3}$ human insulin precursor was constructed in the same manner as described for the DNA encoding Ala$^{A21}$ Asp$^{B3}$ human insulin precursor in Example 1. The DNA sequence encoding the LaC212spx3 signal/leader/Gly$^{A21}$ Asp$^{B3}$ human insulin precursor complex and the amino acid sequence thereof are SEQ ID NOS. 26, 27 and 28. The plasmid pEA1.5.6 was shown to contain the desired sequence, transformed into *S. cerevisiae* strain MT663 as described in Example 1 and the resulting strain was named yEA007.

EXAMPLE 4

Synthesis of Gly$^{A21}$ Thr$^{B3}$ human insulin precursor from Yeast strain yEA006 using the LaC212spx3 signal/leader.

The following oligonucleotides were synthesized:

101 5'-TGGCTAAGAGATTCGTTACTCAACACTTGTGCGGTTCTCACTT
GGTTGAAGCTTTGTACTTGGTTTGTGGTGAAAGAGGTTTCTTCTACA
CTCCAAAGTCTGACGACGCT-3'  (Thr$^{B3}$)  (SEQ ID:7)

127 5'-CTGCGGGCTGCGTCTAACCACAGTAGTTTTCCAATTGGTACAA
AGAACAGATAGAAGTACAACATTGTTCAACGATACCCT
TAGCGTCGTCAGACTTTGG-3'  (Gly$^{A21}$)  (SEQ ID NO:9)

15  5'-GTCGCCATGGCTAAGAGATTCGTTA-3'  (Thr$^{B3}$)  (SEQ ID NO:8)

16  5'-CTGCTCTAGAGCCTGCGGGCTGCGTCT-3'  (SEQ ID NO:6)

The DNA encoding Gly$^{A21}$ Thr$^{B3}$ human insulin precursor was constructed in the same manner as described for the DNA encoding Ala$^{A21}$ Asp$^{B3}$ human insulin precursor in Example 1. The DNA sequence encoding the LaC212spx3 signal/leader/Gly$^{A21}$ Thr$^{B3}$ human insulin precursor complex and the amino acid sequence thereof are SEQ ID NOS. 29, 30 and 31. The plasmid pEA4.4.11 was shown to contain the desired DNA sequence, transformed into *S. cerevisiae* strain MT663 as described in Example 1 and the resulting strain was named yEA006.

EXAMPLE 5

Synthesis of Arg$^{B-1}$ Arg$^{B31}$ single chain human insulin precursor having an N-terminal extension (GluGluAlaGluAlaGluAlaArg) from Yeast strain yEA113 using the alpha factor leader.

A) The following oligonucleotides were synthesized:

```
#220  5'-ACGTACGTTCTAGAGCCTGCGGGCTGC-3'
      (SEQ ID NO:10)
#263  5'-CACTTGGTTGAAGCTTTGTACTTGGTTTG
      TGGTGAAAGAGGTTTC TTCTACACTCCAAA
      GACTAGAGGTATCGTTGAA-3' (SEQ ID NO:11)
#307  5'-GCTAACGTCGCCATGGCTAAGAGAGAAG
      AAGCTGAAGCTGAAGCTAGATTCGTTAACC
      AACAC-3'  (SEQ ID NO:12)
```

The following Polymerase Chain Reaction (PCR) was performed using the Gene Amp PCR reagent kit (Perkin Elmer, 761 Main Avewalk, Conn. 06859, USA) according to the manufacturer's instructions. In all cases, the PCR mixture was overlayed with 100 μl of mineral oil (Sigma Chemical Co, St. Louis, Mo., USA). The plasmid pAK220 (which is identical to pAK188) consists of a DNA sequence of 412 bp encoding the synthetic yeast signal/leader LaC212spx3 (described in Example 3 of WO 89/02463) followed by the insulin precursor MI5 (see SEQ ID NOS. 14, 15 and 16) inserted into the vector (phagemid) pBLUE-SCRIPT IIsk(+/−) (Stratagene, USA).

5 μl of oligonucleotide #220 (100 pmol)
5 μl of oligonucleotide #263 (100 pmol)
10 μl of 10X PCR buffer
16 μl of dNTP mix
0.5 μl of Taq enzyme
0.5 μl of pAK220 plasmid (identical to pAK188) as template (0.2 μg of DNA)
63 μl of water A total of 16 cycles were performed, each cycle comprising 1 minute at 95° C.; 1 minute at 40° C.; and 2 minutes at 72° C. The PCR mixture was then loaded onto a 2% agarose gel and subjected to electrophoresis using standard techniques. The resulting DNA fragment was cut out of the agarose gel and isolated using the Gene Clean kit (Bio 101 Inc., PO BOX 2284, La Jolla, Calif. 92038, USA) according to the manufacture's instructions. The purified PCR DNA fragment was dissolved in 10 μl of water and restriction endonuclease buffer and cut with the restriction endonucleases HindIII and XbaI according to standard techniques. The HindIII/XbaI DNA fragment was purified using The Gene Clean Kit as described.

Figure 2:
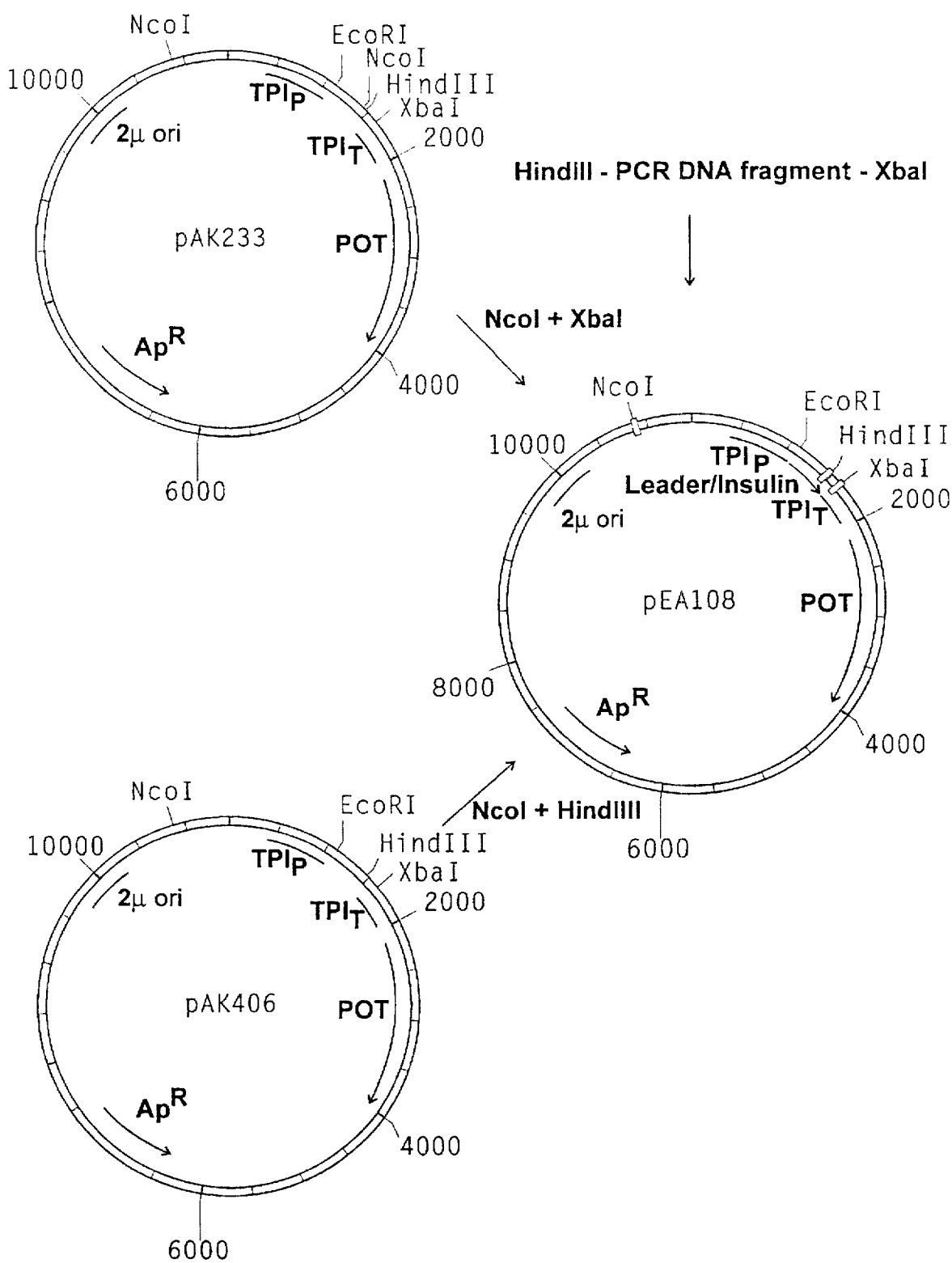
FIG. 2 shows the construction of the plasmid pEA108.

The plasmid pAK406 consists of a DNA sequence of 520 bp comprising an EcoRIFHindII fragment derived from pMT636 (described in WO 90/10075) encoding the yeast alpha factor leader and part of the insulin precursor ligated to the HindIII/XbaI fragment from pAK188 encoding the rest of the insulin precursor MI (see SEQ ID NOS. 32, 33 and 34) inserted into the vector cPOT. The vector pAK406 is shown in FIG. 2.

The plasmid pAK233 consists of a DNA sequence of 412 bp encoding the synthetic yeast signal/leader LaC212spx3 (described in Example 3 of WO 89/02463) followed by the gene for the insulin precursor B(1–29)-GluLysArg-A(1–21) (A21-Gly) (see SEQ ID NOS. 35, 36 and 37) inserted into the vector cPOT. The plasniid pAK233 is shown in FIG. 2.

The plasmid pAK233 was cut with the restriction endonucleases NcoI and XbaI and the vector fragment of 9273 bp isolated. The plasmid pAK406 was cut with the restriction endonucleases NcoI and HindIII and the vector fragment of 2012 bp isolated. These two DNA fragments were ligated together with the FindIII/XbaI PCR fragment using T4 DNA ligase and standard conditions. The ligation mixture was then transformed into a competent *E. coli* strain (R−, M+) followed by selection for ampicillin resistance. Plasmids were isolated from the resulting *E. coli* colonies using a standard DNA miniprep technique and checked with appropriate restriction endonucleases i.e. EcoRI, XbaI, NcoI, HindIII. The selected plasmid was shown by DNA sequencing analyses to contain the correct sequence for the Arg$^{B31}$ single chain human insulin precursor DNA and to be inserted after the DNA encoding the *S. cerevisiae* alpha factor DNA. The plasmid was named pEA108 and is shown in FIG. 2. The DNA sequence encoding the alpha factor leader/Arg$^{B31}$ single chain human insulin precursor complex and the amino acid sequence thereof are SEQ ID NOS. 38, 39 and 40. The plasmid pEA 108 was transformed into *S. cerevisiae* strain MT663 as described in Example 1 and the resulting strain was named yEA108.

B) The following Polymerase Chain Reaction (PCR) was performed using the Gene Amp PCR reagent kit (Perkin Elmer, 761 Main Avewalk Conn. 06859, USA) according to the manufacturer's instructions. In all cases, the PCR mixture was overlayed with 100 μl of mineral oil (Sigma Chemical Co., St. Louis, Mo., USA)

5 μl of oligonucleotide #220 (100 pmol)
5 μl of oligonucleotide #307 (100 pmol)
10 μl of 10X PCR buffer
16 μl of dNTP mix
0.5 μl of Taq enzyme
0.2 μl of pEA108 plasmid as template (0.1 ug DNA)
63 μl of water A total of 16 cycles were performed, each cycle comprising 1 minute at 95° C.; 1 minute at 40° C.; and 2 minutes at 72° C.. The PCR mixture was then loaded onto an 2% agarose gel and subjected to electrophoresis using standard techniques. The resulting DNA fragment was cut out of the agarose gel and isolated using the Gene Clean kit (Bio 101 Inc., PO BOX 2284, La Jolla, Calif. 92038, USA) according to the manufacture's instructions. The purified PCR DNA fragment was dissolved in 10 μl of water and restriction endonuclease buffer and cut with the restriction endonucleases NcoI and XbaI according to standard techniques. The NcoI/XbaI DNA fragment was purified using The Gene Clean Kit as described.

Figure 3:
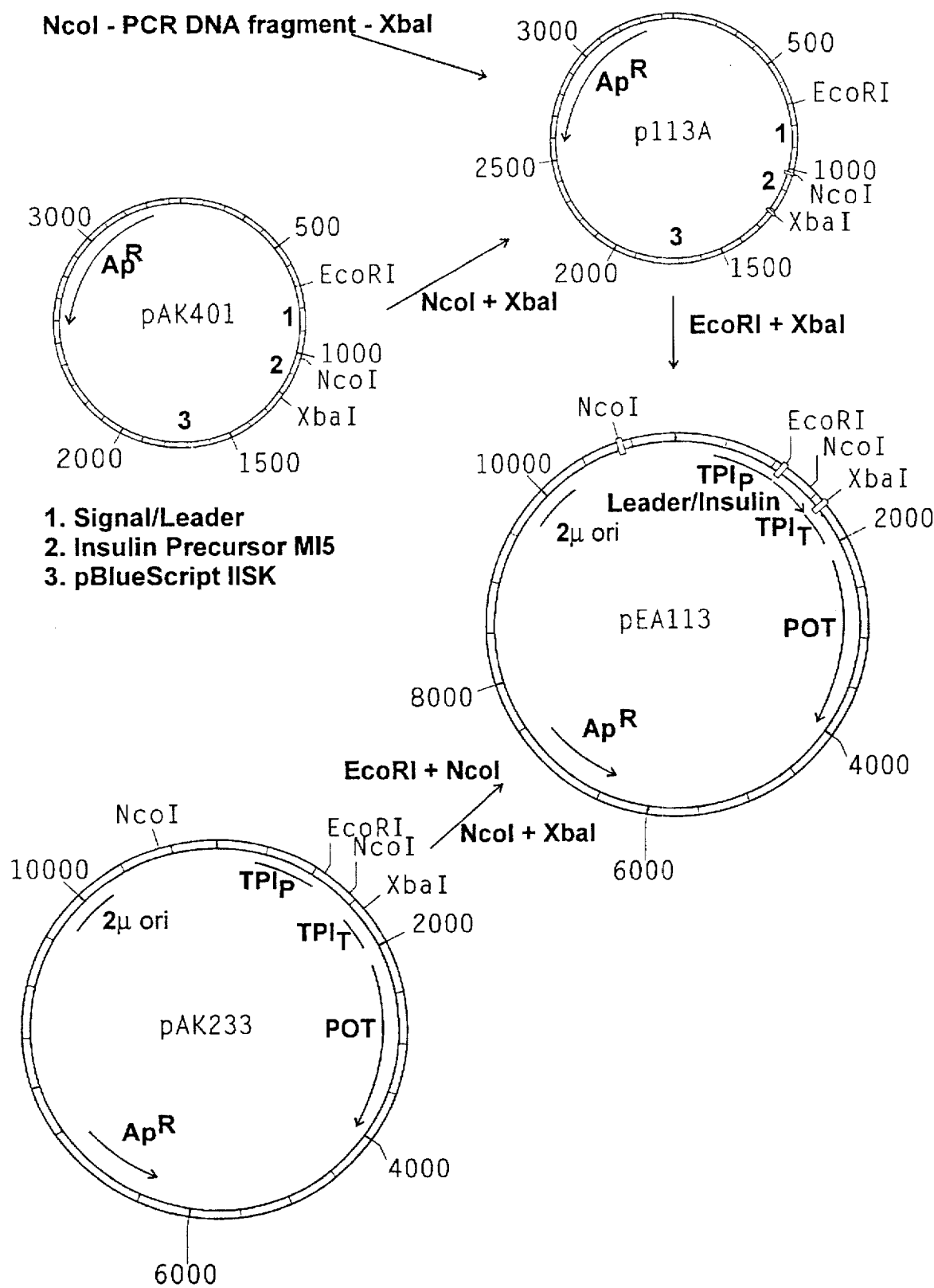
FIG. 3 shows the construction of the plasmid pEA113.

The plasmid pAK401 consists of a DNA sequence of 523 bp composed of an EcoRI/NcoI fragment derived from pMT636 (described in WO 90/10075) (constructed by by introducing a NcoI site in the 3'-end of the alpha leader by site directed mutagenesis) encoding the alpha factor leader followed by a NcoIIXbaI fragment from pAK188 encoding the insulin precursor MI5 (see SEQ ID NOS. 41, 42 and 43) inserted into the vector (phagemid) pBLUESCRIPT IIsk(+ /−) (Stratagene, USA). The plasmid pAK401 is shown in FIG. 3.

The plasmid pAK401 was cut with the restriction endonucleases NcoI and XbaI and the vector fragment of 3254 bp isolated and ligated together with the NcoI/XbaI PCR fragment. The ligation mixture was then transformed into a competent *E. coli* strain and plasmids were isolated from the resulting *E. coli* colonies using a standard DNA miniprep technique and checked with appropriate restriction endonucleases i.e. EcoRI, XbaI, NcoI. The selected plasmid, named p113A (shown in FIG. 3), was cut with EcoRI and XbaI and the fragment of 535 bp isolated.

The plasmid pAK233 was cut with the restriction endonucleases NcoI and XbaI, and with EcoRI/NcoI and the fragments of 9273 and 1644 bp isolated. These two DNA fragments were ligated together with the EcoRI/XbaI fragment from p113A using T4 DNA ligase and standard conditions. The ligation mixture was then transformed into a competent *E. coli* strain (R−, M+) followed by selection for ampicillin resistance. Plasmids were isolated from the resulting *E. coli* colonies using a standard DNA miniprep technique and checked with appropriate restriction endonucleases i.e. EcoRI, XbaI, NcoI, HindIII. The selected plasmid was shown by DNA sequencing analyses to contain the correct sequence for the $Arg^{B31}$ single chain human insulin precursor DNA with the N-terminal extension GluGluAla-GluAlaGluAlaArg and to be inserted after the DNA encoding the *S. cerevisiae* alpha factor DNA. The plasmid was named pEA113 and is shown in FIG. 3. The DNA sequence encoding the alpha factor leader/$Arg^{B-1}$ $Arg^{B31}$ single chain human insulin precursor having an N-terminal extension (GluGluAlaGluAlaGluAlaArg) and the amino acid sequence thereof are SEQ ID NOS. 44, 45 and 46. The plasmid pEA113 was transformed into *S. cerevisiae* strain MT663 as described in Example 1 and the resulting strain was named yEA113.

EXAMPLE 6

Synthesis of $Arg^{B-1}$ $Arg^{B31}$ single chain human insulin precursor having an N-terminal extension (GluGluAlaGluAlaGluAlaGluArg) from Yeast strain yEA136 using the alpha factor leader.

The following oligonucleotide was synthesized:

389 5'-GCTAACGTCGCCATGGCTAAGAGAGAA
GAAGCTGAAGCGAAGCTGAAAGATTCGTT
AACCAACAC-3' (SEQ ID NO:13)

The following PCR was performed using the Gene Amp PCR reagent kit
5 μl of oligonucleotide #220 (100 pmol)
5 μl of oligonucleotide #389 (100 pmol)
10 μl of 10X PCR buffer
16 μl of dNTP mix
0.5 μl of Taq enzyme
2 μl of pEA113 plasmid as template (0.5 ug DNA)
63 μl of water
A total of 12 cycles were performed, each cycle comprising 1 minute at 95° C.; 1 minute at 37° C.; and 2 minutes at 72° C.

The DNA encoding alpha factor leader/$Arg^{B-1}$ $Arg^{B31}$ single chain human insulin precursor having an N-terminal extension (GluGluAlaGluAlaGluAlaGluArg) was constructed in the same manner as described for the DNA encoding alpha factor leader/$Arg^{B-1}$ $Arg^{B31}$ single chain human insulin precursor having an N-terminal extension (GluGluAlaGluAlaGluAlaArg) in Example 5. The plasmid was named pEA136. The DNA sequence encoding the alpha factor leader/$Arg^{B-1}$ $Arg^{B31}$ single chain human insulin precursor having an N-termninal extension (GluGluAlaGluAlaGluAlaGluArg) and the amino acid sequence thereof are SEQ ID NOS. 47, 48 and 49. The plasmid pEA136 was transformed into *S. cerevisiae* strain MT663 as described in Example 1 and the resulting strain was named yEA136.

EXAMPLE 7

Synthesis of (A1,B1)-diBoc human insulin.

5 g of zinc-free human insulin was dissolved in 41.3 ml of DMSO. To the solution was added 3.090 ml of acetic acid.

The reaction was conducted at room temperature and initiated by addition of 565 mg of di-tert-butyl pyrocarbonate dissolved in 5.650 ml of DMSO. The reaction was allowed to proceed for 5½ hour and then stopped by addition of 250 μl of ethanolamine. The product was precipitated by addition of 1500 ml of acetone. The precipitate was isolated by centrifugation and dried in vacuum. A yield of 6.85 g material was obtained.

(A1,B1)-diBoc insulin was purified by reversed phase HPLC as follows: The crude product was dissolved in 100 ml of 25% ethanol in water, adjusted to pH 3.0 with HCl and applied to a column (5 cm diameter, 30 cm high) packed with octadecyldimethylsilyl-substituted silica particles (mean particle size 15 μm, pore size 100 Å) and equilibrated with elution buffer. The elution was performed using mixtures of ethanol and 1 mM aqueous HCl, 0.3M KCl at a flow of 2 l/h. The insulin was eluted by increasing the ethanol content from 30% to 45%. The appropriate fraction was diluted to 20% ethanol and precipitated at pH 4.8. The precipitated material was isolated by centrifugation and dried in vacuum. Thus 1.701 g of (A1,B1)-diBoc human insulin was obtained at a purity of 94.5%.

EXAMPLE 8

Synthesis of ($N^{\epsilon B29}$-benzoyl human insulin)$_6$, $3Zn^{2+}$.

400 mg of (A1,B1)-diBoc human insulin was dissolved in 2 mnl of DMSO. To the solution was added 748 μl of a mixture of N-methylmorpholine and DMSO (1:9, v/v). The reaction was conducted at 15° C. and initiated by addition of 14.6 mg of benzoic acid N-hydroxysuccinimide ester dissolved in 132 μl DMF. The reaction was stopped after 2 hours by addition of 100 ml of acetone. The precipitated material was isolated by centrifugation and dried in vacuum. 343 mg of material was collected.

The Boc protecting groups were eliminated by addition of 4 ml of TFA. The dissolved material was incubated for 30 minutes and then precipitated by addition of 50 ml of acetone. The precipitate was isolated by centrifugation and dried in vacuum.

$N^{\epsilon B29}$-benzoyl human insulin was purified by reversed phase HPLC as described in Example 7. A yield of 230 mg was obtained. Recrystallization from 15% aqueous ethanol containing 6 mM $Zn^{2+}$ and 50 mM citrate at pH 5.5 gave crystals of the title compound which were isolated by centrifugation and dried in vacuum. The yield was 190 mg.

Molecular mass, found by MS: 5911, theory: 5911.

EXAMPLE 9

Synthesis of ($N^{\epsilon B29}$-lithocholoyl human insulin)6 $3Zn^{2+}$.

400 mg of (A1,B1)-diBoc human insulin was dissolved in 2 ml of DMSO. To the solution was added 748 μl of a mixture of N-methylmorpholine and DMSO (1:9, v/v). The reaction was conducted at 15° C. and initiated by addition of 31.94 mg of lithocholic acid N-hydroxysuccinimide ester dissolved in 300 μl of DMF. The reaction was stopped after 2 hours by addition of 100 ml of acetone. The precipitated material was isolated by centrifugation and dried in vacuum. 331 mg of material was obtained.

The Boc protecting groups were eliminated by addition of 4 ml of TFA. The dissolved material was incubated for 30 minutes and then precipitated by addition of 50 ml of acetone. The precipitate was isolated by centrifugation and dried in vacuum. The yield was 376 mg.

B29-lithocholoyl insulin was purified by reversed phase HPLC as described in Example 7. A final yield of 67 mg was obtained at a purity of 94%. Recrystallization from 15% aqueous ethanol containing 6 mM $Zn^{2+}$ and 50 mM citrate at pH 5.5 gave crystals of the title compound which were isolated by centrifugation and dried in vacuum. The yield was 49 mg.

Molecular mass, found by MS: 6160, theory: 6166.

EXAMPLE 10

Synthesis of $(N^{\epsilon B29}$-decanoyl human insulin$)_6$, $3Zn^{2+}$.

400 mg of (A1,B1)-diBoc human insulin was dissolved in 2 ml of DMSO. To the solution was added 748 µl of a mixture of N-methylmorpholine and DMSO (1:9, v/v). The reaction was conducted at 15° C. and initiated by addition of 18.0 mg of decanoic acid N-hydroxysuccinimide ester dissolved in 132 µl of DMF. The reaction was stopped after 60 minutes and the product precipitated by addition of 100 ml of acetone. The precipitated material was isolated by centrifugation and dried in vacuum. 420 mg of intermediate product was collected.

The Boc protecting groups were eliminated by addition of 4 ml of TFA. The dissolved material was incubated for 30 minutes and the product was then precipitated by addition of 50 ml of acetone. The precipitate was isolated by centrifugation and dried in vacuum. The yield of crude product was 420 mg.

The crude product was purified by reversed phase HPLC as described in Example 7. A final yield of 254 mg of the title product was obtained. The purity was 96.1%. Recrystallization from 15% aqueous ethanol containing 6 mM $Zn^{2+}$ and 50 mM citrate at pH 5.5 gave crystals of the title compound which were isolated by centrifugation and dried in vacuum. The yield was 217 mg.

Molecular mass, found by MS: 5962, theory: 5962.

EXAMPLE 11

Synthesis of des(B30) human insulin.

Synthesis of des(B30) human insulin was carried out as described by Markussen (Methods in diabetes research, Vol. I, Laboratory methods, part B, 404–410. Ed: J. Larner and S. Phol, John Wiley & Sons, 1984). 5 g of human insulin was dissolved in 500 ml of water while the pH value of the solution was kept at 2.6 by addition of 0.5M sulphuric acid. Subsequently, the insulin was salted out by addition of 100 g of ammonium sulphate and the precipitate was isolated by centrifugation. The pellet was dissolved in 800 ml of 0.1M ammonium hydrogen carbonate and the pH value of the solution was adjusted to 8.4 with 1M ammonia.

50 mg of bovine carboxypeptidase A was suspended in 25 ml of water and isolated by centrifugation. The crystals were suspended in 25 ml of water and 1M ammonia was added until a clear solution was obtained at a final pH of 10. The carboxypeptidase solution was added to the insulin solution and the reaction was allowed to proceed for 24 hours. A few drops of toluene were added to act as preservative during the reaction.

After 24 hours the des(B30) human insulin was crystallized by successive addition of 80 g of sodium chloride while the solution was stirred. The pH value was then adjusted to 8.3 and the crystallization was allowed to proceed for 20 hours with gentle stirring. The crystals were isolated on a 1.2 µm filter, washed with 250 ml of ice cold 2-propanol and finally dried in vacuum.

EXAMPLE 12

Synthesis of (A1,B1)-diBoc des(B30) human insulin.

The title compound was synthesized by a method similar to that described in Example 7, using des(B30) porcine insulin as the starting material. The crude product was precipitated by acetone and dried in vacuum. The (A1,B1)-diBoc des(B30) human insulin was purified by reversed phase HPLC as described in Example 7.

EXAMPLE 13

Synthesis of $N^{\epsilon B29}$-decanoyl des(B30) human insulin.

400 mg of (A1,B1)-diBoc des(B30) human insulin was used as starting material for the synthesis of $N^{\epsilon B29}$-decanoyl des(B30) human insulin, following the procedure described in Example 10. The crude product was precipitated by acetone, dried in vacuum and deprotected using TFA. The resulting product was precipitated by acetone and dried in vacuum. $N^{\epsilon B29}$-decanoyl des(1330) human insulin was then purified by reversed phase HPLC as described in Example 10.

Molecular mass, found by MS: 5856, theory: 5861.

EXAMPLE 14

Synthesis of $N^{\epsilon B29}$-dodecanogl des(B30) human insulin.
a. Immobilization of A. lyticus protease 13 mg of A. lyticus protease, dissolved in 5 ml of aqueous 0.2M $NaHCO_3$ buffer, pH 9.4, was mixed with 4 ml of settled MiniLeak® Medium gel, which had been washed with the same buffer (MiniLeak is a divinylsulfone activated Sepharose CL 6B, obtained from KemEnTec, Copenhagen). The gel was kept in suspension by gentle stirring for 24 hours at room temperature. Then, the gel was isolated by filtration, washed with water, and suspended in 20 ml of 1M ethanolamine buffer, pH 9.4, and kept in suspension for 24 hours at room temperature. Finally, the gel was washed with water followed by 0.1M acetic acid and stored at 4° C. The enzyme activity in the filtrate was 13% of that in the initial solution, indicating a yield in the immobilization reaction of about 87%.

b. Immobilization of porcine trypsin

Porcine trypsin was immobilized to Minileak® Low to a degree of substitution of 1 mg per ml of gel, using the conditions described above for immobilization of A. lyticus.

c. Synthesis of Glu(GluAla)$_3$Arg-B(1–29), ThrArg-A(1–21) insulin using immobilized A. lyticus protease To 200 mg of Glu(GluAla)$_3$Arg-B(1–29)-ThrArg-A(1–21) single-chain human insulin precursor, dissolved in 20 ml of 0.1M $NaHCO_3$ buffer, pH 9.0, was added 4 ml of the gel carrying the immobilized A. lyticus protease. After the gel had been kept in suspension in the reaction mixture for 6 hours at room temperature the hydrolysis was complete, rendering Glu(GluAla)$_3$-Arg-B(1–29), ThrArg-A(1–21) human insulin (the reaction was followed by reversed phase HPLC). After the hydrolysis, the gel was removed by filtration. To the filtrate was added 5 ml of ethanol and 15 µL of 1M $ZnCl_2$ and the pH was adjusted to 5.0 using HCl. The precipitation of the product was completed on standing overnight at 4° C. with gentle stirring. The product was isolated by centrifugation. After one washing with 1 ml of ice cold 20% ethanol and drying in vacuo the yield was 190 mg.

d. Synthesis of $N^{\alpha A1}$,$N^{\alpha B1}$, $N^{\epsilon B29}$-tridodecanoyl Glu(GluAla)$_3$Arg-B(1–29), Thr-Arg-A(1–21) human insulin using dodecanoic acid N-hydroxysuccinimide ester 190 mg (30 µmol) of Glu(GluAla)$_3$Arg-B(1–29), ThrArg-A(1–21) insulin was dissolved in 1 ml of DMSO and 1.05 ml of a 0.572M solution of N,N-diisopropylethylamine in DMF. The solution was cooled to 15° C. and 36 mg (120 μmol) of dodecanoic acid N-hydroxysuccinimide ester dissolved in 0.6 ml of DMSO was added. The reaction was completed within 24 hours. The lipophilic title compound was not isolated.

e. Synthesis of $N^{\epsilon B29}$-dodecanoyl des(B33) insulin

The product from the previous step, d., contained in approximately 2.65 ml of DMSO/DMF/N,N-diisopropylethylamine was diluted with 10.6 ml of a 50 mM glycine buffer comprising 20% ethanol and the pH adjusted to 10 with NaOH. After standing for 1 hour at room temperature 1 ml of Minileak gel, carrying 1 mg of immobilized trypsin per ml of gel, was added. The reaction mixture was stirred gently for 48 hours at room temperature. In order to isolate the desired product, the reaction mixture was applied to a reversed phase HPLC column (5 cm in diameter, 30 cm high), packed with octadecyldimethylsilyl-substituted silica particles (mean particle size 15 μm, pore size 100 Å). For the elution was used 20 mM Tris/HCl buffers, adjusted to pH 7.7 and comprising an increasing concentration of ethanol, from 40% to 44% (v/v), at a rate of 2000 ml/h. The major peak eluting at about 43–44% of ethanol contained the title compound. The fractions containing the major peak were pooled, water was added to reduce the ethanol concentration to 20% (v/v), and the pH was adjusted to 5.5. The solution was left overnight at −20° C., whereby the product precipitated. The precipitate was isolated by centrifugation at −8° C. and dried in vacuo. The yield of the title compound was 90 mg.

Molecular mass, found by MS: 5892, theory: 5890.

EXAMPLE 15

Synthesis of $N^{\epsilon B29}$-(N-myristoyl-α-glutamyl) human insulin.

500 mg of (A1,B1)-diBoc human insulin was dissolved in 2.5 ml of DMSO and 428 μl of ethyl diisopropylamine, diluted with 2.5 ml of DMSO/DMF 1/1 (v/v), was added. The temperature was adjusted to 15° C. and 85 mg of N-myristoyl-Glu(OBut) N-hydroxysuccinimide ester, dissolved in 2.5 ml of DMSO/DMF 1/1 (v/v), was added. After 30 min the reaction mixture was poured into 60 ml of water, the pH adjusted to 5 and the precipitate isolated by centrifugation. The precipitate was dried in vacuo. The dried reaction mixture was dissolved in 25 ml of TFA, and the solution was left for 30 min at room temperature. The TFA was removed by evaporation in vacuo. The gelatinous residue was dissolved in 60 ml of water and the pH was adjusted to 11.2 using concentrated ammonia. The title compound was crystallized from this solution by adjustment of the pH to 8.5 using 6N HCl. The product was isolated by centrifugation, washed once by 10 ml of water, and dried in vacuo. Yield 356 mg. Purity by HPLC 94%.

The product of this example is thus human insulin wherein the ε-amino group of $Lys^{B29}$ has a substituent of the following structure: $CH_3(CH_2)_{12}CONHCH(CH_2CH_2COOH)CO-$.

Molecular mass, found by MS: 6146, theory: 6148.

EXAMPLE 16

Synthesis of $N^{\epsilon B29}$-undecanoyl des(B30) human insulin.

The title compound was synthesized analogously to $N^{\epsilon B29}$-dodecanoyl des(B30) human insulin as described in Example 14, by using undecanoic acid N-hydroxysuccinimide ester instead of dodecanoic acid N-hydroxysuccinimide ester.

Molecular mass of the product found by MS: 5876, theory: 5876.

EXAMPLE 17

Synthesis of $N^{\epsilon B29}$-tridecanoyl des(B30) human insulin.

The title compound was synthesized analogously to $N^{\epsilon B29}$-dodecanoyl des(B30) human insulin as described in Example 14, by using tridecanoic acid N-hydroxysuccinimide ester instead of dodecanoic acid N-hydroxysuccinimide ester.

Molecular mass of the product found by MS: 5899, theory: 5904.

EXAMPLE 18

Synthesis of $N^{\epsilon B29}$-myristoyl des(B30) human insulin.

The title compound was synthesized analogously to $N^{\epsilon B29}$-dodecanoyl des(B30) human insulin as described in Example 14, by using myristic acid N-hydroxysuccinimide ester instead of dodecanoic acid N-hydroxysuccinimide ester.

Molecular mass of the product found by MS: 5923, theory: 5918.

EXAMPLE 19

Synthesis of $N^{\epsilon B29}$-palmitoyl des(B30) human insulin.

The title compound was synthesized analogously to $N^{\epsilon B29}$-dodecanoyl des(B30) human insulin as described in Example 14, by using palmitic acid N-hydroxysuccinimide ester instead of dodecanoic acid N-hydroxysuccinimide ester.

Molecular mass of the product found by MS: 5944, theory: 5946.

EXAMPLE 20

Synthesis of $N^{\epsilon B29}$-suberoyl-D-thyroxine human insulin.

a. Preparation of N-(succinimidylsuberoyl)-D-thyroxine.

Disuccinimidyl suberate (1.0 g, Pierce) was dissolved in DMF (50 ml), and Dthyroxine (2.0 g, Aldrich) was added with stirring at 20° C. The thyroxine slowly dissolved, and after 20 hours the solvent was removed by evaporation in vacuo. The oily residue was crystallized from 2-propanol to yield 0.6 g of N-(succinimidylsuberoyl)-D-thyroxine, m.p. 128°–133° C.

b. Reaction of (A1,B1)-diBoc human insulin with N-(succinimidylsuberoyl)-D-thyroxine. (A1,B1)-diBoc human insulin (200 mg) was dissolved in dry DMF (10 ml) by addition of triethylamine (20 μl) at room temperature. Then, N-(succinimidylsuberoyl)-D-thyroxine (80 mg) was added. The reaction was monitored by reversed phase HPLC and when the reaction was about 90% complete, the solvent was removed in vacuo. To the evaporation residue, anhydrous trifluoroacetic acid (5 ml) was added, and the solution was kept for 1 hour at room temperature. After removal of the trifluoroacetic acid in vacuo, the residue was dissolved in a mixture of 1M acetic acid (5 ml) and acetonitrile (1.5 ml), purified by preparative reversed phase HPLC and desalted on a PD-10 column. The yield of $N^{\epsilon B29}$-suberoyl-D-thyroxine human insulin was 50 mg.

The product of this example is thus human insulin wherein the ε-amino group of $Lys^{B29}$ has a substituent of the following structure: $Thyrox-CO(CH_2)_6CO-$, wherein Thyrox is thyroxine which is bound to the octanedioic acid moiety via an amide bond to its α-amino group.

Molecular mass of the product found by MS: 6724, theory: 6723.

EXAMPLE 21

Synthesis of $N^{\epsilon B29}$-(2-succinylamido)myristic acid human insulin.

a. Preparation of (α-aminomyristic acid methyl ester,HCl.

To methanol (5 ml, Merck) at −10° C., thionyl chloride (0.2 ml, Aldrich) was added dropwise while stirring vigorously. Then, α-aminomyristic acid (0.7 g, prepared from the α-bromo acid by reaction with ammonia) was added. The reaction mixture was stirred at room temperature overnight, and then evaporated to dryness. The crude product (0.7 g) was used directly in step b.

b. Preparation of N-succinoyl-α-aminomyristic acid methyl ester. α-Aminomyristic acid methyl ester.HCl (0.7 g) was dissolved in chloroform (25 ml, Merck). Triethylamine (0.35 ml, Fluka) was added, followed by succinic anhydride (0.3 g, Fluka). The reaction mixture was stirred at room temperature for 2 hours, concentrated to dryness, and the residue recrystallized from ethyl acetate/petroleum ether (1/1). Yield: 0.8 g.

c. Preparation of N-(succinirnidvlsuccinoyl)-α-iminomyristic acid methyl ester.

N-succinoyl-α-aminomyristic acid methyl ester (0.8 g) was dissolved in dry DMF (10 ml, Merck, dried over 4 Å molecular sieve). Dry pyridine (80 µl, Merck), and di(N-succinimidyl)carbonate (1.8 g, Fluka) were added, and the reaction mixture was stirred overnight at room temperature. The evaporation residue was purified by flash chromatography on silica gel 60 (Merck), and recrystallized from 2-propanol/petroleum ether (1/1). Yield of N-(succinimidylsuccinoyl)-α-aminomyristic acid methyl ester: 0.13 g, m.p. 64°–66° C..

d. Reaction of (A1,B1)-diBoc human insulin with N-(succinimidylsuccinoyl)-α-aminomyristic acid methyl ester.

The reaction was carried out as in Example 20 b., but using N-(succinimidylsuccinoyl)-α-amninomyristic acid methyl ester (16 mg) instead of N(succinimidylsuberoyl)-D-thyroxine. After removal of the trifluoroacetic acid in vacuo, the evaporation residue was treated with 0.1M sodium hydroxide at 0° C. to saponify the methyl ester. When the saponification was judged to be complete by reversed phase HPLC, the pH value in the solution was adjusted to 3, and the solution was lyophulized. After purification by preparative reversed phase HPLC and desalting on a PD-10 column, the yield of $N^{\epsilon B29}$-($_2$succinylamido) myristic acid human insulin was 39 mg.

The product of this example is thus human insulin wherein the ε-amino group of $Lys^{B29}$ has a substituent of the following structure: $CH_3(CH_2)_{11}CH(COOH)NHCOCH_2CH_2CO-$.

Molecular mass of the product found by MS: 6130, theory: 6133.

EXAMPLE 22

Synthesis of $NB^{\epsilon B29}$-octyloxycarbonyl human insulin.

The synthesis was carried out as in Example 20 b., but using noctyloxycarbonyl N-hydroxysuccinimide (9 mg, prepared from n-octyl chloroformate (Aldrich) and N-hydroxysuccinimide), instead of N-(succinimidylsuberoyl)-D-thyroxine. The yield of $N^{\epsilon B29}$-octyloxycarbonyl human insulin was 86 mg.

The product of this example is thus human insulin wherein the ε-amino group of $Lys^{\epsilon B29}$ has a substituent of the following structure: $CH_3(CH_2)_7OCO-$.

Molecular mass of the product found by MS: 5960, theory: 5964.

EXAMPLE 23

Synthesis of $N^{\epsilon B29}$-(2-succinylamido)palmitic acid human insulin.

a. Preparation of N-(succinimidylsuccinoyl)-α-amino palmitic acid methyl ester.

This compound was prepared as described in Example 21 a.–c., using α-amino palmitic acid instead of α-amino myristic acid.

b. Reaction of (A1,B1)-diBoc human insulin with N-(succinimidylsuccinoyl)-α-aminopalmitictic acid methyl ester.

The reaction was carried out as in Example 21 d., but using N-(succinimidylsuccinoyl)-α-aminopalmitic acid methyl ester instead of N(succinimnidylsuccinoyl)-α-aminopalmitic acid methyl ester to give $N^{\epsilon B29}$-($_2$succinylamido)palmitic acid human insulin.

The product of this example is thus human insulin wherein the ε-amino group of $Lys^{B29}$ has a substituent of the following structure: $CH_3(CH_2)_{13}CH(COOH)NHCOCH_2CH_2CO-$.

EXAMPLE 24

Synthesis of $N^{\epsilon B29}$-(2-succinylamidoethyloxy, palmitic acid human insulin.

a. Preparation of N-(succinimidylsuccinoyl)-2-aminoethyloxy palnitic acid methyl ester.

This compound was prepared as described in Example 21 a.–c. but using 2-aminoethyloxy palnitic acid (synthesized by the general procedure described by R. TenBrink. J. Org. Chem. 52 (1987) 418–422 instead of α-anmino myristic acid.

b. Reaction of (A1,B1)-diBoc human insulin with N-(succinimidylsuccinoyl)-2-aminoethyloxypalmitictic acid methyl ester.

The reaction was carried out as in Example 21 d., but using N(succinimidylsuccinoyl)-2-aminoethyloxypalmitic acid methyl ester instead of N(succinimidylsuccinoyl)-α-aminomyristic acid methyl ester to give $N^{\epsilon B29}$-(2succinylamidoethyloxy)palmitic acid human insulin.

The product of this example is thus human insulin wherein the ε-amino group of $Lys^{B29}$ has a substituent of the following structure: $CH_3(CH_2)_{13}CH(COOH)NHCH_2CH_2OCOCH_2CH_2CO-$.

EXAMPLE 25

Synthesis of $N^{\epsilon B29}$-lithocholoyl-α-glutamyl des(B30) human insulin.

The synthesis was carried out as in Example 13 using N-lithocholoyl-L-glutamic acid (α-N-hydroxysuccinimide ester, γ-tert-butyl ester instead of decanoic acid N-hydroxysuccinimide ester.

The product of this example is thus des(B30) human insulin wherein the ε-amino group of $Lys^{B29}$ has a substituent of the following structure: lithocholoyl-NHCH $(CH_2CH_2COOH)CO-$.

Molecular mass of the product found by MS: 6194, theory: 6193.

EXAMPLE 26

Synthesis of $N^{\epsilon B29}$-3,3',5,5'-tetraiodothyroacetyl human insulin.

The synthesis was carried out as in Example 10 using 3,3',5,5'-tetraiodothyroacetic acid N-hydroxysuccinimide ester, instead of decanoic acid N-hydroxysuccinimide ester.

31

Molecular mass of the product found by MS: 6536. theory: 6538.

EXAMPLE 27

Synthesis of $N^{\epsilon B29}$-L-thyroxyl human insulin.

The synthesis was carried out as in Example 10 using Boc-L-thyroxine N-hydroxysuccinimide ester, instead of decanoic acid N-hydroxysuccinimide ester.

Molecular mass of the product found by MS: 6572. theory: 6567.

EXAMPLE 28

A pharmaceutical composition comprising 600 nmol/ml of $N^{\epsilon B29}$-decanoyl des(B30) human insulin, 1/3$Zn^{2+}$ in solution.

$N^{\epsilon B29}$-decanoyl des(0330) human insulin (1.2 µmol) was dissolved in water (0.8 ml) and the pH value was adjusted to 7.5 by addition of 0.2M sodium hydroxide. 0.01M zinc acetate (60 µl) and a solution containing 0.75% of phenol and 4% of glycerol (0.8 ml) was added. The pH value of the solution was adjusted to 7.5 using 0.2M sodium hydroxide and the volume of the solution was adjusted to 2 ml with water.

The resulting solution was sterilized by filtration and transferred aseptically to a cartridge or a vial.

32

EXAMPLE 29

A pharmaceutical composition comprising 600 mmol/ml of $N^{\epsilon B29}$-decanoyl human insulin, 1/2$Zn^{2+}$ in solution. 1.2 µmol of the title compound was dissolved in water (0.8 ml) and the pH value was adjusted to 7.5 by addition of 0.2M sodium hydroxide. A solution containing 0.75% of phenol and 1.75% of sodium chloride (0.8 ml) was added. The pH value of the solution was adjusted to 7.5 using 0.2M sodium hydroxide and the volume of the solution was adjusted to 2 ml with water.

The resulting solution was sterilized by filtration and transferred aseptically to a cartridge or a vial.

EXAMPLE 30

A pharmaceutical composition comprising 600 nmol/ml of $N^{\epsilon B29}$-lithocholoyl human insulin in solution.

1.2 µmol of the title compound was suspended in water (0.8 ml) and dissolved by adjusting the pH value of the solution to 8.5 using 0.2M sodium hydroxide. To the solution was then added 0.8 ml of a stock solution containing 0.75% cresol and 4% glycerol in water. Finally, the pH value was again adjusted to 8.5 and the volume of the solution was adjusted to 2 ml with water.

The resulting solution was sterilized by filtration and transferred aseptically to a cartridge or a vial.

---

We claim:

1. An insulin derivative having the following sequence:

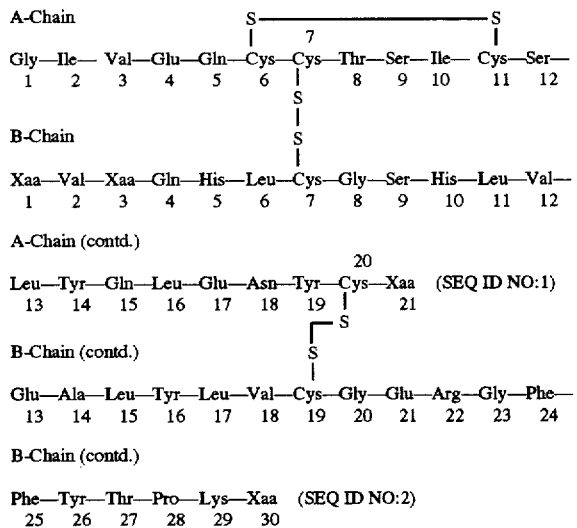

wherein
- (a) Xaa at positions A21 and B3 are, independently, any amino acid residue which can be coded for by the genetic code except Lys, Arg and Cys;
- (b) Xaa at position B1 is Phe or is deleted;
- (c) Xaa at position B30 is any amino acid residue which can be coded for by the genetic code except Lys, Arg and Cys; and
- (d) the ε-amino group of Lys$^{B29}$ is substituted with an acyl group having at least 10 carbon atoms;

wherein insulin derivative is a $Zn^{2+}$ complex and the $Zn^{2+}$ complex of the insulin derivative is more water soluble than the insulin derivative without $Zn^{2+}$.

2. The insulin derivative according to claim 1, wherein Xaa at position A21 is Asn.

3. The insulin derivative according to claim 2, wherein the acyl group has from 12 to 24 carbon atoms.

4. The insulin derivative according to claim 1, wherein Xaa at position A21 is Ala, Asn, Gln, Gly or Ser.

5. The insulin derivative according to claim 4, wherein the acyl group has from 12 to 24 carbon atoms.

6. The insulin derivative according to claim 1, wherein Xaa at position B1 is deleted.

7. The insulin derivative according to claim 6, wherein the acyl group has from 12 to 24 carbon atoms.

8. The insulin derivative according to claim 1, wherein Xaa at position B1 is Phe.

9. The insulin derivative according to claim 8, wherein the acyl group has from 12 to 24 carbon atoms.

10. The insulin derivative according to claim 1, wherein Xaa at position B3 is Asn, Asp, Gln or Thr.

11. The insulin derivative according to claim 10, wherein the acyl group has from 12 to 24 carbon atoms.

12. The insulin derivative according to claim 1, wherein Xaa at position B30 is Ala or Thr.

13. The insulin derivative according to claim 12, wherein the acyl group has from 12 to 24 carbon atoms.

14. The insulin derivative according to claim 1, wherein Xaa at position A21 is Ala, Asn, Gln, Gly or Ser, Xaa at position B3 is Asn, Asp, Gln or Thr, and Xaa at position B30 is Ala or Thr.

15. The insulin derivative according to claim 14, wherein the acyl group has from 12 to 24 carbon atoms.

16. The insulin derivative according to claim 1, wherein Xaa at position A21 is Asn, Xaa at position B3 is Asn, Xaa at position B1 is Phe and Xaa at position B30 is Thr.

17. The insulin derivative according to claim 16, wherein the acyl has from 12 to 24 carbon atoms.

18. The insulin derivative according to claim 1, wherein the acyl group has from 12 to 24 carbon atoms.

19. The insulin derivative according to claim 18, wherein the acyl group is a linear, saturated acyl group.

20. The insulin derivative according to claim 19, wherein the acyl group is tetradecanoyl or hexadecanoyl.

21. The insulin derivative according to claim 1 which is $N^{εB29}$-decanoyl human insulin.

22. The insulin derivative according to claim 1 which is $N^{εB29}$-dodecanoyl human insulin.

23. The insulin derivative according to claim 1 which is $N^{εB29}$-tetradecanoyl human insulin.

24. The insulin derivative according to claim 1 which is $N^{εB29}$-lithocholoyl human insulin.

25. The insulin derivative according to claim 1 which is in the form of a hexamer.

26. The insulin derivative according to claim 25, wherein the acyl group has from 12 to 24 carbon atoms.

27. The insulin derivative according to claim 25, wherein Xaa at position A21 is Asn, Xaa at position B1 is Phe, Xaa at position B3 is Asn, and Xaa at position B30 is Thr.

28. The insulin derivative according to claim 25, wherein two zinc ions bind to the hexamer.

29. The insulin derivative according to claim 28, wherein the acyl group has from 12 to 24 carbon atoms.

30. The insulin derivative according to claim 25, wherein three zinc ions bind to the hexamer.

31. The insulin derivative according to claim 30, wherein the acyl group has from 12 to 24 carbon atoms.

32. The insulin derivative according to claim 25, wherein four zinc ions bind to the hexamer.

33. The insulin derivative according to claim 32, wherein the acyl group has from 12 to 24 carbon atoms.

34. A pharmaceutical composition which is an aqueous solution, comprising (a) an insulin derivative according to claim 1, (b) an isotonic agent, (c) a preservative and (d) a buffer.

35. The pharmaceutical composition according to claim 34, wherein the pH of the aqueous solution is in the range of 6.5–8.5.

36. The pharmaceutical composition according to claim 34, wherein the solubility of the insulin derivative exceeds 600 nmol/ml of the aqueous solution.

37. The pharmaceutical composition according to claim 34, further comprising an insulin or an insulin analogue which has a rapid onset of action.

38. The pharmaceutical composition according to claim 34, wherein Xaa at position A21 is Asn, Xaa at position B3 is Asn, Xaa at position Bi is Phe and Xaa at position B30 is Thr.

39. The pharmaceutical composition according to claim 34, wherein the acyl group has from 12 to 24 carbon atoms.

40. The pharmaceutical composition according to claim 39, wherein the acyl group is tetradecanoyl or hexadecanoyl.

41. The pharmaceutical composition according to claim 34, wherein the insulin derivative is $N^{\epsilon B29}$-decanoyl human insulin.

42. The pharmaceutical composition according to claim 34, wherein the insulin derivative is $N^{\epsilon B29}$-dodecanoyl human insulin.

43. The pharmaceutical composition according to claim 34, wherein the insulin derivative is $N^{\epsilon B29}$-tetradecanoyl human insulin.

44. The pharmaceutical composition according to claim 34, wherein the insulin derivative is $N^{\epsilon B29}$-lithocholoyl human insulin.

45. The pharmaceutical composition according to claim 34, wherein the insulin derivative is in the form of a hexamer.

46. A method of treating diabetes in a patient in need of such a treatment, comprising administering to the patient a therapeutically effective amount of a pharmaceutical composition according to claim 34.

47. An insulin derivative having the following sequence:

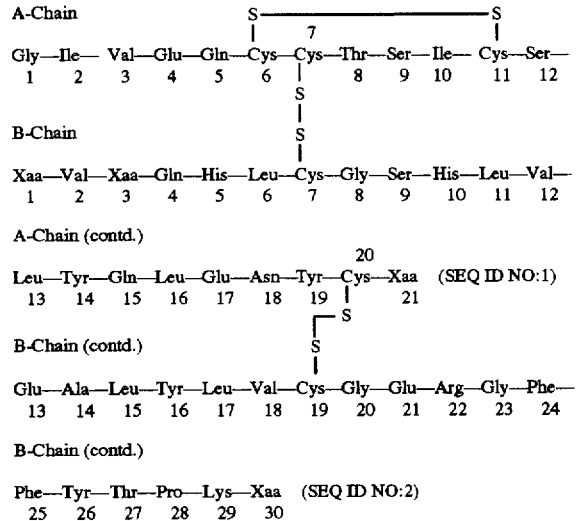

wherein
(a) Xaa at positions A21 and B3 are, independently, any amino acid residue which can be coded for by the genetic code except Lys, Arg and Cys;
(b) Xaa at position B1 is Phe or is deleted;
(c) Xaa at position B30 is deleted; and
(d) the ε-amino group of $Lys^{B29}$ is substituted with an acyl group having at least 10 carbon atoms;
wherein insulin derivative is a $Zn^{2+}$ complex and the $Zn^{2+}$ complex of the insulin derivative is more water soluble than the insulin derivative without $Zn^{2+}$.

48. The insulin derivative according to claim 47, wherein Xaa at position A21 is Ala, Asn, Gln, Gly or Ser.

49. The insulin derivative according to claim 48, wherein the acyl group has from 12 to 24 carbon atoms.

50. The insulin derivative according to claim 47, wherein Xaa at position B1 is deleted.

51. The insulin derivative according to claim 50, wherein the acyl group has from 12 to 24 carbon atoms.

52. The insulin derivative according to claim 47, wherein Xaa at position B1 is Phe.

53. The insulin derivative according to claim 52, wherein the acyl group has from 12 to 24 carbon atoms.

54. The insulin derivative according to claim 47, wherein Xaa at position B3 is Asn, Asp, Gln or Thr.

55. The insulin derivative according to claim 54, wherein the acyl group has from 12 to 24 carbon atoms.

56. The insulin derivative according to claim 47 wherein Xaa at position A21 is Ala, Asn, Gln, Gly or Ser, and Xaa at position B3 is Asn, Asp, Gln or Thr.

57. The insulin derivative according to claim 56, wherein the acyl group has from 12 to 24 carbon atoms.

58. The insulin derivative according to claim 47, wherein Xaa at position A21 is Asn, Xaa at position B13 is Phe, and Xaa at position B3 is Asn.

59. The insulin derivative according to claim 58, wherein the acyl group has from 12 to 24 carbon atoms.

60. The insulin derivative according to claim 47, wherein the acyl group has from 12 to 24 carbon atoms.

61. The insulin derivative according to claim 60, wherein the acyl group is a linear, saturated acyl group.

62. The insulin derivative according to claim 61, wherein the acyl group is tetradecanoyl or hexadecanoyl.

63. The insulin derivative according to claim 47 which is $N^{\epsilon B29}$-hexadecanoyl des(B30) human insulin.

64. The insulin derivative according to claim 47 which is $N^{\epsilon B29}$-tetradecanoyl des(B30) human insulin.

65. The insulin derivative according to claim 47 which is $N^{\epsilon B29}$-tridecanoyl des(B30) human insulin.

66. The insulin derivative according to claim 47 which is $N^{\epsilon B29}$-decanoyl, des(B30) insulin.

67. The insulin derivative according to claim 47 which is $N^{\epsilon B29}$-lithocholoylα-glutamyl, des(B30) human insulin.

68. The insulin derivative according to claim 47 which is $N^{\epsilon B29}$-undecanoyl, des(B30) insulin.

69. The insulin derivative according to claim 47 which is $N^{\epsilon B29}$-dodecanoyl, des(B30) insulin.

70. The insulin derivative according to claim 47 which is in the form of a hexamer.

71. The insulin derivative according to claim 70, wherein the acyl group has from 12 to 24 carbon atoms.

72. The insulin derivative according to claim 70, wherein Xaa at position A21 is Asn, Xaa at position B3 is Asn, and Xaa at position B1 is Phe.

73. The insulin derivative according to claim 70, wherein two zinc ions bind to the hexamer.

74. The insulin derivative according to claim 73, wherein the acyl group has from 12 to 24 carbon atoms.

75. The insulin derivative according to claim 70, wherein three zinc ions bind to the hexamer.

76. The insulin derivative according to claim 75, wherein the acyl group has from 12 to 24 carbon atoms.

77. The insulin derivative according to claim 70, wherein four zinc ions bind to the hexamer.

78. The insulin derivative according to claim 77, wherein the acyl group has from 12 to 24 carbon atoms.

79. A pharmaceutical composition which is an aqueous solution, comprising (a) an insulin derivative according to claim 47; (b) an isotonic agent, (c) a preservative and (d) a buffer.

80. The pharmaceutical composition according to claim 79, wherein the pH of the aqueous solution is in the range of 6.5–8.5.

81. The pharmaceutical composition according to claim 79, wherein the solubility of the insulin derivative exceeds 600 nmol/ml of the aqueous solution.

82. The pharmaceutical composition according to claim 79, further comprising an insulin or an insulin analogue which has a rapid onset of action.

83. The pharmaceutical composition according to claim 79, wherein the insulin derivative is a $Zn^{2+}$ complex.

84. The pharmaceutical composition according to claim 79, wherein Xaa at position A21 is Asn, Xaa at position B3 is Asn, and Xaa at position B1 is Phe.

85. The pharmaceutical composition according to claim 79, wherein the acyl group has from 12 to 24 carbon atoms.

86. The pharmaceutical composition according to claim 85, wherein the acyl group is tetradecanoyl or hexadecanoyl.

87. The pharmaceutical composition according to claim 79, wherein the insulin derivative is $N^{\epsilon B29}$-hexadecanoyl des(B30) human insulin.

88. The pharmaceutical composition according to claim 79, wherein the insulin derivative is $N^{\epsilon B29}$-tetradecanoyl des(B30) human insulin.

89. The pharmaceutical composition according to claim 79, wherein the insulin derivative is $N^{\epsilon B29}$-tridecanoyl des(B30) human insulin.

90. The pharmaceutical composition according to claim 79, wherein the insulin derivative is $N^{\epsilon B29}$-decanoyl, des(B30) insulin.

91. The pharmaceutical composition according to claim 79, wherein the insulin derivative is $N^{\epsilon B29}$-lithocholoyl-α-glutamyl, des(B30) human insulin.

92. The pharmaceutical composition according to claim 79, wherein the insulin derivative is $N^{\epsilon B29}$-undecanoyl, des(B30) insulin.

93. The pharmaceutical composition according to claim 79, wherein the insulin derivative is $N^{\epsilon B29}$-dodecanoyl, des(B30) insulin.

94. The pharmaceutical composition according to claim 79, wherein the insulin derivative is in the form of a hexamer.

95. A method of treating diabetes in a patient in need of such a treatment, comprising administering to the patient a therapeutically effective amount of a pharmaceutical composition according to claim 79.

* * * * *

UNITED STATES PATENT AND TRADEMARK OFFICE
CERTIFICATE OF CORRECTION

PATENT NO. : 5,750,497
DATED : May 12, 1998
INVENTOR(S) : Havelund et al.

It is certified that error appears in the above-identified patent and that said Letters Patent is hereby corrected as shown below:

column 73, line 45: after "wherein", insert -- the -- column 73, line 45: delete both occurrences of "$Zn^2+$", and insert --$Zn^{2+}$-- column 73, line 47: delete "$Zn^2+$", and insert --$Zn^{2+}$-- column 75, line 6: "delete Bi", and insert --B1-- column 75, line 61: after "wherein", insert --the-- column 75, line 61: delete both occurrences of "$Zn^2+$", and insert --$Zn^{2+}$-- column 75, line 63: delete "$Zn^2+$", and insert --$Zn^{2+}$-- column 76, line 18: delete "position B13", and insert --position B1-- column 76, line 37: delete "lithocholoyl$\alpha$-glutamyl", and insert --lithocholoyl-$\alpha$-glutamyl-- column 77, line 8: delete "$Zn^2+$", and insert --$Zn^{2+}$--

Signed and Sealed this

Fifth Day of September, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Gly Ile Val Glu Gln Cys Cys Thr Ser Ile Cys Ser Leu Tyr Gln Leu
 1               5                  10                  15

Glu Asn Tyr Cys Xaa
             20
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Xaa Val Xaa Gln His Leu Cys Gly Ser His Leu Val Glu Ala Leu Tyr
 1               5                  10                  15

Leu Val Cys Gly Glu Arg Gly Phe Phe Tyr Thr Pro Lys Xaa
             20                  25                  30
```

( 2 ) INFORMATION FOR SEQ ID NO:3:

( i ) SEQUENCE CHARACTERISTICS:
    ( A ) LENGTH: 110 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

```
TGGCTAAGAG ATTCGTTGAC CAACACTTGT GCGGTTCTCA CTTGGTTGAA GCTTTGTACT         60
TGGTTTGTGG TGAAAGAGGT TTCTTCTACA CTCCAAAGTC TGACGACGCT                   110
```

( 2 ) INFORMATION FOR SEQ ID NO:4:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

```
CTGCGGGCTG CGTCTAAGCA CAGTAGTTTT CCAATTGGTA CAAAGAACAG ATAGAAGTAC         60
AACATTGTTC AACGATACCC TTAGCGTCGT CAGACTTGG                                100
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
GTCGCCATGG CTAAGAGATT CGTTG                                               25
```

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
CTGCTCTAGA GCCTGCGGGC TGCGTCT                                             27
```

( 2 ) INFORMATION FOR SEQ ID NO:7:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

```
TGGCTAAGAG ATTCGTTACT CAACACTTGT GCGGTTCTCA CTTGGTTGAA GCTTTGTACT         60
TGGTTTGTGG TGAAAGAGGT TTCTTCTACA CTCCAAAGTC TGACGACGCT                   110
```

( 2 ) INFORMATION FOR SEQ ID NO:8:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:8:

GTCGCCATGG CTAAGAGATT CGTTA    25

( 2 ) INFORMATION FOR SEQ ID NO:9:

( i ) SEQUENCE CHARACTERISTICS:
      ( A ) LENGTH: 100 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:9:

CTGCGGGCTG CGTCTAACCA CAGTAGTTTT CCAATTGGTA CAAAGAACAG ATAGAAGTAC    60

AACATTGTTC AACGATACCC TTAGCGTCGT CAGACTTTGG    100

( 2 ) INFORMATION FOR SEQ ID NO:10:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:10:

ACGTACGTTC TAGAGCCTGC GGGCTGC    27

( 2 ) INFORMATION FOR SEQ ID NO:11:

( i ) SEQUENCE CHARACTERISTICS:
      ( A ) LENGTH: 78 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:11:

CACTTGGTTG AAGCTTTGTA CTTGGTTTGT GGTGAAAGAG GTTCTTCTA CACTCCAAAG    60

ACTAGAGGTA TCGTTGAA    78

( 2 ) INFORMATION FOR SEQ ID NO:12:

( i ) SEQUENCE CHARACTERISTICS:
      ( A ) LENGTH: 63 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:12:

GCTAACGTCG CCATGGCTAA GAGAGAAGAA GCTGAAGCTG AAGCTAGATT CGTTAACCAA    60

CAC    63

( 2 ) INFORMATION FOR SEQ ID NO:13:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

```
GCTAACGTCG CCATGGCTAA GAGAGAAGAA GCTGAAGCGA AGCTGAAAGA TTCGTTAACC      60

AACAC                                                                  65
```

( 2 ) INFORMATION FOR SEQ ID NO:14:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 80..391

( x i ) SEQUENCE DESCRIPTION: SEQ ID NO:14:

```
ATCGAATTCC ATTCAAGAAT AGTTCAAACA AGAAGATTAC AAACTATCAA TTTCATACAC      60

AATATAAACG ACCAAAAGA ATG AAG GCT GTT TTC TTG GTT TTG TCC TTG ATC     112
                     Met Lys Ala Val Phe Leu Val Leu Ser Leu Ile
                      1               5                      10

GGA TTC TGC TGG GCC CAA CCA GTC ACT GGC GAT GAA TCA TCT GTT GAG      160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC      208
Ile Pro Glu Glu Ser Leu Ile Ile Ala Glu Asn Thr Thr Leu Ala Asn
         30                  35                  40

GTC GCC ATG GCT AAG AGA TTC GTT AAC CAA CAC TTG TGC GGT TCT CAC      256
Val Ala Met Ala Lys Arg Phe Val Asn Gln His Leu Cys Gly Ser His
     45                  50                  55

TTG GTT GAA GCT TTG TAC TTG GTT TGT GGT GAA AGA GGT TTC TTC TAC      304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT      352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT AAC TAGACGCAGC       401
Ser Ile Cys Ser Leu Tyr Gln Leu Glu Asn Tyr Cys Asn
             95                 100

CCGCAGGCTC TAGA                                                       415
```

( 2 ) INFORMATION FOR SEQ ID NO:15:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Lys Ala Val Phe Leu Val Leu Ser Leu Ile Gly Phe Cys Trp Ala
 1               5                  10                  15
```

```
Gln Pro Val Thr Gly Asp Glu Ser Ser Val Glu Ile Pro Glu Ser
             20                  25                  30

Leu Ile Ile Ala Glu Asn Thr Thr Leu Ala Asn Val Ala Met Ala Lys
         35                  40                  45

Arg Phe Val Asn Gln His Leu Cys Gly Ser His Leu Val Glu Ala Leu
     50                  55                  60

Tyr Leu Val Cys Gly Glu Arg Gly Phe Phe Tyr Thr Pro Lys Ser Asp
 65                  70                  75                  80

Asp Ala Lys Gly Ile Val Glu Gln Cys Cys Thr Ser Ile Cys Ser Leu
                 85                  90                  95

Tyr Gln Leu Glu Asn Tyr Cys Asn
                100
```

(2) INFORMATION FOR SEQ ID NO:16:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
TAGCTTAAGG TAAGTTCTTA TCAAGTTTGT TCTTCTAATG TTTGATAGTT AAAGTATGTG    60
TTATATTTGC TGGTTTTCTT ACTTCCGACA AAAGAACCAA AACAGGAACT AGCCTAAGAC   120
GACCCGGGTT GGTCAGTGAC CGCTACTTAG TAGACAACTC TAAGGCCTTC TCAGAGACTA   180
GTAGCGACTT TTGTGGTGAA ACCGATTGCA GCGGTACCGA TTCTCTAAGC AATTGGTTGT   240
GAACACGCCA AGAGTGAACC AACTTCGAAA CATGAACCAA ACACCACTTT CTCCAAAGAA   300
GATGTGAGGT TTCAGACTGC TGCGATTCCC ATAGCAACTT GTTACAACAT GAAGATAGAC   360
AAGAAACATG GTTAACCTTT TGATGACATT GATCTGCGTC GGGCGTCCGA GATCT        415
```

(2) INFORMATION FOR SEQ ID NO:17:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..499

(xi) SEQUENCE DESCRIPTION: SEQ ID NO:17:

```
ATCGAATTCC ATTCAAGAAT AGTTCAAACA AGAAGATTAC AAACTATCAA TTTCATACAC    60

AATATAAACG ATTAAAAGA ATG AGA TTT CCT TCA ATT TTT ACT GCA GTT TTA   112
                     Met Arg Phe Pro Ser Ile Phe Thr Ala Val Leu
                       1               5                      10

TTC GCA GCA TCC TCC GCA TTA GCT GCT CCA GTC AAC ACT ACA ACA GAA   160
Phe Ala Ala Ser Ser Ala Leu Ala Ala Pro Val Asn Thr Thr Thr Glu
             15                  20                  25

GAT GAA ACG GCA CAA ATT CCG GCT GAA GCT GTC ATC GGT TAC TCA GAT   208
Asp Glu Thr Ala Gln Ile Pro Ala Glu Ala Val Ile Gly Tyr Ser Asp
         30                  35                  40

TTA GAA GGG GAT TTC GAT GTT GCT GTT TTG CCA TTT TCC AAC AGC ACA   256
Leu Glu Gly Asp Phe Asp Val Ala Val Leu Pro Phe Ser Asn Ser Thr
 45                  50                  55
```

| AAT | AAC | GGG | TTA | TTG | TTT | ATA | AAT | ACT | ACT | ATT | GCC | AGC | ATT | GCT | GCT | 304 |
| Asn | Asn | Gly | Leu | Leu | Phe | Ile | Asn | Thr | Thr | Ile | Ala | Ser | Ile | Ala | Ala | |
| 60 | | | | | 65 | | | | 70 | | | | | | 75 | |
| AAA | GAA | GAA | GGG | GTA | TCT | TTG | GAT | AAG | AGA | GAA | GTT | AAC | CAA | CAC | TTG | 352 |
| Lys | Glu | Glu | Gly | Val | Ser | Leu | Asp | Lys | Arg | Glu | Val | Asn | Gln | His | Leu | |
| | | | | 80 | | | | | 85 | | | | | 90 | | |
| TGC | GGT | TCT | CAC | TTG | GTT | GAA | GCT | TTG | TAC | TTG | GTT | TGT | GGT | GAA | AGA | 400 |
| Cys | Gly | Ser | His | Leu | Val | Glu | Ala | Leu | Tyr | Leu | Val | Cys | Gly | Glu | Arg | |
| | | | 95 | | | | | | 100 | | | | | 105 | | |
| GGT | TTC | TTC | TAC | ACT | GAA | AAG | TCT | GAC | GAC | GCT | AAG | GGT | ATC | GTT | GAA | 448 |
| Gly | Phe | Phe | Tyr | Thr | Glu | Lys | Ser | Asp | Asp | Ala | Lys | Gly | Ile | Val | Glu | |
| | | 110 | | | | | 115 | | | | | 120 | | | | |
| CAA | TGT | TGT | ACT | TCT | ATC | TGT | TCT | TTG | TAC | CAA | TTG | GAA | AAC | TAC | TGT | 496 |
| Gln | Cys | Cys | Thr | Ser | Ile | Cys | Ser | Leu | Tyr | Gln | Leu | Glu | Asn | Tyr | Cys | |
| | 125 | | | | | 130 | | | | | | 135 | | | | |
| AAC | TAGACGCAGC | | CCGCAGGCTC | | TAGA | | | | | | | | | | | 523 |
| Asn | | | | | | | | | | | | | | | | |
| 140 | | | | | | | | | | | | | | | | |

( 2 ) INFORMATION FOR SEQ ID NO:18:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Met | Arg | Phe | Pro | Ser | Ile | Phe | Thr | Ala | Val | Leu | Phe | Ala | Ala | Ser | Ser |
| 1 | | | | 5 | | | | | 10 | | | | | 15 | |
| Ala | Leu | Ala | Ala | Pro | Val | Asn | Thr | Thr | Glu | Asp | Glu | Thr | Ala | Gln | |
| | | | 20 | | | | | 25 | | | | | 30 | | |
| Ile | Pro | Ala | Glu | Ala | Val | Ile | Gly | Tyr | Ser | Asp | Leu | Glu | Gly | Asp | Phe |
| | | 35 | | | | | 40 | | | | | 45 | | | |
| Asp | Val | Ala | Val | Leu | Pro | Phe | Ser | Asn | Ser | Thr | Asn | Asn | Gly | Leu | Leu |
| | 50 | | | | | 55 | | | | | 60 | | | | |
| Phe | Ile | Asn | Thr | Thr | Ile | Ala | Ser | Ile | Ala | Ala | Lys | Glu | Glu | Gly | Val |
| 65 | | | | | 70 | | | | | 75 | | | | | 80 |
| Ser | Leu | Asp | Lys | Arg | Glu | Val | Asn | Gln | His | Leu | Cys | Gly | Ser | His | Leu |
| | | | | 85 | | | | | 90 | | | | | 95 | |
| Val | Glu | Ala | Leu | Tyr | Leu | Val | Cys | Gly | Glu | Arg | Gly | Phe | Phe | Tyr | Thr |
| | | | 100 | | | | | 105 | | | | | 110 | | |
| Glu | Lys | Ser | Asp | Asp | Ala | Lys | Gly | Ile | Val | Glu | Gln | Cys | Cys | Thr | Ser |
| | | 115 | | | | | 120 | | | | | 125 | | | |
| Ile | Cys | Ser | Leu | Tyr | Gln | Leu | Glu | Asn | Tyr | Cys | Asn | | | | |
| | 130 | | | | | 135 | | | | | 140 | | | | |

( 2 ) INFORMATION FOR SEQ ID NO:19:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

| TAGCTTAAGG | TAAGTTCTTA | TCAAGTTTGT | TCTTCTAATG | TTTGATAGTT | AAAGTATGTG | 60 |
| TTATATTTGC | TAATTTTCTT | ACTCTAAAGG | AAGTTAAAAA | TGACGTCAAA | ATAAGCGTCG | 120 |

| | | | | |
|---|---|---|---|---|
| TAGGAGGCGT | AATCGACGAG | GTCAGTTGTG | ATGTTGTCTT | CTACTTTGCC | GTGTTTAAGG | 180 |
| CCGACTTCGA | CAGTAGCCAA | TGAGTCTAAA | TCTTCCCCTA | AAGCTACAAC | GACAAAACGG | 240 |
| TAAAAGGTTG | TCGTGTTTAT | TGCCCAATAA | CAAATATTTA | TGATGATAAC | GGTCGTAACG | 300 |
| ACGATTTCTT | CTTCCCCATA | GAAACCTATT | CTCTCTTCAA | TTGGTTGTGA | ACACGCCAAG | 360 |
| AGTGAACCAA | CTTCGAAACA | TGAACCAAAC | ACCACTTTCT | CCAAAGAAGA | TGTGACTTTT | 420 |
| CAGACTGCTG | CGATTCCCAT | AGCAACTTGT | TACAACATGA | AGATAGACAA | GAAACATGGT | 480 |
| TAACCTTTTG | ATGACATTGA | TCTGCGTCGG | GCGTCCGAGA | TCT | | 523 |

( 2 ) INFORMATION FOR SEQ ID NO:20:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 80..391

( x i ) SEQUENCE DESCRIPTION: SEQ ID NO:20:

```
ATCGAATTCC ATTCAAGAAT AGTTCAAACA AGAAGATTAC AAACTATCAA TTTCATACAC         60

AATATAAACG ACCAAAAGA ATG AAG GCT GTT TTC TTG GTT TTG TCC TTG ATC         112
                       Met Lys Ala Val Phe Leu Val Leu Ser Leu Ile
                        1               5                      10

GGA TTC TGC TGG GCC CAA CCA GTC ACT GGC GAT GAA TCA TCT GTT GAG          160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC          208
Ile Pro Glu Glu Ser Leu Ile Ile Ala Glu Asn Thr Thr Leu Ala Asn
         30                  35                  40

GTC GCC ATG GCT AAG AGA TTC GTT GAC CAA CAC TTG TGC GGT TCT CAC          256
Val Ala Met Ala Lys Arg Phe Val Asp Gln His Leu Cys Gly Ser His
     45                  50                      55

TTG GTT GAA GCT TTG TAC TTG GTT TGT GGT GAA AGA GGT TTC TTC TAC          304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT          352
Thr Pro Lys Ser Asp Asp Ala Lys Gly Ile Val Glu Gln Cys Cys Thr
             80                  85                      90

TCT ATC TGT TCT TTG TAC CAA TTG GAA AAC TAC TGT GCT TAGACGCAGC          401
Ser Ile Cys Ser Leu Tyr Gln Leu Glu Asn Tyr Cys Ala
             95              100

CCGCAGGCTC TAGA                                                          415
```

( 2 ) INFORMATION FOR SEQ ID NO:21:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
             20                  25                  30
```

```
        Leu  Ile  Ile  Ala  Glu  Asn  Thr  Thr  Leu  Ala  Asn  Val  Ala  Met  Ala  Lys
                  35                      40                           45

Arg  Phe  Val  Asp  Gln  His  Leu  Cys  Gly  Ser  His  Leu  Val  Glu  Ala  Leu
             50                      55                           60

Tyr  Leu  Val  Cys  Gly  Glu  Arg  Gly  Phe  Phe  Tyr  Thr  Pro  Lys  Ser  Asp
        65                      70                      75                           80

Asp  Ala  Lys  Gly  Ile  Val  Glu  Gln  Cys  Cys  Thr  Ser  Ile  Cys  Ser  Leu
                            85                      90                      95

Tyr  Gln  Leu  Glu  Asn  Tyr  Cys  Ala
                       100
```

( 2 ) INFORMATION FOR SEQ ID NO:22:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

```
TAGCTTAAGG  TAAGTTCTTA  TCAAGTTTGT  TCTTCTAATG  TTTGATAGTT  AAAGTATGTG      60

TTATATTTGC  TGGTTTTCTT  ACTTCCGACA  AAAGAACCAA  AACAGGAACT  AGCCTAAGAC     120

GACCCGGGTT  GGTCAGTGAC  CGCTACTTAG  TAGACAACTC  TAAGGCCTTC  TCAGAGACTA     180

GTAGCGACTT  TTGTGGTGAA  ACCGATTGCA  GCGGTACCGA  TTCTCTAAGC  AACTGGTTGT     240

GAACACGCCA  AGAGTGAACC  AACTTCGAAA  CATGAACCAA  ACACCACTTT  CTCCAAAGAA     300

GATGTGAGGT  TTCAGACTGC  TGCGATTCCC  ATAGCAACTT  GTTACAACAT  GAAGATAGAC     360

AAGAAACATG  GTTAACCTTT  TGATGACACG  AATCTGCGTC  GGGCGTCCGA  GATCT           415
```

( 2 ) INFORMATION FOR SEQ ID NO:23:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 80..391

( x i ) SEQUENCE DESCRIPTION: SEQ ID NO:23:

```
ATCGAATTCC  ATTCAAGAAT  AGTTCAAACA  AGAAGATTAC  AAACTATCAA  TTTCATACAC      60

AATATAAACG  ACCAAAAGA  ATG  AAG  GCT  GTT  TTC  TTG  GTT  TTG  TCC  TTG  ATC     112
                        Met  Lys  Ala  Val  Phe  Leu  Val  Leu  Ser  Leu  Ile
                         1                 5                          10

GGA  TTC  TGC  TGG  GCC  CAA  CCA  GTC  ACT  GGC  GAT  GAA  TCA  TCT  GTT  GAG     160
Gly  Phe  Cys  Trp  Ala  Gln  Pro  Val  Thr  Gly  Asp  Glu  Ser  Ser  Val  Glu
               15                      20                      25

ATT  CCG  GAA  GAG  TCT  CTG  ATC  ATC  GCT  GAA  AAC  ACC  ACT  TTG  GCT  AAC     208
Ile  Pro  Glu  Glu  Ser  Leu  Ile  Ile  Ala  Glu  Asn  Thr  Thr  Leu  Ala  Asn
          30                      35                      40

GTC  GCC  ATG  GCT  AAG  AGA  TTC  GTT  ACT  CAA  CAC  TTG  TGC  GGT  TCT  CAC     256
Val  Ala  Met  Ala  Lys  Arg  Phe  Val  Thr  Gln  His  Leu  Cys  Gly  Ser  His
     45                      50                      55

TTG  GTT  GAA  GCT  TTG  TAC  TTG  GTT  TGT  GGT  GAA  AGA  GGT  TTC  TTC  TAC     304
Leu  Val  Glu  Ala  Leu  Tyr  Leu  Val  Cys  Gly  Glu  Arg  Gly  Phe  Phe  Tyr
```

|   |   |   |   |   |   |   |   |   |   |   |   |   |   |   |   |   |
|---|---|---|---|---|---|---|---|---|---|---|---|---|---|---|---|---|
| | | 60 | | | | | 65 | | | | | 70 | | | | 75 |

```
ACT  CCA  AAG  TCT  GAC  GAC  GCT  AAG  GGT  ATC  GTT  GAA  CAA  TGT  TGT  ACT       352
Thr  Pro  Lys  Ser  Asp  Asp  Ala  Lys  Gly  Ile  Val  Glu  Gln  Cys  Cys  Thr
                    80                       85                       90

TCT  ATC  TGT  TCT  TTG  TAC  CAA  TTG  GAA  AAC  TAC  TGT  GCT  TAGACGCAGC          401
Ser  Ile  Cys  Ser  Leu  Tyr  Gln  Leu  Glu  Asn  Tyr  Cys  Ala
                    95                       100

CCGCAGGCTC  TAGA                                                                      415
```

( 2 ) INFORMATION FOR SEQ ID NO:24:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met  Lys  Ala  Val  Phe  Leu  Val  Leu  Ser  Leu  Ile  Gly  Phe  Cys  Trp  Ala
 1              5                    10                       15

Gln  Pro  Val  Thr  Gly  Asp  Glu  Ser  Ser  Val  Glu  Ile  Pro  Glu  Glu  Ser
               20                    25                       30

Leu  Ile  Ile  Ala  Glu  Asn  Thr  Thr  Leu  Ala  Asn  Val  Ala  Met  Ala  Lys
               35                    40                       45

Arg  Phe  Val  Thr  Gln  His  Leu  Cys  Gly  Ser  His  Leu  Val  Glu  Ala  Leu
      50                         55                       60

Tyr  Leu  Val  Cys  Gly  Glu  Arg  Gly  Phe  Phe  Tyr  Thr  Pro  Lys  Ser  Asp
 65                        70                    75                       80

Asp  Ala  Lys  Gly  Ile  Val  Glu  Gln  Cys  Cys  Thr  Ser  Ile  Cys  Ser  Leu
                    85                       90                       95

Tyr  Gln  Leu  Glu  Asn  Tyr  Cys  Ala
                    100
```

( 2 ) INFORMATION FOR SEQ ID NO:25:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

```
TAGCTTAAGG  TAAGTTCTTA  TCAAGTTTGT  TCTTCTAATG  TTTGATAGTT  AAAGTATGTG    60

TTATATTTGC  TGGTTTTCTT  ACTTCCGACA  AAAGAACCAA  AACAGGAACT  AGCCTAAGAC   120

GACCCGGGTT  GGTCAGTGAC  CGCTACTTAG  TAGACAACTC  TAAGGCCTTC  TCAGAGACTA   180

GTAGCGACTT  TTGTGGTGAA  ACCGATTGCA  GCGGTACCGA  TTCTCTAAGC  AATGAGTTGT   240

GAACACGCCA  AGAGTGAACC  AACTTCGAAA  CATGAACCAA  ACACCACTTT  CTCCAAAGAA   300

GATGTGAGGT  TTCAGACTGC  TGCGATTCCC  ATAGCAACTT  GTTACAACAT  GAAGATAGAC   360

AAGAAACATG  GTTAACCTTT  TGATGACACG  AATCTGCGTC  GGGCGTCCGA  GATCT        415
```

( 2 ) INFORMATION FOR SEQ ID NO:26:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
(A) NAME/KEY: CDS
(B) LOCATION: 80..391

( x i ) SEQUENCE DESCRIPTION: SEQ ID NO:26:

| ATCGAATTCC | ATTCAAGAAT | AGTTCAAACA | AGAAGATTAC | AAACTATCAA | TTTCATACAC | 60 |

| AATATAAACG | ACCAAAAGA | ATG | AAG | GCT | GTT | TTC | TTG | GTT | TTG | TCC | TTG | ATC | 112 |
|  |  | Met | Lys | Ala | Val | Phe | Leu | Val | Leu | Ser | Leu | Ile |  |
|  |  | 1 |  | 5 |  |  |  |  |  |  |  | 10 |  |

| GGA | TTC | TGC | TGG | GCC | CAA | CCA | GTC | ACT | GGC | GAT | GAA | TCA | TCT | GTT | GAG | 160 |
| Gly | Phe | Cys | Trp | Ala | Gln | Pro | Val | Thr | Gly | Asp | Glu | Ser | Ser | Val | Glu |  |
|  |  |  | 15 |  |  |  |  | 20 |  |  |  |  | 25 |  |  |  |

| ATT | CCG | GAA | GAG | TCT | CTG | ATC | ATC | GCT | GAA | AAC | ACC | ACT | TTG | GCT | AAC | 208 |
| Ile | Pro | Glu | Glu | Ser | Leu | Ile | Ile | Ala | Glu | Asn | Thr | Thr | Leu | Ala | Asn |  |
|  |  | 30 |  |  |  |  | 35 |  |  |  |  | 40 |  |  |  |  |

| GTC | GCC | ATG | GCT | AAG | AGA | TTC | GTT | GAC | CAA | CAC | TTG | TGC | GGT | TCT | CAC | 256 |
| Val | Ala | Met | Ala | Lys | Arg | Phe | Val | Asp | Gln | His | Leu | Cys | Gly | Ser | His |  |
|  | 45 |  |  |  |  | 50 |  |  |  |  | 55 |  |  |  |  |  |

| TTG | GTT | GAA | GCT | TTG | TAC | TTG | GTT | TGT | GGT | GAA | AGA | GGT | TTC | TTC | TAC | 304 |
| Leu | Val | Glu | Ala | Leu | Tyr | Leu | Val | Cys | Gly | Glu | Arg | Gly | Phe | Phe | Tyr |  |
| 60 |  |  |  |  | 65 |  |  |  |  | 70 |  |  |  |  | 75 |  |

| ACT | CCA | AAG | TCT | GAC | GAC | GCT | AAG | GGT | ATC | GTT | GAA | CAA | TGT | TGT | ACT | 352 |
| Thr | Pro | Lys | Ser | Asp | Asp | Ala | Lys | Gly | Ile | Val | Glu | Gln | Cys | Cys | Thr |  |
|  |  |  |  | 80 |  |  |  |  | 85 |  |  |  |  | 90 |  |  |

| TCT | ATC | TGT | TCT | TTG | TAC | CAA | TTG | GAA | AAC | TAC | TGT | GGT | TAGACGCAGC | 401 |
| Ser | Ile | Cys | Ser | Leu | Tyr | Gln | Leu | Glu | Asn | Tyr | Cys | Gly |  |  |
|  |  |  | 95 |  |  |  |  | 100 |  |  |  |  |  |  |

| CCGCAGGCTC | TAGA | 415 |

( 2 ) INFORMATION FOR SEQ ID NO:27:

( i ) SEQUENCE CHARACTERISTICS:
(A) LENGTH: 104 amino acids
(B) TYPE: amino acid
(D) TOPOLOGY: linear ( i i ) MOLECULE TYPE: protein ( x i ) SEQUENCE DESCRIPTION: SEQ ID NO:27:

| Met | Lys | Ala | Val | Phe | Leu | Val | Leu | Ser | Leu | Ile | Gly | Phe | Cys | Trp | Ala |
| 1 |  |  |  | 5 |  |  |  |  | 10 |  |  |  |  | 15 |  |

| Gln | Pro | Val | Thr | Gly | Asp | Glu | Ser | Ser | Val | Glu | Ile | Pro | Glu | Glu | Ser |
|  |  |  | 20 |  |  |  |  | 25 |  |  |  |  | 30 |  |  |

| Leu | Ile | Ile | Ala | Glu | Asn | Thr | Thr | Leu | Ala | Asn | Val | Ala | Met | Ala | Lys |
|  |  |  | 35 |  |  |  |  | 40 |  |  |  |  | 45 |  |  |

| Arg | Phe | Val | Asp | Gln | His | Leu | Cys | Gly | Ser | His | Leu | Val | Glu | Ala | Leu |
|  | 50 |  |  |  |  | 55 |  |  |  |  | 60 |  |  |  |  |

| Tyr | Leu | Val | Cys | Gly | Glu | Arg | Gly | Phe | Phe | Tyr | Thr | Pro | Lys | Ser | Asp |
| 65 |  |  |  |  | 70 |  |  |  |  | 75 |  |  |  |  | 80 |

| Asp | Ala | Lys | Gly | Ile | Val | Glu | Gln | Cys | Cys | Thr | Ser | Ile | Cys | Ser | Leu |
|  |  |  |  | 85 |  |  |  |  | 90 |  |  |  |  | 95 |  |

| Tyr | Gln | Leu | Glu | Asn | Tyr | Cys | Gly |
|  |  |  | 100 |  |  |  |  |

( 2 ) INFORMATION FOR SEQ ID NO:28:

( i ) SEQUENCE CHARACTERISTICS:
(A) LENGTH: 415 base pairs
(B) TYPE: nucleic acid (C) STRANDEDNESS: single
(D) TOPOLOGY: linear (ii) MOLECULE TYPE: DNA (xi) SEQUENCE DESCRIPTION: SEQ ID NO:28:

```
TAGCTTAAGG TAAGTTCTTA TCAAGTTTGT TCTTCTAATG TTTGATAGTT AAAGTATGTG    60
TTATATTTGC TGGTTTTCTT ACTTCCGACA AAAGAACCAA AACAGGAACT AGCCTAAGAC   120
GACCCGGGTT GGTCAGTGAC CGCTACTTAG TAGACAACTC TAAGGCCTTC TCAGAGACTA   180
GTAGCGACTT TTGTGGTGAA ACCGATTGCA GCGGTACCGA TTCTCTAAGC AACTGGTTGT   240
GAACACGCCA AGAGTGAACC AACTTCGAAA CATGAACCAA ACACCACTTT CTCCAAAGAA   300
GATGTGAGGT TTCAGACTGC TGCGATTCCC ATAGCAACTT GTTACAACAT GAAGATAGAC   360
AAGAAACATG GTTAACCTTT TGATGACACC AATCTGCGTC GGGCGTCCGA GATCT        415
```

(2) INFORMATION FOR SEQ ID NO:29:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..391

(xi) SEQUENCE DESCRIPTION: SEQ ID NO:29:

```
ATCGAATTCC ATTCAAGAAT AGTTCAAACA GAAGATTAC AAACTATCAA TTTCATACAC     60

AATATAAACG ACCAAAAGA ATG AAG GCT GTT TTC TTG GTT TTG TCC TTG ATC    112
                     Met Lys Ala Val Phe Leu Val Leu Ser Leu Ile
                       1               5                      10

GGA TTC TGC TGG GCC CAA CCA GTC ACT GGC GAT GAA TCA TCT GTT GAG    160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC    208
Ile Pro Glu Glu Ser Leu Ile Ile Ala Glu Asn Thr Thr Leu Ala Asn
         30                  35                  40

GTC GCC ATG GCT AAG AGA TTC GTT ACT CAA CAC TTG TGC GGT TCT CAC    256
Val Ala Met Ala Lys Arg Phe Val Thr Gln His Leu Cys Gly Ser His
     45                  50                  55

TTG GTT GAA GCT TTG TAC TTG GTT TGT GGT GAA AGA GGT TTC TTC TAC    304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT    352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT GGT TAGACGCAGC     401
Ser Ile Cys Ser Leu Tyr Gln Leu Glu Asn Tyr Cys Gly
             95                 100

CCGCAGGCTC TAGA                                                      415
```

(2) INFORMATION FOR SEQ ID NO:30:

(i) SEQUENCE CHARACTERISTICS:
        (A) LENGTH: 104 amino acids
        (B) TYPE: amino acid
        (D) TOPOLOGY: linear (ii) MOLECULE TYPE: protein ( x i ) SEQUENCE DESCRIPTION: SEQ ID NO:30:

```
Met Lys Ala Val Phe Leu Val Leu Ser Leu Ile Gly Phe Cys Trp Ala
  1               5                  10                      15

Gln Pro Val Thr Gly Asp Glu Ser Ser Val Glu Ile Pro Glu Glu Ser
             20                  25                  30

Leu Ile Ile Ala Glu Asn Thr Thr Leu Ala Asn Val Ala Met Ala Lys
         35                  40                  45

Arg Phe Val Thr Gln His Leu Cys Gly Ser His Leu Val Glu Ala Leu
     50                  55                  60

Tyr Leu Val Cys Gly Glu Arg Gly Phe Phe Tyr Thr Pro Lys Ser Asp
 65                  70                  75                  80

Asp Ala Lys Gly Ile Val Glu Gln Cys Cys Thr Ser Ile Cys Ser Leu
                 85                  90                  95

Tyr Gln Leu Glu Asn Tyr Cys Gly
                100
```

( 2 ) INFORMATION FOR SEQ ID NO:31:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

```
TAGCTTAAGG TAAGTTCTTA TCAAGTTTGT TCTTCTAATG TTTGATAGTT AAAGTATGTG    60

TTATATTTGC TGGTTTTCTT ACTTCCGACA AAAGAACCAA AACAGGAACT AGCCTAAGAC   120

GACCCGGGTT GGTCAGTGAC CGCTACTTAG TAGACAACTC TAAGGCCTTC TCAGAGACTA   180

GTAGCGACTT TTGTGGTGAA ACCGATTGCA GCGGTACCGA TTCTCTAAGC AATGAGTTGT   240

GAACACGCCA AGAGTGAACC AACTTCGAAA CATGAACCAA ACACCACTTT CTCCAAAGAA   300

GATGTGAGGT TTCAGACTGC TGCGATTCCC ATAGCAACTT GTTACAACAT GAAGATAGAC   360

AAGAAACATG GTTAACCTTT TGATGACACC AATCTGCGTC GGGCGTCCGA GATCT        415
```

( 2 ) INFORMATION FOR SEQ ID NO:32:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 80..499

( x i ) SEQUENCE DESCRIPTION: SEQ ID NO:32:

```
ATCGAATTCC ATTCAAGAAT AGTTCAAACA AGAAGATTAC AAACTATCAA TTTCATACAC     60

AATATAAACG ATTAAAAGA ATG AGA TTT CCT TCA ATT TTT ACT GCA GTT TTA    112
                     Met Arg Phe Pro Ser Ile Phe Thr Ala Val Leu
                      1               5                      10

TTC GCA GCA TCC TCC GCA TTA GCT GCT CCA GTC AAC ACT ACA ACA GAA    160
Phe Ala Ala Ser Ser Ala Leu Ala Ala Pro Val Asn Thr Thr Thr Glu
             15                  20                  25

GAT GAA ACG GCA CAA ATT CCG GCT GAA GCT GTC ATC GGT TAC TCA GAT    208
Asp Glu Thr Ala Gln Ile Pro Ala Glu Ala Val Ile Gly Tyr Ser Asp
         30                  35                  40
```

| | | | | | | | | | | | | | | | | |
|---|---|---|---|---|---|---|---|---|---|---|---|---|---|---|---|---|
| TTA | GAA | GGG | GAT | TTC | GAT | GTT | GCT | GTT | TTG | CCA | TTT | TCC | AAC | AGC | ACA | 256 |
| Leu | Glu | Gly | Asp | Phe | Asp | Val | Ala | Val | Leu | Pro | Phe | Ser | Asn | Ser | Thr | |
| | 45 | | | | 50 | | | | | 55 | | | | | | |
| AAT | AAC | GGG | TTA | TTG | TTT | ATA | AAT | ACT | ACT | ATT | GCC | AGC | ATT | GCT | GCT | 304 |
| Asn | Asn | Gly | Leu | Leu | Phe | Ile | Asn | Thr | Thr | Ile | Ala | Ser | Ile | Ala | Ala | |
| 60 | | | | | 65 | | | | 70 | | | | | | 75 | |
| AAA | GAA | GAA | GGG | GTA | TCT | TTG | GAT | AAG | AGA | TTC | GTT | AAC | CAA | CAC | TTG | 352 |
| Lys | Glu | Glu | Gly | Val | Ser | Leu | Asp | Lys | Arg | Phe | Val | Asn | Gln | His | Leu | |
| | | | 80 | | | | | 85 | | | | | | 90 | | |
| TGC | GGT | TCT | CAC | TTG | GTT | GAA | GCT | TTG | TAC | TTG | GTT | TGT | GGT | GAA | AGA | 400 |
| Cys | Gly | Ser | His | Leu | Val | Glu | Ala | Leu | Tyr | Leu | Val | Cys | Gly | Glu | Arg | |
| | | | 95 | | | | | 100 | | | | | 105 | | | |
| GGT | TTC | TTC | TAC | ACT | CCA | AAG | TCT | GAC | GAC | GCT | AAG | GGT | ATC | GTT | GAA | 448 |
| Gly | Phe | Phe | Tyr | Thr | Pro | Lys | Ser | Asp | Asp | Ala | Lys | Gly | Ile | Val | Glu | |
| | | 110 | | | | | 115 | | | | | 120 | | | | |
| CAA | TGT | TGT | ACT | TCT | ATC | TGT | TCT | TTG | TAC | CAA | TTG | GAA | AAC | TAC | TGT | 496 |
| Gln | Cys | Cys | Thr | Ser | Ile | Cys | Ser | Leu | Tyr | Gln | Leu | Glu | Asn | Tyr | Cys | |
| | 125 | | | | 130 | | | | | 135 | | | | | | |
| AAC | TAGACGCAGC | CCGCAGGCTC | TAGA | | | | | | | | | | | | | 523 |
| Asn | | | | | | | | | | | | | | | | |
| 140 | | | | | | | | | | | | | | | | |

( 2 ) INFORMATION FOR SEQ ID NO:33:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | | | | | |
|---|---|---|---|---|---|---|---|---|---|---|---|---|---|---|---|
| Met | Arg | Phe | Pro | Ser | Ile | Phe | Thr | Ala | Val | Leu | Phe | Ala | Ala | Ser | Ser |
| 1 | | | | 5 | | | | | 10 | | | | | 15 | |
| Ala | Leu | Ala | Ala | Pro | Val | Asn | Thr | Thr | Thr | Glu | Asp | Glu | Thr | Ala | Gln |
| | | | 20 | | | | | 25 | | | | | 30 | | |
| Ile | Pro | Ala | Glu | Ala | Val | Ile | Gly | Tyr | Ser | Asp | Leu | Glu | Gly | Asp | Phe |
| | | 35 | | | | | 40 | | | | | 45 | | | |
| Asp | Val | Ala | Val | Leu | Pro | Phe | Ser | Asn | Ser | Thr | Asn | Asn | Gly | Leu | Leu |
| | 50 | | | | | 55 | | | | | 60 | | | | |
| Phe | Ile | Asn | Thr | Thr | Ile | Ala | Ser | Ile | Ala | Ala | Lys | Glu | Glu | Gly | Val |
| 65 | | | | | 70 | | | | | 75 | | | | | 80 |
| Ser | Leu | Asp | Lys | Arg | Phe | Val | Asn | Gln | His | Leu | Cys | Gly | Ser | His | Leu |
| | | | | 85 | | | | | 90 | | | | | 95 | |
| Val | Glu | Ala | Leu | Tyr | Leu | Val | Cys | Gly | Glu | Arg | Gly | Phe | Phe | Tyr | Thr |
| | | | 100 | | | | | 105 | | | | | 110 | | |
| Pro | Lys | Ser | Asp | Asp | Ala | Lys | Gly | Ile | Val | Glu | Gln | Cys | Cys | Thr | Ser |
| | | 115 | | | | | 120 | | | | | 125 | | | |
| Ile | Cys | Ser | Leu | Tyr | Gln | Leu | Glu | Asn | Tyr | Cys | Asn | | | | |
| | 130 | | | | | 135 | | | | | 140 | | | | |

( 2 ) INFORMATION FOR SEQ ID NO:34:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

```
TAGCTTAAGG  TAAGTTCTTA  TCAAGTTTGT  TCTTCTAATG  TTTGATAGTT  AAAGTATGTG      60

TTATATTTGC  TAATTTTCTT  ACTCTAAAGG  AAGTTAAAAA  TGACGTCAAA  ATAAGCGTCG     120

TAGGAGGCGT  AATCGACGAG  GTCAGTTGTG  ATGTTGTCTT  CTACTTTGCC  GTGTTAAGG     180

CCGACTTCGA  CAGTAGCCAA  TGAGTCTAAA  TCTTCCCCTA  AAGCTACAAC  GACAAACGG     240

TAAAAGGTTG  TCGTGTTTAT  TGCCCAATAA  CAAATATTTA  TGATGATAAC  GGTCGTAACG     300

ACGATTTCTT  CTTCCCCATA  GAAACCTATT  CTCTAAGCAA  TTGGTTGTGA  ACACGCCAAG    360

AGTGAACCAA  CTTCGAAACA  TGAACCAAAC  ACCACTTTCT  CCAAAGAAGA  TGTGAGGTTT    420

CAGACTGCTG  CGATTCCCAT  AGCAACTTGT  TACAACATGA  AGATAGACAA  GAAACATGGT    480

TAACCTTTTG  ATGACATTGA  TCTGCGTCGG  GCGTCCGAGA  TCT                        523
```

(2) INFORMATION FOR SEQ ID NO:35:

(i) SEQUENCE CHARACTERISTICS:
    (A) LENGTH: 409 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 80..385

(xi) SEQUENCE DESCRIPTION: SEQ ID NO:35:

```
ATCGAATTCC  ATTCAAGAAT  AGTTCAAACA  AGAAGATTAC  AAACTATCAA  TTTCATACAC      60

AATATAAACG  ACCAAAAGA  ATG  AAG  GCT  GTT  TTC  TTG  GTT  TTG  TCC  TTG  ATC    112
                           Met  Lys  Ala  Val  Phe  Leu  Val  Leu  Ser  Leu  Ile
                             1                5                        10

GGA  TTC  TGC  TGG  GCC  CAA  CCA  GTC  ACT  GGC  GAT  GAA  TCA  TCT  GTT  GAG    160
Gly  Phe  Cys  Trp  Ala  Gln  Pro  Val  Thr  Gly  Asp  Glu  Ser  Ser  Val  Glu
              15                   20                   25

ATT  CCG  GAA  GAG  TCT  CTG  ATC  ATC  GCT  GAA  AAC  ACC  ACT  TTG  GCT  AAC    208
Ile  Pro  Glu  Glu  Ser  Leu  Ile  Ile  Ala  Glu  Asn  Thr  Thr  Leu  Ala  Asn
         30                        35                        40

GTC  GCC  ATG  GCT  AAG  AGA  TTC  GTT  AAC  CAA  CAC  TTG  TGC  GGT  TCT  CAC    256
Val  Ala  Met  Ala  Lys  Arg  Phe  Val  Asn  Gln  His  Leu  Cys  Gly  Ser  His
         45                        50                        55

TTG  GTT  GAA  GCT  TTG  TAC  TTG  GTT  TGT  GGT  GAA  AGA  GGT  TTC  TTC  TAC    304
Leu  Val  Glu  Ala  Leu  Tyr  Leu  Val  Cys  Gly  Glu  Arg  Gly  Phe  Phe  Tyr
 60                        65                        70                   75

ACT  CCT  AAG  GAA  AAG  AGA  GGT  ATC  GTT  GAA  CAA  TGT  TGT  ACT  TCT  ATC    352
Thr  Pro  Lys  Glu  Lys  Arg  Gly  Ile  Val  Glu  Gln  Cys  Cys  Thr  Ser  Ile
              80                        85                        90

TGT  TCT  TTG  TAC  CAA  TTG  GAA  AAC  TAC  TGT  GGT  TAGACGCAGC  CCGCAGGCTC    405
Cys  Ser  Leu  Tyr  Gln  Leu  Glu  Asn  Tyr  Cys  Gly
              95                       100

TAGA                                                                        409
```

(2) INFORMATION FOR SEQ ID NO:36:

(i) SEQUENCE CHARACTERISTICS:
    (A) LENGTH: 102 amino acids
    (B) TYPE: amino acid
    (D) TOPOLOGY: linear (ii) MOLECULE TYPE: protein (xi) SEQUENCE DESCRIPTION: SEQ ID NO:36:

| Met | Lys | Ala | Val | Phe | Leu | Val | Leu | Ser | Leu | Ile | Gly | Phe | Cys | Trp | Ala |
|---|---|---|---|---|---|---|---|---|---|---|---|---|---|---|---|
| 1 | | | | 5 | | | | | 10 | | | | | 15 | |

| Gln | Pro | Val | Thr | Gly | Asp | Glu | Ser | Ser | Val | Glu | Ile | Pro | Glu | Ser |
|---|---|---|---|---|---|---|---|---|---|---|---|---|---|---|
| | | | 20 | | | | 25 | | | | | 30 | | |

| Leu | Ile | Ile | Ala | Glu | Asn | Thr | Thr | Leu | Ala | Asn | Val | Ala | Met | Ala | Lys |
|---|---|---|---|---|---|---|---|---|---|---|---|---|---|---|---|
| | | 35 | | | | | 40 | | | | | 45 | | | |

| Arg | Phe | Val | Asn | Gln | His | Leu | Cys | Gly | Ser | His | Leu | Val | Glu | Ala | Leu |
|---|---|---|---|---|---|---|---|---|---|---|---|---|---|---|---|
| | 50 | | | | | 55 | | | | | 60 | | | | |

| Tyr | Leu | Val | Cys | Gly | Glu | Arg | Gly | Phe | Phe | Tyr | Thr | Pro | Lys | Glu | Lys |
|---|---|---|---|---|---|---|---|---|---|---|---|---|---|---|---|
| 65 | | | | | 70 | | | | | 75 | | | | | 80 |

| Arg | Gly | Ile | Val | Glu | Gln | Cys | Cys | Thr | Ser | Ile | Cys | Ser | Leu | Tyr | Gln |
|---|---|---|---|---|---|---|---|---|---|---|---|---|---|---|---|
| | | | | 85 | | | | | 90 | | | | | 95 | |

| Leu | Glu | Asn | Tyr | Cys | Gly |
|---|---|---|---|---|---|
| | | | 100 | | |

(2) INFORMATION FOR SEQ ID NO:37:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

```
TAGCTTAAGG TAAGTTCTTA TCAAGTTTGT TCTTCTAATG TTTGATAGTT AAAGTATGTG      60
TTATATTTGC TGGTTTTCTT ACTTCCGACA AAAGAACCAA AACAGGAACT AGCCTAAGAC     120
GACCCGGGTT GGTCAGTGAC CGCTACTTAG TAGACAACTC TAAGGCCTTC TCAGAGACTA     180
GTAGCGACTT TTGTGGTGAA ACCGATTGCA GCGGTACCGA TTCTCTAAGC AATTGGTTGT     240
GAACACGCCA AGAGTGAACC AACTTCGAAA CATGAACCAA ACACCACTTT CTCCAAAGAA     300
GATGTGAGGA TTCCTTTTCT CTCCATAGCA ACTTGTTACA ACATGAAGAT AGACAAGAAA     360
CATGGTTAAC CTTTTGATGA CACCAATCTG CGTCGGGCGT CCGAGATCT               409
```

(2) INFORMATION FOR SEQ ID NO:38:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..487

(xi) SEQUENCE DESCRIPTION: SEQ ID NO:38:

```
GAATTCCATT CAAGAATAGT TCAAACAAGA AGATTACAAA CTATCAATTT CATACACAAT      60

ATAAACGATT AAAAGA ATG AGA TTT CCT TCA ATT TTT ACT GCA GTT TTA         109
               Met Arg Phe Pro Ser Ile Phe Thr Ala Val Leu
                 1               5                  10

TTC GCA GCA TCC TCC GCA TTA GCT GCT CCA GTC AAC ACT ACA ACA GAA      157
Phe Ala Ala Ser Ser Ala Leu Ala Ala Pro Val Asn Thr Thr Thr Glu
             15                  20                  25

GAT GAA ACG GCA CAA ATT CCG GCT GAA GCT GTC ATC GGT TAC TCA GAT      205
Asp Glu Thr Ala Gln Ile Pro Ala Glu Ala Val Ile Gly Tyr Ser Asp
         30                  35                  40

TTA GAA GGG GAT TTC GAT GTT GCT GTT TTG CCA TTT TCC AAC AGC ACA      253
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Leu | Glu | Gly | Asp | Phe | Asp | Val | Ala | Val | Leu | Pro | Phe | Ser | Asn | Ser | Thr |     |
|     | 45  |     |     |     | 50  |     |     |     |     | 55  |     |     |     |     |     |     |
| AAT | AAC | GGG | TTA | TTG | TTT | ATA | AAT | ACT | ACT | ATT | GCC | AGC | ATT | GCT | GCT | 301 |
| Asn | Asn | Gly | Leu | Leu | Phe | Ile | Asn | Thr | Thr | Ile | Ala | Ser | Ile | Ala | Ala |     |
| 60  |     |     |     |     | 65  |     |     |     |     | 70  |     |     |     |     | 75  |     |
| AAA | GAA | GAA | GGG | GTA | TCC | ATG | GCT | AAG | AGA | TTC | GTT | AAC | CAA | CAC | TTG | 349 |
| Lys | Glu | Glu | Gly | Val | Ser | Met | Ala | Lys | Arg | Phe | Val | Asn | Gln | His | Leu |     |
|     |     |     |     | 80  |     |     |     |     | 85  |     |     |     |     | 90  |     |     |
| TGC | GGT | TCC | CAC | TTG | GTT | GAA | GCT | TTG | TAC | TTG | GTT | TGT | GGT | GAA | AGA | 397 |
| Cys | Gly | Ser | His | Leu | Val | Glu | Ala | Leu | Tyr | Leu | Val | Cys | Gly | Glu | Arg |     |
|     |     |     | 95  |     |     |     |     | 100 |     |     |     |     | 105 |     |     |     |
| GGT | TTC | TTC | TAC | ACT | CCA | AAG | ACT | AGA | GGT | ATC | GTT | GAA | CAA | TGT | TGT | 445 |
| Gly | Phe | Phe | Tyr | Thr | Pro | Lys | Thr | Arg | Gly | Ile | Val | Glu | Gln | Cys | Cys |     |
|     |     | 110 |     |     |     |     | 115 |     |     |     |     | 120 |     |     |     |     |
| ACT | TCT | ATC | TGT | TCT | TTG | TAC | CAA | TTG | GAA | AAC | TAC | TGC | AAC |     |     | 487 |
| Thr | Ser | Ile | Cys | Ser | Leu | Tyr | Gln | Leu | Glu | Asn | Tyr | Cys | Asn |     |     |     |
|     | 125 |     |     |     |     | 130 |     |     |     |     | 135 |     |     |     |     |     |

TAGACGCAGC CCGCAGGCTC TAGA 511

( 2 ) INFORMATION FOR SEQ ID NO:39:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Arg | Phe | Pro | Ser | Ile | Phe | Thr | Ala | Val | Leu | Phe | Ala | Ala | Ser | Ser |
| 1   |     |     |     | 5   |     |     |     |     | 10  |     |     |     |     | 15  |     |
| Ala | Leu | Ala | Ala | Pro | Val | Asn | Thr | Thr | Thr | Glu | Asp | Glu | Thr | Ala | Gln |
|     |     |     | 20  |     |     |     | 25  |     |     |     |     | 30  |     |     |     |
| Ile | Pro | Ala | Glu | Ala | Val | Ile | Gly | Tyr | Ser | Asp | Leu | Glu | Gly | Asp | Phe |
|     |     | 35  |     |     |     | 40  |     |     |     |     | 45  |     |     |     |     |
| Asp | Val | Ala | Val | Leu | Pro | Phe | Ser | Asn | Ser | Thr | Asn | Asn | Gly | Leu | Leu |
|     | 50  |     |     |     | 55  |     |     |     |     | 60  |     |     |     |     |     |
| Phe | Ile | Asn | Thr | Thr | Ile | Ala | Ser | Ile | Ala | Ala | Lys | Glu | Glu | Gly | Val |
| 65  |     |     |     | 70  |     |     |     |     | 75  |     |     |     |     |     | 80  |
| Ser | Met | Ala | Lys | Arg | Phe | Val | Asn | Gln | His | Leu | Cys | Gly | Ser | His | Leu |
|     |     |     |     | 85  |     |     |     |     | 90  |     |     |     |     | 95  |     |
| Val | Glu | Ala | Leu | Tyr | Leu | Val | Cys | Gly | Glu | Arg | Gly | Phe | Phe | Tyr | Thr |
|     |     |     | 100 |     |     |     |     | 105 |     |     |     |     | 110 |     |     |
| Pro | Lys | Thr | Arg | Gly | Ile | Val | Glu | Gln | Cys | Cys | Thr | Ser | Ile | Cys | Ser |
|     |     | 115 |     |     |     |     | 120 |     |     |     |     | 125 |     |     |     |
| Leu | Tyr | Gln | Leu | Glu | Asn | Tyr | Cys | Asn |     |     |     |     |     |     |     |
|     |     | 130 |     |     |     | 135 |     |     |     |     |     |     |     |     |     |

( 2 ) INFORMATION FOR SEQ ID NO:40:

( i ) SEQUENCE CHARACTERISTICS:
        ( A ) LENGTH: 511 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

CTTAAGGTAA GTTCTTATCA AGTTTGTTCT TCTAATGTTT GATAGTTAAA GTATGTGTTA 60

TATTTGCTAA TTTTCTTACT CTAAAGGAAG TTAAAAATGA CGTCAAAATA AGCGTCGTAG 120

| GAGGCGTAAT | CGACGAGGTC | AGTTGTGATG | TTGTCTTCTA | CTTTGCCGTG | TTTAAGGCCG | 180 |
| ACTTCGACAG | TAGCCAATGA | GTCTAAATCT | TCCCCTAAAG | CTACAACGAC | AAAACGGTAA | 240 |
| AAGGTTGTCG | TGTTTATTGC | CCAATAACAA | ATATTTATGA | TGATAACGGT | CGTAACGACG | 300 |
| ATTTCTTCTT | CCCCATAGGT | ACCGATTCTC | TAAGCAATTG | GTTGTGAACA | CGCCAAGGGT | 360 |
| GAACCAACTT | CGAAACATGA | ACCAAACACC | ACTTTCTCCA | AAGAAGATGT | GAGGTTTCTG | 420 |
| ATCTCCATAG | CAACTTGTTA | CAACATGAAG | ATAGACAAGA | AACATGGTTA | ACCTTTTGAT | 480 |
| GACGTTGATC | TGCGTCGGGC | GTCCGAGATC | T | | | 511 |

( 2 ) INFORMATION FOR SEQ ID NO:41:

( i ) SEQUENCE CHARACTERISTICS:
  ( A ) LENGTH: 523 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 80..499

( x i ) SEQUENCE DESCRIPTION: SEQ ID NO:41:

```
ATCGAATTCC ATTCAAGAAT AGTTCAAACA AGAAGATTAC AAACTATCAA TTTCATACAC        60

AATATAAACG ATTAAAAGA ATG AGA TTT CCT TCA ATT TTT ACT GCA GTT TTA       112
                       Met Arg Phe Pro Ser Ile Phe Thr Ala Val Leu
                        1               5                       10

TTC GCA GCA TCC TCC GCA TTA GCT GCT CCA GTC AAC ACT ACA ACA GAA       160
Phe Ala Ala Ser Ser Ala Leu Ala Ala Pro Val Asn Thr Thr Thr Glu
                15                  20                  25

GAT GAA ACG GCA CAA ATT CCG GCT GAA GCT GTC ATC GGT TAC TCA GAT       208
Asp Glu Thr Ala Gln Ile Pro Ala Glu Ala Val Ile Gly Tyr Ser Asp
            30                  35                  40

TTA GAA GGG GAT TTC GAT GTT GCT GTT TTG CCA TTT TCC AAC AGC ACA       256
Leu Glu Gly Asp Phe Asp Val Ala Val Leu Pro Phe Ser Asn Ser Thr
        45                  50                  55

AAT AAC GGG TTA TTG TTT ATA AAT ACT ACT ATT GCC AGC ATT GCT GCT       304
Asn Asn Gly Leu Leu Phe Ile Asn Thr Thr Ile Ala Ser Ile Ala Ala
60                  65                  70                  75

AAA GAA GAA GGG GTA TCC ATG GCT AAG AGA TTC GTT AAC CAA CAC TTG       352
Lys Glu Glu Gly Val Ser Met Ala Lys Arg Phe Val Asn Gln His Leu
                80                  85                  90

TGC GGT TCC CAC TTG GTT GAA GCT TTG TAC TTG GTT TGC GGT GAA AGA       400
Cys Gly Ser His Leu Val Glu Ala Leu Tyr Leu Val Cys Gly Glu Arg
            95                  100                 105

GGT TTC TTC TAC ACT CCT AAG TCT GAC GAT GCT AAG GGT ATT GTC GAG       448
Gly Phe Phe Tyr Thr Pro Lys Ser Asp Asp Ala Lys Gly Ile Val Glu
        110                 115                 120

CAA TGC TGT ACC TCC ATC TGC TCC TTG TAC CAA TTG GAA AAC TAC TGC       496
Gln Cys Cys Thr Ser Ile Cys Ser Leu Tyr Gln Leu Glu Asn Tyr Cys
125                 130                 135

AAC TAGACGCAGC CCGCAGGCTC TAGA                                        523
Asn
140
```

( 2 ) INFORMATION FOR SEQ ID NO:42:

( i ) SEQUENCE CHARACTERISTICS:
  ( A ) LENGTH: 140 amino acids ( B ) TYPE: amino acid
( D ) TOPOLOGY: linear ( i i ) MOLECULE TYPE: protein ( x i ) SEQUENCE DESCRIPTION: SEQ ID NO:42:

| Met | Arg | Phe | Pro | Ser | Ile | Phe | Thr | Ala | Val | Leu | Phe | Ala | Ala | Ser | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Leu | Ala | Ala | Pro | Val | Asn | Thr | Thr | Thr | Glu | Asp | Glu | Thr | Ala | Gln |
|     |     |     | 20  |     |     |     |     | 25  |     |     |     |     | 30  |     |     |
| Ile | Pro | Ala | Glu | Ala | Val | Ile | Gly | Tyr | Ser | Asp | Leu | Glu | Gly | Asp | Phe |
|     |     | 35  |     |     |     |     | 40  |     |     |     |     | 45  |     |     |     |
| Asp | Val | Ala | Val | Leu | Pro | Phe | Ser | Asn | Ser | Thr | Asn | Asn | Gly | Leu | Leu |
|     | 50  |     |     |     |     | 55  |     |     |     |     | 60  |     |     |     |     |
| Phe | Ile | Asn | Thr | Thr | Ile | Ala | Ser | Ile | Ala | Ala | Lys | Glu | Glu | Gly | Val |
| 65  |     |     |     |     | 70  |     |     |     |     | 75  |     |     |     |     | 80  |
| Ser | Met | Ala | Lys | Arg | Phe | Val | Asn | Gln | His | Leu | Cys | Gly | Ser | His | Leu |
|     |     |     |     | 85  |     |     |     |     | 90  |     |     |     |     | 95  |     |
| Val | Glu | Ala | Leu | Tyr | Leu | Val | Cys | Gly | Glu | Arg | Gly | Phe | Phe | Tyr | Thr |
|     |     |     | 100 |     |     |     |     | 105 |     |     |     |     | 110 |     |     |
| Pro | Lys | Ser | Asp | Asp | Ala | Lys | Gly | Ile | Val | Glu | Gln | Cys | Cys | Thr | Ser |
|     |     | 115 |     |     |     |     | 120 |     |     |     |     | 125 |     |     |     |
| Ile | Cys | Ser | Leu | Tyr | Gln | Leu | Glu | Asn | Tyr | Cys | Asn |     |     |     |     |
|     | 130 |     |     |     |     | 135 |     |     |     |     | 140 |     |     |     |     |

( 2 ) INFORMATION FOR SEQ ID NO:43:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

| | | | | | |
|---|---|---|---|---|---|
| TAGCTTAAGG | TAAGTTCTTA | TCAAGTTTGT | TCTTCTAATG | TTTGATAGTT | AAAGTATGTG | 60 |
| TTATATTTGC | TAATTTTCTT | ACTCTAAAGG | AAGTTAAAAA | TGACGTCAAA | ATAAGCGTCG | 120 |
| TAGGAGGCGT | AATCGACGAG | GTCAGTTGTG | ATGTTGTCTT | CTACTTTGCC | GTGTTTAAGG | 180 |
| CCGACTTCGA | CAGTAGCCAA | TGAGTCTAAA | TCTTCCCCTA | AAGCTACAAC | GACAAAACGG | 240 |
| TAAAAGGTTG | TCGTGTTTAT | TGCCCAATAA | CAAATATTTA | TGATGATAAC | GGTCGTAACG | 300 |
| ACGATTTCTT | CTTCCCCATA | GGTACCGATT | CTCTAAGCAA | TTGGTTGTGA | ACACGCCAAG | 360 |
| GGTGAACCAA | CTTCGAAACA | TGAACCAAAC | GCCACTTTCT | CCAAAGAAGA | TGTGAGGATT | 420 |
| CAGACTGCTA | CGATTCCCAT | AACAGCTCGT | TACGACATGG | AGGTAGACGA | GGAACATGGT | 480 |
| TAACCTTTTG | ATGACGTTGA | TCTGCGTCGG | GCGTCCGAGA | TCT | | 523 |

( 2 ) INFORMATION FOR SEQ ID NO:44:

( i ) SEQUENCE CHARACTERISTICS:
        ( A ) LENGTH: 535 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..511

( x i ) SEQUENCE DESCRIPTION: SEQ ID NO:44:

```
GAATTCCATT CAAGAATAGT TCAAACAAGA AGATTACAAA CTATCAATTT CATACACAAT         60

ATAAACGATT AAAAGA ATG AGA TTT CCT TCA ATT TTT ACT GCA GTT TTA            109
               Met Arg Phe Pro Ser Ile Phe Thr Ala Val Leu
                 1               5                      10

TTC GCA GCA TCC TCC GCA TTA GCT GCT CCA GTC AAC ACT ACA ACA GAA          157
Phe Ala Ala Ser Ser Ala Leu Ala Ala Pro Val Asn Thr Thr Thr Glu
             15                  20                  25

GAT GAA ACG GCA CAA ATT CCG GCT GAA GCT GTC ATC GGT TAC TCA GAT          205
Asp Glu Thr Ala Gln Ile Pro Ala Glu Ala Val Ile Gly Tyr Ser Asp
         30                  35                  40

TTA GAA GGG GAT TTC GAT GTT GCT GTT TTG CCA TTT TCC AAC AGC ACA          253
Leu Glu Gly Asp Phe Asp Val Ala Val Leu Pro Phe Ser Asn Ser Thr
     45                  50                  55

AAT AAC GGG TTA TTG TTT ATA AAT ACT ACT ATT GCC AGC ATT GCT GCT          301
Asn Asn Gly Leu Leu Phe Ile Asn Thr Thr Ile Ala Ser Ile Ala Ala
 60                  65                  70                  75

AAA GAA GAA GGG GTA TCC ATG GCT AAG AGA GAA GAA GCT GAA GCT GAA          349
Lys Glu Glu Gly Val Ser Met Ala Lys Arg Glu Glu Ala Glu Ala Glu
                 80                  85                  90

GCT AGA TTC GTT AAC CAA CAC TTG TGC GGT TCC CAC TTG GTT GAA GCT          397
Ala Arg Phe Val Asn Gln His Leu Cys Gly Ser His Leu Val Glu Ala
             95                 100                 105

TTG TAC TTG GTT TGT GGT GAA AGA GGT TTC TTC TAC ACT CCA AAG ACT          445
Leu Tyr Leu Val Cys Gly Glu Arg Gly Phe Phe Tyr Thr Pro Lys Thr
         110                 115                 120

AGA GGT ATC GTT GAA CAA TGT TGT ACT TCT ATC TGT TCT TTG TAC CAA          493
Arg Gly Ile Val Glu Gln Cys Cys Thr Ser Ile Cys Ser Leu Tyr Gln
     125                 130                 135

TTG GAA AAC TAC TGC AAC TAGACGCAGC CCGCAGGCTC TAGA                        535
Leu Glu Asn Tyr Cys Asn
140                 145
```

( 2 ) INFORMATION FOR SEQ ID NO:45:

( i ) SEQUENCE CHARACTERISTICS:
( A ) LENGTH: 145 amino acids
( B ) TYPE: amino acid
( D ) TOPOLOGY: linear ( i i ) MOLECULE TYPE: protein ( x i ) SEQUENCE DESCRIPTION: SEQ ID NO:45:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Met Ala Lys Arg Glu Glu Ala Glu Ala Glu Ala Arg Phe Val Asn
                 85                  90                  95

Gln His Leu Cys Gly Ser His Leu Val Glu Ala Leu Tyr Leu Val Cys
             100                 105                 110

Gly Glu Arg Gly Phe Phe Tyr Thr Pro Lys Thr Arg Gly Ile Val Glu
         115                 120                 125
```

Gln Cys Cys Thr Ser Ile Cys Ser Leu Tyr Gln Leu Glu Asn Tyr Cys
130                135                140

Asn
145

( 2 ) INFORMATION FOR SEQ ID NO:46:

( i ) SEQUENCE CHARACTERISTICS:
        ( A ) LENGTH: 535 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

| | | | | | |
|---|---|---|---|---|---|
| CTTAAGGTAA | GTTCTTATCA | AGTTTGTTCT | TCTAATGTTT | GATAGTTAAA | GTATGTGTTA | 60 |
| TATTTGCTAA | TTTTCTTACT | CTAAAGGAAG | TTAAAAATGA | CGTCAAAATA | AGCGTCGTAG | 120 |
| GAGGCGTAAT | CGACGAGGTC | AGTTGTGATG | TTGTCTTCTA | CTTTGCCGTG | TTTAAGGCCG | 180 |
| ACTTCGACAG | TAGCCAATGA | GTCTAAATCT | TCCCCTAAAG | CTACAACGAC | AAAACGGTAA | 240 |
| AAGGTTGTCG | TGTTTATTGC | CCAATAACAA | ATATTTATGA | TGATAACGGT | CGTAACGACG | 300 |
| ATTTCTTCTT | CCCCATAGGT | ACCGATTCTC | TCTTCTTCGA | CTTCGACTTC | GATCTAAGCA | 360 |
| ATTGGTTGTG | AACACGCCAA | GGGTGAACCA | ACTTCGAAAC | ATGAACCAAA | CACCACTTTC | 420 |
| TCCAAAGAAG | ATGTGAGGTT | TCTGATCTCC | ATAGCAACTT | GTTACAACAT | GAAGATAGAC | 480 |
| AAGAAACATG | GTTAACCTTT | TGATGACGTT | GATCTGCGTC | GGGCGTCCGA | GATCT | 535 |

( 2 ) INFORMATION FOR SEQ ID NO:47:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 77..514

( x i ) SEQUENCE DESCRIPTION: SEQ ID NO:47:

GAATTCCATT CAAGAATAGT TCAAACAAGA AGATTACAAA CTATCAATTT CATACACAAT     60

ATAAACGATT AAAAGA ATG AGA TTT CCT TCA ATT TTT ACT GCA GTT TTA     109
                  Met Arg Phe Pro Ser Ile Phe Thr Ala Val Leu
                   1             5                  10

TTC GCA GCA TCC TCC GCA TTA GCT GCT CCA GTC AAC ACT ACA ACA GAA     157
Phe Ala Ala Ser Ser Ala Leu Ala Ala Pro Val Asn Thr Thr Thr Glu
              15                  20                 25

GAT GAA ACG GCA CAA ATT CCG GCT GAA GCT GTC ATC GGT TAC TCA GAT     205
Asp Glu Thr Ala Gln Ile Pro Ala Glu Ala Val Ile Gly Tyr Ser Asp
        30                       35                  40

TTA GAA GGG GAT TTC GAT GTT GCT GTT TTG CCA TTT TCC AAC AGC ACA     253
Leu Glu Gly Asp Phe Asp Val Ala Val Leu Pro Phe Ser Asn Ser Thr
        45                       50                  55

AAT AAC GGG TTA TTG TTT ATA AAT ACT ACT ATT GCC AGC ATT GCT GCT     301
Asn Asn Gly Leu Leu Phe Ile Asn Thr Thr Ile Ala Ser Ile Ala Ala
 60                   65                      70                  75

AAA GAA GAA GGG GTA TCC ATG GCT AAG AGA GAA GAA GCT GAA GCT GAA     349
Lys Glu Glu Gly Val Ser Met Ala Lys Arg Glu Glu Ala Glu Ala Glu
                80                  85                  90

| | | | | | | | | | | | | | | | |
|---|---|---|---|---|---|---|---|---|---|---|---|---|---|---|---|
| GCT | GAA | AGA | TTC | GTT | AAC | CAA | CAC | TTG | TGC | GGT | TCC | CAC | TTG | GTT | GAA | 397 |
| Ala | Glu | Arg | Phe | Val | Asn | Gln | His | Leu | Cys | Gly | Ser | His | Leu | Val | Glu | |
| | | 95 | | | | | 100 | | | | | | 105 | | | |
| GCT | TTG | TAC | TTG | GTT | TGT | GGT | GAA | AGA | GGT | TTC | TTC | TAC | ACT | CCA | AAG | 445 |
| Ala | Leu | Tyr | Leu | Val | Cys | Gly | Glu | Arg | Gly | Phe | Phe | Tyr | Thr | Pro | Lys | |
| | | 110 | | | | | 115 | | | | | | 120 | | | |
| ACT | AGA | GGT | ATC | GTT | GAA | CAA | TGT | TGT | ACT | TCT | ATC | TGT | TCT | TTG | TAC | 493 |
| Thr | Arg | Gly | Ile | Val | Glu | Gln | Cys | Cys | Thr | Ser | Ile | Cys | Ser | Leu | Tyr | |
| | 125 | | | | | 130 | | | | | 135 | | | | | |
| CAA | TTG | GAA | AAC | TAC | TGC | AAC | TAGACGCAGC | | CCGCAGGCTC | | TAGA | | | | | 538 |
| Gln | Leu | Glu | Asn | Tyr | Cys | Asn | | | | | | | | | | |
| 140 | | | | | 145 | | | | | | | | | | | |

( 2 ) INFORMATION FOR SEQ ID NO:48:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

Met Arg Phe Pro Ser Ile Phe Thr Ala Val Leu Phe Ala Ala Ser Ser
1               5                   10                  15

Ala Leu Ala Ala Pro Val Asn Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Met Ala Lys Arg Glu Glu Ala Glu Ala Glu Ala Glu Arg Phe Val
            85                  90                  95

Asn Gln His Leu Cys Gly Ser His Leu Val Glu Ala Leu Tyr Leu Val
            100                 105                 110

Cys Gly Glu Arg Gly Phe Phe Tyr Thr Pro Lys Thr Arg Gly Ile Val
        115                 120                 125

Glu Gln Cys Cys Thr Ser Ile Cys Ser Leu Tyr Gln Leu Glu Asn Tyr
    130                 135                 140

Cys Asn
145

( 2 ) INFORMATION FOR SEQ ID NO:49:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

| | | | | | |
|---|---|---|---|---|---|
| CTTAAGGTAA | GTTCTTATCA | AGTTTGTTCT | TCTAATGTTT | GATAGTAAAA | GTATGTGTTA | 60 |
| TATTTGCTAA | TTTTCTTACT | CTAAAGGAAG | TTAAAAATGA | CGTCAAAATA | AGCGTCGTAG | 120 |
| GAGGCGTAAT | CGACGAGGTC | AGTTGTGATG | TTGTCTTCTA | CTTTGCCGTG | TTTAAGGCCG | 180 |
| ACTTCGACAG | TAGCCAATGA | GTCTAAATCT | TCCCCTAAAG | CTACAACGAC | AAAACGGTAA | 240 |
| AAGGTTGTCG | TGTTTATTGC | CCAATAACAA | ATATTTATGA | TGATAACGGT | CGTAACGACG | 300 |

| | | | | |
|---|---|---|---|---|
| ATTTCTTCTT | CCCCATAGGT | ACCGATTCTC | TCTTCTTCGA | CTTCGACTTC | GACTTTCTAA | 360 |
| GCAATTGGTT | GTGAACACGC | CAAGGGTGAA | CCAACTTCGA | AACATGAACC | AAACACCACT | 420 |
| TTCTCCAAAG | AAGATGTGAG | GTTTCTGATC | TCCATAGCAA | CTTGTTACAA | CATGAAGATA | 480 |
| GACAAGAAAC | ATGGTTAACC | TTTTGATGAC | GTTGATCTGC | GTCGGGCGTC | CGAGATCT | 538 |